United States Patent
Los et al.

(10) Patent No.: US 11,078,504 B2
(45) Date of Patent: Aug. 3, 2021

(54) YEAST HOST CELLS FOR DICARBOXYLIC ACID PRODUCTION

(71) Applicant: DSM IP ASSETS B.V., Heerlen (NL)

(72) Inventors: Alrik Pieter Los, Echt (NL); Zheng Zhao, Echt (NL); René Verwaal, Echt (NL); Jacobus Thomas Pronk, Delft (NL); Rolf Poldermans, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/063,810

(22) PCT Filed: Dec. 22, 2016

(86) PCT No.: PCT/EP2016/082415
§ 371 (c)(1),
(2) Date: Jun. 19, 2018

(87) PCT Pub. No.: WO2017/109091
PCT Pub. Date: Jun. 29, 2017

(65) Prior Publication Data
US 2020/0181657 A1    Jun. 11, 2020

(30) Foreign Application Priority Data
Dec. 23, 2015    (EP) .................................... 15202593

(51) Int. Cl.
*C12P 7/46* (2006.01)
*C12N 9/04* (2006.01)
*C12N 9/02* (2006.01)
*C12N 15/81* (2006.01)

(52) U.S. Cl.
CPC .............. *C12P 7/46* (2013.01); *C12N 9/0006* (2013.01); *C12N 9/0036* (2013.01); *C12N 15/81* (2013.01); *C12Y 101/05003* (2013.01); *C12Y 106/99003* (2013.01)

(58) Field of Classification Search
None
See application file for complete search history.

(56) References Cited

FOREIGN PATENT DOCUMENTS

| EP | 2 826 857 | 1/2015 |
|---|---|---|
| WO | 2012/103261 | 8/2012 |
| WO | 2013/003432 | 1/2013 |
| WO | 2013/004670 | 1/2013 |
| WO | 2014/004616 | 1/2014 |
| WO | WO2014018755 | * 1/2014 |

OTHER PUBLICATIONS

Accession P40215. Feb. 1, 1995 (Year: 1995).*
Accession Q07500. Dec. 12, 2006. (Year: 2006).*
Accession P32191. Oct. 1, 1993. (Year: 1993).*
Accession Q00055. Jul. 1, 1993 (Year: 1993).*
Accession P41911. Nov. 1, 1995 (Year: 1995).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
International Search Report for PCT/EP2016/082415, dated Mar. 13, 2017, 5 pages.
Written Opinion of the ISA for PCT/EP2016/082415, dated Mar. 13, 2017, 7 pages.
Search Report for EP 15202593.8 dated Jun. 16, 2016, 9 pages.
Yan et al. "Construction of reductive pathway in *Saccharomyces cerevisiae* for effective succinic acid fermentation at low pH value", Bioresource Technology., vol. 156, Mar. 1, 2014, XP055279282, 7 pages.
Overkamp et al. "Metabolic Engineering of Glycerol Production in *Saccharomyces cerevisiae*", Applied and Environmental Microbiology, vol. 68, No. 6, Jun. 1, 2002, XP055070029, pp. 2814-2821.
Lee et al. "Engineering cellular redox balance in *Saccharomyces cerevisiae* for improved production of L-lactic acid.", Biotechnology and Bioengineering, vol. 112, No. 4, Apr. 2015, XP055280590, pp. 751-758.

* cited by examiner

*Primary Examiner* — Christian L Fronda
(74) *Attorney, Agent, or Firm* — McBee Moore & Vanik IP, LLC

(57) ABSTRACT

The present invention relates to a host cell which is capable of producing a dicarboxylic acid and which comprises at least one genetic modification in its genome resulting in the deficiency of at least one enzymatic step catalysing the oxidation of a cofactor. The invention also relates to a process for producing a dicarboxylic acid, which method comprises fermenting such a host cell in a suitable fermentation medium and producing the dicarboxylic acid.

15 Claims, 10 Drawing Sheets
Specification includes a Sequence Listing.

SEQUENCE LISTING

<160> NUMBER OF SEQ ID NOS: 70

<210> SEQ ID NO 1
<211> LENGTH: 548
<212> TYPE: PRT
<213> ORGANISM: Escherichia coli

<400> SEQUENCE: 1

Met Ser Asn Lys Pro Phe Ile Tyr Gln Ala Pro Phe Pro Met Gly Lys
1               5                   10                  15

Asp Asn Thr Glu Tyr Tyr Leu Leu Thr Ser Asp Tyr Val Ser Val Ala
            20                  25                  30

```
Asp Phe Asp Gly Glu Thr Ile Leu Lys Val Glu Pro Glu Ala Leu Thr
         35                  40                  45

Leu Leu Ala Gln Gln Ala Phe His Asp Ala Ser Phe Met Leu Arg Pro
 50                  55                  60

Ala His Gln Lys Gln Val Ala Ala Ile Leu His Asp Pro Glu Ala Ser
 65                  70                  75                  80

Glu Asn Asp Lys Tyr Val Ala Leu Gln Phe Leu Arg Asn Ser Glu Ile
                 85                  90                  95

Ala Ala Lys Gly Val Leu Pro Thr Cys Gln Asp Thr Gly Thr Ala Ile
             100                 105                 110

Ile Val Gly Lys Lys Gly Gln Arg Val Trp Thr Gly Gly Asp Glu
         115                 120                 125

Glu Thr Leu Ser Lys Gly Val Tyr Asn Thr Tyr Ile Glu Asp Asn Leu
     130                 135                 140

Arg Tyr Ser Gln Asn Ala Ala Leu Asp Met Tyr Lys Glu Val Asn Thr
145                 150                 155                 160

Gly Thr Asn Leu Pro Ala Gln Ile Asp Leu Tyr Ala Val Asp Gly Asp
                 165                 170                 175

Glu Tyr Lys Phe Leu Cys Val Ala Lys Gly Gly Ser Ala Asn Lys
             180                 185                 190

Thr Tyr Leu Tyr Gln Glu Thr Lys Ala Leu Leu Thr Pro Gly Lys Leu
     195                 200                 205

Lys Asn Phe Leu Val Glu Lys Met Arg Thr Leu Gly Thr Ala Ala Cys
210                 215                 220

Pro Pro Tyr His Ile Ala Phe Val Ile Gly Gly Thr Ser Ala Glu Thr
225                 230                 235                 240

Asn Leu Lys Thr Val Lys Leu Ala Ser Ala His Tyr Tyr Asp Glu Leu
                 245                 250                 255

Pro Thr Glu Gly Asn Glu His Gly Gln Ala Phe Arg Asp Val Gln Leu
             260                 265                 270

Glu Gln Glu Leu Leu Glu Glu Ala Gln Lys Leu Gly Leu Gly Ala Gln
     275                 280                 285

Phe Gly Gly Lys Tyr Phe Ala His Asp Ile Arg Val Ile Arg Leu Pro
290                 295                 300

Arg His Gly Ala Ser Cys Pro Val Gly Met Gly Val Ser Cys Ser Ala
305                 310                 315                 320

Asp Arg Asn Ile Lys Ala Lys Ile Asn Arg Glu Gly Ile Trp Ile Glu
                 325                 330                 335

Lys Leu Glu His Asn Pro Gly Gln Tyr Ile Pro Gln Glu Leu Arg Gln
             340                 345                 350

Ala Gly Glu Gly Glu Ala Val Lys Val Asp Leu Asn Arg Pro Met Lys
     355                 360                 365

Glu Ile Leu Ala Gln Leu Ser Gln Tyr Pro Val Ser Thr Arg Leu Ser
     370                 375                 380

Leu Thr Gly Thr Ile Ile Val Gly Arg Asp Ile Ala His Ala Lys Leu
385                 390                 395                 400

Lys Glu Leu Ile Asp Ala Gly Lys Glu Leu Pro Gln Tyr Ile Lys Asp
                 405                 410                 415

His Pro Ile Tyr Tyr Ala Gly Pro Ala Lys Thr Pro Ala Gly Tyr Pro
             420                 425                 430

Ser Gly Ser Leu Gly Pro Thr Thr Ala Gly Arg Met Asp Ser Tyr Val
     435                 440                 445
```

Asp Leu Leu Gln Ser His Gly Gly Ser Met Ile Met Leu Ala Lys Gly
    450                 455                 460

Asn Arg Ser Gln Gln Val Thr Asp Ala Cys His Lys His Gly Gly Phe
465                 470                 475                 480

Tyr Leu Gly Ser Ile Gly Gly Pro Ala Ala Val Leu Ala Gln Gln Ser
                485                 490                 495

Ile Lys His Leu Glu Cys Val Ala Tyr Pro Glu Leu Gly Met Glu Ala
            500                 505                 510

Ile Trp Lys Ile Glu Val Glu Asp Phe Pro Ala Phe Ile Leu Val Asp
        515                 520                 525

Asp Lys Gly Asn Asp Phe Phe Gln Gln Ile Val Asn Lys Gln Cys Ala
    530                 535                 540

Asn Cys Thr Lys
545

<210> SEQ ID NO 2
<211> LENGTH: 8074
<212> TYPE: DNA
<213> ORGANISM: Artificial sequence
<220> FEATURE:
<221> NAME/KEY: source
<222> LOCATION: 1..8074
<223> OTHER INFORMATION: /organism="Artificial sequence"
      /note="Sequence of plasmid pSUC223"
      /mol_type="unassigned DNA"

<400> SEQUENCE: 2

| | | | | |
|---|---|---|---|---|
| gcgcccaata | cgcaaaccgc | ctctcccccgc | gcgttggccg | attcattaat gcagctggca | 60 |
| cgacaggttt | cccgactgga | aagcgggcag | tgagcgcaac | gcaattaatg tgagttagct | 120 |
| cactcattag | gcaccccagg | ctttacactt | tatgcttccg | gctcgtatgt tgtgtggaat | 180 |
| tgtgagcgga | taacaatttc | acacaggaaa | cagctatgac | catgattacg ccaagcttaa | 240 |
| ttaaaggagg | tgcacgcatt | atggagacca | ctacgatacg | atagctgcgt tgttgttgaa | 300 |
| ggggtttctt | aaggttgttt | tcgttgaagg | taaatattgg | tcgttttgt gcagcatatt | 360 |
| gtcctctaga | tgcaaactct | gcaggtccat | ttgcagtaaa | gtgagttgcc tctcgaagaa | 420 |
| tcattaattt | cgtataaccg | tcactattaa | agtcagaaaa | taaattctgt cgtagacaat | 480 |
| gttaccataa | tgttcttgtc | cattttgcat | acactttaaa | tattcatttg atttctcagg | 540 |
| gttcatgatc | ataataaatt | gcgcattcgc | aaggcggtag | tattataatg gggtccatca | 600 |
| ttctgtagca | agaagttaca | gtacgctgtt | caagcgttaa | acaagataag taatctcgaa | 660 |
| tgaaacattc | atatttcgca | tgagccaaca | tacagttgct | gagtaatctt cattgcgctt | 720 |
| atttatcggc | attgagattg | taaaggaagt | aaaacgcatt | tttgcagatc tgttctctta | 780 |
| tgtatttttta | atcgtccttg | tatggaagta | tcaaggggga | cgttcttcac ctccttggaa | 840 |
| ggatcccagc | gccagtaggg | ttgttgagct | tagtaaaaat | gtgcgcacca caagcctaca | 900 |
| tgactccacg | tcacatgaaa | ccacaccgtg | gggccttgtt | cgctaggaa taggatatgc | 960 |
| gacgaagacg | cttctgctta | gtaaccacac | cacattttca | ggggtcgat ctgcttgctt | 1020 |
| cctttactgt | cacgagcggc | ccataatcgc | gcttttttt | taaaaggcgc gagacagcaa | 1080 |
| acaggaagct | cgggtttcaa | ccttcggagt | ggtcgcagat | ctggagactg gatctttaca | 1140 |
| atacagtaag | gcaagccacc | atctgcttct | taggtgcatg | cgacggtatc cacgtgcaga | 1200 |
| acaacatagt | ctgaagaagg | ggggaggag | catgttcatt | ctctgtagca gtaagagctt | 1260 |
| ggtgataatg | accaaaactg | gagtctcgaa | atcatataaa | tagacaatat attttcacac | 1320 |

-continued

```
aatgagattt gtagtacagt tctattctct ctcttgcata aataagaaat tcatcaagaa   1380
cttggtttga tatttcacca acacacacaa aaaacagtac ttcactaaat ttacacacaa   1440
aacaaaatgt ccaacaagcc tttcatctac caagctccat tcccaatggg taaggacaac   1500
actgaatact acttgttgac ttctgactac gtttccgttg ctgatttcga tggtgaaacc   1560
atcttgaagg ttgaaccaga agccttgact ttgttggctc aacaagcctt ccacgatgct   1620
tctttcatgt tgcgtccagc tcaccaaaag caagttgctg ccattttgca cgacccagaa   1680
gcctccgaaa acgacaaata cgttgctttg caattcttga gaaactctga aattgctgcc   1740
aagggtgtct taccaacttg tcaagacact ggtactgcca tcattgtcgg taagaagggt   1800
caaagagtct ggaccggtgg tggtgacgaa gaaactctat ccaagggtgt ttacaacact   1860
tacattgaag ataatttacg ttactctcaa aatgctgctt tggacatgta caaggaagtc   1920
aacactggta ccaacttgcc agctcaaatc gacttatacg ctgttgacgg tgacgaatac   1980
aagttcttgt gtgttgccaa gggtggtggt tctgctaaca agacctactt gtaccaagaa   2040
accaaggctt tgttgactcc aggtaaattg aagaacttct tggtcgaaaa gatgagaact   2100
ttgggtactg ctgcttgtcc accataccac attgctttcg ttatcggtgg tacttccgct   2160
gaaaccaact tgaaaccgt caaattggct tccgctcact actacgatga attgccaact   2220
gaaggtaacg aacacggtca agccttcaga gatgtccaat ggaacaaga attgttggaa   2280 gaagctcaaa aattaggttt gggtgctcaa tttggtggta aatactttgc tcacgatatc   2340
agagttatca gattaccaag acatggtgct tcttgtccag ttggtatggg tgtttcctgt   2400
tctgctgaca gaaacatcaa ggccaagatc aacagagaag gtatctggat tgaaaaattg   2460
gaacacaacc caggtcaata catcccacaa gaattgagac aagctggtga aggtgaagct   2520
gtcaaggttg acttgaacag accaatgaag gaaatcttgg ctcaattatc tcaatacca   2580 gtttccacca gattatcttt gaccggtacc atcattgtcg gtcgtgacat tgctcatgcc   2640
aagttgaagg aattgattga tgctggtaag gaattgcctc aatacatcaa ggaccatcca   2700
atctactacg ctggtccagc caagaccccca gctggttacc catctggttc tttgggtcca   2760
accaccgctg gtagaatgga ctcttacgtt gacttgctac aatctcacgg tggttccatg   2820
atcatgttgg ctaagggtaa cagatctcaa caagtcaccg atgcttgtca caagcacggt   2880
ggtttctatt tgggttccat tggtggtcca gctgctgtct tggctcaaca atctatcaag   2940
cacttggaat gtgttgctta cccagaattg ggtatggaag ccatctggaa gattgaagtc   3000
gaagatttcc cagcttttcat cttagtcgat gacaagggta acgacttctt ccaacaaatt   3060
gtcaacaagc aatgtgccaa ctgtaccaag taagcgtacg ataaagcaat cttgatgagg   3120
ataatgattt ttttttgaat atacataaat actaccgttt ttctgctaga ttttgtgaag   3180
acgtaaataa gtacatatta cttttttaagc caagacaaga ttaagcatta actttaccct   3240
tttctcttct aagtttcaat actagttatc actgtttaaa agttatgccg agaacgtcgg   3300
cggttaaaat atattaccct gaacgtggtg aattgaagtt ctaggatggt ttaaagattt   3360
ttcctttttg ggaaataagt aaacaatata ttgctgcctt ggcgcgcccc ttccgggccc   3420
acgcgtggcc ggccgcggcc gccagctgaa gcttcgtacg ctgcaggtcg acgaattcta   3480
ccgttcgtat aatgtatgct atacgaagtt atagatctgt ttagcttgcc tcgtccccgc   3540
cgggtcaccc ggccagcgac atggaggccc agaatacccct ccttgacagt cttgacgtgc   3600
gcagctcagg ggcatgatgt gactgtcgcc cgtacattta gcccatacat ccccatgtat   3660
aatcatttgc atccatacat tttgatggcc gcacggcgcg aagcaaaaat tacggctcct   3720
```

```
cgctgcagac ctgcgagcag ggaaacgctc ccctcacaga cgcgttgaat tgtccccacg    3780
ccgcgcccct gtagagaaat ataaaaggtt aggatttgcc actgaggttc ttctttcata    3840
tacttccttt taaaatcttg ctaggataca gttctcacat cacatccgaa cataaacaac    3900
catgggtaag gaaaagactc acgtttcgag gccgcgatta aattccaaca tggatgctga    3960
tttatatggg tataaatggg ctcgcgataa tgtcgggcaa tcaggtgcga caatctatcg    4020
attgtatggg aagcccgatg cgccagagtt gtttctgaaa catggcaaag gtagcgttgc    4080
caatgatgtt acagatgaga tggtcagact aaactggctg acggaattta tgcctcttcc    4140
gaccatcaag cattttatcc gtactcctga tgatgcatgg ttactcacca ctgcgatccc    4200
cggcaaaaca gcattccagg tattagaaga atatcctgat tcaggtgaaa atattgttga    4260
tgcgctggca gtgttcctgc gccggttgca ttcgattcct gtttgtaatt gtccttttaa    4320
cagcgatcgc gtatttcgtc tcgctcaggc gcaatcacga atgaataacg gtttggttga    4380
tgcgagtgat tttgatgacg agcgtaatgg ctggcctgtt gaacaagtct ggaaagaaat    4440
gcataagctt ttgccattct caccggattc agtcgtcact catggtgatt tctcacttga    4500
taaccttatt tttgacgagg ggaaattaat aggttgtatt gatgttggac gagtcggaat    4560
cgcagaccga taccaggatc ttgccatcct atggaactgc ctcggtgagt tttctccttc    4620
attacagaaa cggcttttc aaaaatatgg tattgataat cctgatatga ataaattgca    4680
gtttcatttg atgctcgatg agttttccta atcagtactg acaataaaaa gattcttgtt    4740
ttcaagaact tgtcatttgt atagtttttt tatattgtag ttgttctatt ttaatcaaat    4800
gttagcgtga tttatatttt ttttcgcctc gacatcatct gcccagatgc gaagttaagt    4860
gcgcagaaag taatatcatg cgtcaatcgt atgtgaatgc tggtcgctat actgctgtcg    4920
attcgatact aacgccgcca tccagtgtcg aaaacgagct cataacttcg tataatgtat    4980
gctatacgaa cggtagaatt cgaatcagat ccactagtgg cctatgcggc cgcgatggga    5040
cgtcagcact gtacttgttt ttgcgactag attgtaaatc attctttatt taatctcttt    5100
ctttaactac tgcttaaagt ataatttggt ccgtagttta ataactatac taagcgtaac    5160
aatgcatact gacattataa gcctgaacat tacgagttta agttgtatgt aggcgttctg    5220
taagaggtta ctgcgtaaat tatcaacgaa tgcattggtg tatttgcgaa agctacttct    5280
tttaacaagt atttacataa gaataatggt gatctgctca actgatttgg tgataactct    5340
aactttttta gcaacaattt aaaagataat tcgaacatat ataacagtag gaagaatttg    5400
tgtacgtcaa attaagataa tttagcatta ccaaagttat taacctaaac ataaaatata    5460
tatgagacac atgtggaaat cgtatgaaac aactgttatg aaactgacaa gaatgaatat    5520
atagagtaag ctccgcttgt aaagaggaat cacttaagtg tataaatgtc tcgacgatta    5580
ctttagatcc aagattgatg attgatatta ctctgtaata cttaagctct tttaatagct    5640
cactgttgta ttacgggctc gagtaatacc ggaattcact ggccgtcgtt ttacaacgtc    5700
gtgactggga aaaccctggc gttacccaac ttaatcgcct tgcagcacat ccccctttcg    5760
ccagctggcg taatagcgaa gaggcccgca ccgatcgccc ttcccaacag ttgcgcagcc    5820
tgaatggcga atgcgcctg atgcggtatt ttctccttac gcatctgtgc ggtatttcac    5880
accgcatatg gtgcactctc agtacaatct gctctgatgc cgcatagtta agccagcccc    5940
gacacccgcc aacacccgct gacgcgccct gacgggcttg tctgctcccg gcatccgctt    6000
acagacaagc tgtgaccgtc tccgggagct gcatgtgtca gaggttttca ccgtcatcac    6060
cgaaacgcgc gagacgaaag ggcctcgtga tacgcctatt tttataggtt aatgtcatga    6120
```

-continued

```
taataatggt tcttagacg tcaggtggca cttttcgggg aaatgtgcgc ggaacccta      6180
tttgtttatt tttctaaata cattcaaata tgtatccgct catgagacaa taaccctgat    6240
aaatgcttca ataatattga aaaggaaga gtatgagtat tcaacatttc cgtgtcgccc     6300
ttattcccttt ttttgcggca ttttgccttc ctgtttttgc tcacccagaa acgctggtga   6360
aagtaaaaga tgctgaagat cagttgggtg cacgagtggg ttacatcgaa ctggatctca    6420
acagcggtaa gatccttgag agttttcgcc ccgaagaacg ttttccaatg atgagcactt    6480
ttaaagttct gctatgtggc gcggtattat cccgtattga cgccgggcaa gagcaactcg    6540
gtcgccgcat acactattct cagaatgact tggttgagta ctcaccagtc acagaaaagc    6600
atcttacgga tggcatgaca gtaagagaat tatgcagtgc tgccataacc atgagtgata    6660
acactgcggc caacttactt ctgacaacga tcggaggacc gaaggagcta accgcttttt    6720
tgcacaacat gggggatcat gtaactcgcc ttgatcgttg ggaaccggag ctgaatgaag    6780
ccataccaaa cgacgagcgt gacaccacga tgcctgtagc aatggcaaca acgttgcgca    6840
aactattaac tggcgaacta cttactctag cttcccggca acaattaata gactggatgg    6900
aggcggataa agttgcagga ccacttctgc gctcggccct tccggctggc tggtttattg    6960
ctgataaatc tggagccggt gagcgtgggt ctcgcggtat cattgcagca ctggggccag    7020
atggtaagcc ctcccgtatc gtagttatct acacgacggg gagtcaggca actatggatg    7080
aacgaaatag acagatcgct gagataggtg cctcactgat taagcattgg taactgtcag    7140
accaagttta ctcatatata ctttagattg atttaaaact tcatttttaa tttaaaagga    7200
tctaggtgaa gatcctttt gataatctca tgaccaaaat cccttaacgt gagttttcgt     7260
tccactgagc gtcagacccc gtagaaaaga tcaaaggatc ttcttgagat cctttttttc    7320
tgcgcgtaat ctgctgcttg caaacaaaaa aaccaccgct accagcggtg gtttgtttgc    7380
cggatcaaga gctaccaact ctttttccga aggtaactgg cttcagcaga gcgcagatac    7440
caaatactgt ccttctagtg tagccgtagt taggccacca cttcaagaac tctgtagcac    7500
cgcctacata cctcgctctg ctaatcctgt taccagtggc tgctgccagt ggcgataagt    7560
cgtgtcttac cgggttggac tcaagacgat agttaccgga taaggcgcag cggtcgggct    7620
gaacggggg ttcgtgcaca cagcccagct tggagcgaac gacctacacc gaactgagat     7680
acctacagcg tgagctatga gaaagcgcca cgcttcccga agggagaaag gcggacaggt    7740
atccggtaag cggcagggtc ggaacaggag agcgcacgag ggagcttcca gggggaaacg    7800
cctggtatct ttatagtcct gtcgggtttc gccacctctg acttgagcgt cgatttttgt    7860
gatgctcgtc agggggggcgg agcctatgga aaaacgccag caacgcggcc ttttttacggt   7920
tcctggcctt tgctggcct tttgctcaca tgttctttcc tgcgttatcc cctgattctg     7980
tggataaccg tattaccgcc tttgagtgag ctgataccgc tcgccgcagc cgaacgaccg    8040
agcgcagcga gtcagtgagc gaggaagcgg aaga                                 8074
```

<210> SEQ ID NO 3
<211> LENGTH: 452
<212> TYPE: PRT
<213> ORGANISM: Artificial sequence
<220> FEATURE:
<223> OTHER INFORMATION: Modified protein sequence of YEL047c encoding
      FRD1 (E.C. 1.3.1.6, UniProt accession number P32614)

<400> SEQUENCE: 3

```
Met Asn Glu Leu Val Asn Lys Tyr Asn Ile Pro Val Thr Ile Leu Glu
1               5                   10                  15

Lys Ala Ser Ser Ile Gly Gly Asn Ser Ile Lys Ala Ser Ser Gly Ile
            20                  25                  30

Asn Gly Ala Cys Thr Glu Thr Gln Arg His Phe His Ile Glu Asp Ser
            35                  40                  45

Pro Arg Leu Phe Glu Asp Asp Thr Ile Lys Ser Ala Lys Gly Lys Gly
        50                  55                  60

Val Gln Glu Leu Met Ala Lys Leu Ala Asn Asp Ser Pro Leu Ala Ile
65                  70                  75                  80

Glu Trp Leu Lys Asn Glu Phe Asp Leu Lys Leu Asp Leu Leu Ala Gln
                85                  90                  95

Leu Gly Gly His Ser Val Ala Arg Thr His Arg Ser Ser Gly Lys Leu
            100                 105                 110

Pro Pro Gly Phe Glu Ile Val Ser Ala Leu Ser Asn Asn Leu Lys Lys
        115                 120                 125

Leu Ala Glu Thr Lys Pro Glu Leu Val Lys Ile Asn Leu Asp Ser Lys
    130                 135                 140

Val Val Asp Ile His Glu Lys Asp Gly Ser Ile Ser Ala Val Val Tyr
145                 150                 155                 160

Glu Asp Lys Asn Gly Glu Lys His Met Val Ser Ala Asn Asp Val Val
                165                 170                 175

Phe Cys Ser Gly Gly Phe Gly Phe Ser Lys Glu Met Leu Lys Glu Tyr
            180                 185                 190

Ala Pro Glu Leu Val Asn Leu Pro Thr Thr Asn Gly Gln Gln Thr Thr
        195                 200                 205

Gly Asp Gly Gln Arg Leu Leu Gln Lys Leu Gly Ala Asp Leu Ile Asp
    210                 215                 220

Met Asp Gln Ile Gln Val His Pro Thr Gly Phe Ile Asp Pro Asn Asp
225                 230                 235                 240

Arg Ser Ser Ser Trp Lys Phe Leu Ala Ala Glu Ser Leu Arg Gly Leu
                245                 250                 255

Gly Gly Ile Leu Leu Asn Pro Ile Thr Gly Arg Arg Phe Val Asn Glu
            260                 265                 270

Leu Thr Thr Arg Asp Val Val Thr Ala Ala Ile Gln Lys Val Cys Pro
        275                 280                 285

Gln Glu Asp Asn Arg Ala Leu Leu Val Met Gly Glu Lys Met Tyr Thr
    290                 295                 300

Asp Leu Lys Asn Asn Leu Asp Phe Tyr Met Phe Lys Lys Leu Val Gln
305                 310                 315                 320

Lys Leu Thr Leu Ser Gln Val Val Ser Glu Tyr Asn Leu Pro Ile Thr
                325                 330                 335

Val Ala Gln Leu Cys Glu Glu Leu Gln Thr Tyr Ser Ser Phe Thr Thr
            340                 345                 350

Lys Ala Asp Pro Leu Gly Arg Thr Val Ile Leu Asn Glu Phe Gly Ser
        355                 360                 365

Asp Val Thr Pro Glu Thr Val Phe Ile Gly Glu Val Thr Pro Val
    370                 375                 380

Val His Phe Thr Met Gly Gly Ala Arg Ile Asn Val Lys Ala Gln Val
385                 390                 395                 400

Ile Gly Lys Asn Asp Glu Arg Leu Leu Lys Gly Leu Tyr Ala Ala Gly
                405                 410                 415
```

```
Glu Val Ser Gly Gly Val His Gly Ala Asn Arg Leu Gly Gly Ser Ser
                420                 425                 430

Leu Leu Glu Cys Val Val Phe Gly Arg Thr Ala Ala Glu Ser Ile Ala
            435                 440                 445

Asn Asp Arg Lys
    450

<210> SEQ ID NO 4
<211> LENGTH: 2260
<212> TYPE: DNA
<213> ORGANISM: Artificial sequence
<220> FEATURE:
<221> NAME/KEY: source
<222> LOCATION: 1..2260
<223> OTHER INFORMATION: /organism="Artificial sequence"
      /note="Synthetic TDH3p-FRD1-TDH3t gene"
      /mol_type="unassigned DNA"

<400> SEQUENCE: 4
ttagtcaaaa aattagcctt ttaattctgc tgtaacccgt acatgcccaa aataggggc      60 gggttacaca gaatatataa catcgtaggt gtctgggtga acagtttatt cctggcatcc   120
actaaatata atggagcccg cttttttaagc tggcatccag aaaaaaaaag aatcccagca   180
ccaaaatatt gttttcttca ccaaccatca gttcataggt ccattctctt agcgcaacta   240
cagagaacag gggcacaaac aggcaaaaaa cgggcacaac ctcaatggag tgatgcaacc   300
tgcctggagt aaatgatgac acaaggcaat tgacccacgc atgtatctat ctcattttct   360
tacaccttct attaccttct gctctctctg atttggaaaa agctgaaaaa aaaggttgaa   420
accagttccc tgaaattatt cccctacttg actaataagt atataaagac ggtaggtatt   480
gattgtaatt ctgtaaatct atttcttaaa cttcttaaat tctactttta tagttagtct   540
tttttttagt tttaaaacac caagaactta gtttcgaata acacacata aacaaacaaa    600 atgaacgaat tagtcaacaa atacaacatt ccagtcacca ttttggaaaa ggcttcttcc   660
attggtggta actccatcaa ggcttcctcc ggtatcaacg gtgcttgtac cgaaactcaa   720
agacatttcc acattgaaga ttctccaaga ttgtttgaag atgacaccat caaatctgcc   780
aagggtaagg gtgtccaaga attgatggcc aagttggcta acgactctcc attggccatt   840
gaatggttga aaaatgaatt cgacttgaaa ttggacttgt ggctcaatt aggtggtcac   900 tccgttgcca gaactcaccg ttcttctggt aagttgccac caggtttcga attgtttct    960 gctttgtcca caacttgaa gaaattggct gaaaccaagc cagaattggt caagatcaac  1020
ttggactcca aggttgtcga tatccacgaa aaggacggtt ccatctctgc tgttgtttac  1080
gaagataaga acggtgaaaa gcacatggtt tctgctaacg atgttgtctt ttgttctggt  1140
ggtttcggtt tctccaagga atgttgaag gaatacgctc cagaattggt caacttgcca  1200
accaccaacg tcaacaaac cactggtgat ggtcaaagat tactacaaaa gttgggtgct  1260 gacttgatg acatggacca aatccaagtt cacccaactg gtttcattga cccaaacgac  1320
cgttcttctt cctggaaatt cttggctgct gaatctttga gaggtttggg tggtatcttg  1380
ttgaacccaa tcactggtag aagatttgtc aatgaattga ccaccagaga tgtcgttacc  1440
gctgccatcc aaaaggtctg tccacaagaa gataacagag ctttgttggt catgggtgaa  1500
aagatgtaca ctgacttgaa gaacaacttg gacttctaca tgttcaagaa gttggttcaa  1560
aagttgactt tatctcaagt gtttctgaa tacaacttgc caatcactgt tgctcaatta  1620
tgtgaagaat tgcaaactta ctcctctttc accaccaagg ctgacccttt gggtagaacc  1680
```

```
gttatcttga acgaattcgg ttctgatgtc actccagaaa ctgttgtttt catcggtgaa      1740
gtcactccag ttgtccactt caccatgggt ggtgccagaa tcaacgtcaa ggctcaagtt      1800
atcggtaaga acgatgaaag attattgaag ggtttatacg ctgctggtga agtctctggt      1860
ggtgtccacg gtgctaacag attaggtggt tcctctctat ggaatgtgt tgttttcggt       1920 agaactgctg ctgaatccat tgccaacgac cgcaagtaag gtgaatttac tttaaatctt      1980
gcatttaaat aaattttctt tttatagctt tatgacttag tttcaattta tatactatt      2040 taatgacatt ttcgattcat tgattgaaag ctttgtgttt tttcttgatg cgctattgca     2100
ttgttcttgt ctttttcgcc acatgtaata tctgtagtag atacctgata cattgtggat      2160
gctgagtgaa attttagtta ataatggagg cgctcttaat aatttgggg atattggctt       2220 tttttttaa agtttacaaa tgaatttttt ccgccaggat                              2260

<210> SEQ ID NO 5
<211> LENGTH: 84
<212> TYPE: DNA
<213> ORGANISM: Artificial sequence
<220> FEATURE:
<221> NAME/KEY: source
<222> LOCATION: 1..84
<223> OTHER INFORMATION: /organism="Artificial sequence"
      /note="Primer 1 (TDH3p FW with PDC6 5' overhang)"
      /mol_type="unassigned DNA"

<400> SEQUENCE: 5
gtcctctttt atatacagta taaataaaaa acccacgtaa tatagcaaaa acatattgcc      60
aacaaattag tcaaaaaatt agcc                                             84

<210> SEQ ID NO 6
<211> LENGTH: 82
<212> TYPE: DNA
<213> ORGANISM: Artificial sequence
<220> FEATURE:
<221> NAME/KEY: source
<222> LOCATION: 1..82
<223> OTHER INFORMATION: /organism="Artificial sequence"
      /note="Primer 2 (TDH3t REV with overhang to pSUC228 Cre-1)"
      /mol_type="unassigned DNA"

<400> SEQUENCE: 6
cgctatactg atttaaatat aacttcgtat agcatacatt atacgaacgg tactcgaggt      60
cgaatcctgg cggaaaaaat tc                                               82

<210> SEQ ID NO 7
<211> LENGTH: 86
<212> TYPE: DNA
<213> ORGANISM: Artificial sequence
<220> FEATURE:
<221> NAME/KEY: source
<222> LOCATION: 1..86
<223> OTHER INFORMATION: /organism="Artificial sequence"
      /note="Primer 3 (pSUC228 Cre-1 FW with overhang TDH3t)"
      /mol_type="unassigned DNA"

<400> SEQUENCE: 7
cttaataatt tggggatat tggctttttt ttttaaagtt tacaaatgaa ttttttccgc       60
caggattcga cctcgagtac cgttcg                                           86

<210> SEQ ID NO 8
<211> LENGTH: 21
<212> TYPE: DNA
<213> ORGANISM: Artificial sequence
```

```
<220> FEATURE:
<221> NAME/KEY: source
<222> LOCATION: 1..21
<223> OTHER INFORMATION: /organism="Artificial sequence"
      /note="Primer 4 (DBC-03373, pSUC228 Cre-1 REV)"
      /mol_type="unassigned DNA"

<400> SEQUENCE: 8
gcaatttcgg ctatacgtaa c                                              21

<210> SEQ ID NO 9
<211> LENGTH: 4780
<212> TYPE: DNA
<213> ORGANISM: Artificial sequence
<220> FEATURE:
<221> NAME/KEY: source
<222> LOCATION: 1..4780
<223> OTHER INFORMATION: /organism="Artificial sequence"
      /note="Sequence of plasmid pSUC228"
      /mol_type="unassigned DNA"

<400> SEQUENCE: 9
aaatagcttg ccttgtcccc gccgggtcac ccggccagcg acatggaggc ccagaatacc      60
ctccttgaca gtcttgacgt gcgcagctca ggggcatgat gtgactgtcg cccgtacatt     120
tagcccatac atccccatgt ataatcattt gcatccatac attttgatgg ccgcacggcg     180
cgaagcaaaa attacggctc ctcgctgcag acctgcgagc agggaaacgc tcccctcaca     240
gacgcgttga attgtcccca cgccgcgccc ctgtagagaa atataaaagg ttaggatttg     300
ccactgaggt tcttctttca tatacttcct ttaaaatct tgctaggata cagttctcac     360
atcacatccg aacataaaca accatgggta ccactcttga cgacacggct taccggtacc     420
gcaccagtgt cccggggac gccgaggcca tcgaggcact ggatgggtcc ttcaccaccg     480
acaccgtctt ccgcgtcacc gccaccgggg acggcttcac cctgcgggag gtgccggtgg     540
acccgcccct gaccaaggtg ttccccgacg acgaatcgga cgacgaatcg gacgacgggg     600
aggacggcga cccggactcc cggacgttcg tcgcgtacgg ggacgacggc gacctggcgg     660
gcttcgtggt cgtctcgtac tccggctgga ccgccggct gaccgtcgag gacatcgagg     720
tcgccccgga gcaccggggg cacggggtcg ggcgcgcgtt gatggggctc gcgacggagt     780
tcgcccgcga gcggggcgcc gggcacctct ggctggaggt caccaacgtc aacgcaccgg     840
cgatccacgc gtaccggcgg atggggttca ccctctgcgg cctggacacc gccctgtacg     900
acggcaccgc ctcggacggc agcaggcgc tctacatgag catgccctgc ccctaatcag     960
tactgacaat aaaaagattc ttgttttcaa gaacttgtca tttgtatagt ttttttatat    1020
tgtagttgtt ctattttaat caaatgttag cgtgatttat attttttttc gcctcgacat    1080
catctgccca gatgcgaagt taagtgcgca gaaagtaata tcatgcgtca atcgtatgtg    1140
aatgctggtc gctatactgc tgtcgattcg atactaacgc cgccatccag tgtcgattta    1200
aatctagtac ggattagaag ccgccagcg ggtgacagcc ctccgaagga agactctcct    1260
ccgtgcgtcc tcgtcttcac cggtcgcgtt cctgaaacgc agatgtgcct cgcgccgcac    1320
tgctccgaac aataaagatt ctacaatact agcttttatg gttatgaaga ggaaaaattg    1380
gcagtaacct ggccccacaa accttcaaat gaacgaatca aattaacaac cataggatga    1440
taatgcgatt agttttttag ccttatttct ggggtaatta atcagcgaag cgatgatttt    1500
tgatctatta acagatatat aaatgcaaaa actgcataac cactttaact aatactttca    1560
acattttcgg tttgtattac ttcttattca aatgtaataa agtatcaac aaaaaaattgt    1620
```

```
taatatacct ctatactttta acgtcaagga gaaaaaaccc cggattctag aactagtgga   1680
tcccccgggc tgcaggaatt cgatatcaag cttatcgata ccgtcgaggg gcagagccga   1740
tcctgtacac tttacttaaa accattatct gagtgttaaa tgtccaattt actgaccgta   1800
caccaaaatt tgcctgcatt accggtcgat gcaacgagtg atgaggttcg caagaacctg   1860
atggacatgt tcagggatcg ccaggcgttt tctgagcata cctggaaaat gcttctgtcc   1920
gtttgccggt cgtgggcggc atggtgcaag ttgaataacc ggaaatggtt tcccgcagaa   1980
cctgaagatg ttcgcgatta tcttctatat cttcaggcgc gcggtctggc agtaaaaact   2040
atccagcaac atttgggcca gctaaacatg cttcatcgtc ggtccgggct gccacgacca   2100
agtgacagca atgctgtttc actggttatg cggcggatcc gaaaagaaaa cgttgatgcc   2160
ggtgaacgtg caaaacaggc tctagcgttc gaacgcactg atttcgacca ggttcgttca   2220
ctcatggaaa atagcgatcg ctgccaggat atacgtaatc tggcatttct ggggattgct   2280
tataacaccc tgttacgtat agccgaaatt gcggcgcgcc ggtacctctt aattaactgg   2340
cctcatgggc cttccgctca ctgcccgctt tccagtcggg aaacctgtcg tgccagctgc   2400
attaacatgg tcatagctgt ttccttgcgt attgggcgct ctccgcttcc tcgctcactg   2460
actcgctgcg ctcggtcgtt cgggtaaagc ctggggtgcc taatgagcaa aaggccagca   2520
aaaggccagg aaccgtaaaa aggccgcgtt gctggcgttt ttccataggc tccgcccccc   2580
tgacgagcat cacaaaaatc gacgctcaag tcagaggtgg cgaaacccga caggactata   2640
aagataccag gcgtttcccc ctggaagctc cctcgtgcgc tctcctgttc cgaccctgcc   2700
gcttaccgga tacctgtccg cctttctccc ttcgggaagc gtggcgcttt ctcatagctc   2760
acgctgtagg tatctcagtt cggtgtaggt cgttcgctcc aagctgggct gtgtgcacga   2820
accccccgtt cagcccgacc gctgcgcctt atccggtaac tatcgtcttg agtccaaccc   2880
ggtaagacac gacttatcgc cactggcagc agccactggt aacaggatta gcagagcgag   2940
gtatgtaggc ggtgctacag agttcttgaa gtggtggcct aactacggct acactagaag   3000
aacagtattt ggtatctgcg ctctgctgaa gccagttacc ttcggaaaaa gagttggtag   3060
ctcttgatcc ggcaaacaaa ccaccgctgg tagcggtggt ttttttgttt gcaagcagca   3120
gattacgcgc agaaaaaaag gatctcaaga agatcctttg atcttttcta cggggtctga   3180
cgctcagtgg aacgaaaact cacgttaagg gattttggtc atgagattat caaaaaggat   3240
cttcacctag atccttttaa attaaaaatg aagttttaaa tcaatctaaa gtatatatga   3300
gtaaacttgg tctgacagtt accaatgctt aatcagtgag gcacctatct cagcgatctg   3360
tctatttcgt tcatccatag ttgcctgact ccccgtcgtg tagataacta cgatacggga   3420
gggcttacca tctggcccca gtgctgcaat gataccgcga gaaccacgct caccggctcc   3480
agatttatca gcaataaacc agccagccgg aagggccgag cgcagaagtg gtcctgcaac   3540
tttatccgcc tccatccagt ctattaattg ttgccgggaa gctagagtaa gtagttcgcc   3600
agttaatagt ttgcgcaacg ttgttgccat tgctacaggc atcgtggtgt cacgctcgtc   3660
gtttggtatg gcttcattca gctccggttc ccaacgatca aggcgagtta catgatcccc   3720
catgttgtgc aaaaaagcgg ttagctcctt cggtcctccg atcgttgtca gaagtaagtt   3780
ggccgcagtg ttatcactca tggttatggc agcactgcat aattctctta ctgtcatgcc   3840
atccgtaaga tgcttttctg tgactggtga gtactcaacc aagtcattct gagaatagtg   3900
tatgcggcga ccgagttgct cttgcccggc gtcaatacgg gataataccg cgccacatag   3960
cagaacttta aaagtgctca tcattggaaa acgttcttcg gggcgaaaac tctcaaggat   4020
```

```
cttaccgctg ttgagatcca gttcgatgta acccactcgt gcacccaact gatcttcagc    4080 atctttact  ttcaccagcg tttctgggtg agcaaaaaca ggaaggcaaa atgccgcaaa    4140
aaagggaata agggcgacac ggaaatgttg aatactcata ctcttccttt ttcaatatta    4200
ttgaagcatt tatcagggtt attgtctcat gagcggatac atatttgaat gtatttagaa    4260
aaataaacaa ataggggttc cgcgcacatt tccccgaaaa gtgccaccta aattgtaagc    4320
gttaatattt tgttaaaatt cgcgttaaat ttttgttaaa tcagctcatt ttttaaccaa    4380
taggccgaaa tcggcaaaat cccttataaa tcaaaagaat agaccgagat agggttgagt    4440
ggccgctaca gggcgctccc attcgccatt caggctgcgc aactgttggg aagggcgttt    4500
cggtgcgggc ctcttcgcta ttacgccagc tggcgaaagg gggatgtgct gcaaggcgat    4560
taagttgggt aacgccaggg ttttcccagt cacgacgttg taaaacgacg gccagtgagc    4620
gcgacgtaat acgactcact ataggcgaa ttggcggaag gccgtcaagg cctaggcgcg    4680
ccatgagctc ggcgcgccgc ggccgcaggc ctggcgccca gctggggccc gtcgacctcg    4740
agtaccgttc gtataatgta tgctatacga agttatattt                         4780
```

<210> SEQ ID NO 10
<211> LENGTH: 21
<212> TYPE: DNA
<213> ORGANISM: Artificial sequence
<220> FEATURE:
<221> NAME/KEY: source
<222> LOCATION: 1..21
<223> OTHER INFORMATION: /organism="Artificial sequence"
    /note="Primer 5 (DBC-03374, pSUC225 Cre-2 FW)"
    /mol_type="unassigned DNA"

<400> SEQUENCE: 10

```
cgttcactca tggaaaatag c                                              21
```

<210> SEQ ID NO 11
<211> LENGTH: 85
<212> TYPE: DNA
<213> ORGANISM: Artificial sequence
<220> FEATURE:
<221> NAME/KEY: source
<222> LOCATION: 1..85
<223> OTHER INFORMATION: /organism="Artificial sequence"
    /note="Primer 6 (pSUC225 Cre-2 REV with PDC6 3' overhang)"
    /mol_type="unassigned DNA"

<400> SEQUENCE: 11

```
gtattcaaac tgtgtaagtt tatttatttg caacaataat tcgtttgagt acactactaa    60
tggccggatc ctaccgttcg tatag                                          85
```

<210> SEQ ID NO 12
<211> LENGTH: 1139
<212> TYPE: PRT
<213> ORGANISM: Artificial Sequence
<220> FEATURE:
<223> OTHER INFORMATION: Glycosomal Trypanosoma brucei fumarate
    reductase (FRDg) amino acid sequence lacking 3 aa C-terminal
    targeting signal.

<400> SEQUENCE: 12

```
Met Val Asp Gly Arg Ser Ser Ala Ser Ile Val Ala Val Asp Pro Glu
1               5                   10                  15

Arg Ala Ala Arg Glu Arg Asp Ala Ala Ala Arg Ala Leu Leu Gln Asp
            20                  25                  30
```

```
Ser Pro Leu His Thr Thr Met Gln Tyr Ala Thr Gly Leu Glu Leu
         35                  40                  45

Thr Val Pro Tyr Ala Leu Lys Val Val Ala Ser Ala Asp Thr Phe Asp
 50                  55                  60

Arg Ala Lys Glu Val Ala Asp Glu Val Leu Arg Cys Ala Trp Gln Leu
 65                  70                  75                  80

Ala Asp Thr Val Leu Asn Ser Phe Asn Pro Asn Ser Glu Val Ser Leu
                 85                  90                  95

Val Gly Arg Leu Pro Val Gly Gln Lys His Gln Met Ser Ala Pro Leu
            100                 105                 110

Lys Arg Val Met Ala Cys Cys Gln Arg Val Tyr Asn Ser Ser Ala Gly
            115                 120                 125

Cys Phe Asp Pro Ser Thr Ala Pro Val Ala Lys Ala Leu Arg Glu Ile
        130                 135                 140

Ala Leu Gly Lys Glu Arg Asn Asn Ala Cys Leu Glu Ala Leu Thr Gln
145                 150                 155                 160

Ala Cys Thr Leu Pro Asn Ser Phe Val Ile Asp Phe Glu Ala Gly Thr
                165                 170                 175

Ile Ser Arg Lys His Glu His Ala Ser Leu Asp Leu Gly Gly Val Ser
            180                 185                 190

Lys Gly Tyr Ile Val Asp Tyr Val Ile Asp Asn Ile Asn Ala Ala Gly
        195                 200                 205

Phe Gln Asn Val Phe Phe Asp Trp Gly Gly Asp Cys Arg Ala Ser Gly
210                 215                 220

Met Asn Ala Arg Asn Thr Pro Trp Val Val Gly Ile Thr Arg Pro Pro
225                 230                 235                 240

Ser Leu Asp Met Leu Pro Asn Pro Pro Lys Glu Ala Ser Tyr Ile Ser
                245                 250                 255

Val Ile Ser Leu Asp Asn Glu Ala Leu Ala Thr Ser Gly Asp Tyr Glu
            260                 265                 270

Asn Leu Ile Tyr Thr Ala Asp Asp Lys Pro Leu Thr Cys Thr Tyr Asp
        275                 280                 285

Trp Lys Gly Lys Glu Leu Met Lys Pro Ser Gln Ser Asn Ile Ala Gln
290                 295                 300

Val Ser Val Lys Cys Tyr Ser Ala Met Tyr Ala Asp Ala Leu Ala Thr
305                 310                 315                 320

Ala Cys Phe Ile Lys Arg Asp Pro Ala Lys Val Arg Gln Leu Leu Asp
                325                 330                 335

Gly Trp Arg Tyr Val Arg Asp Thr Val Arg Asp Tyr Arg Val Tyr Val
            340                 345                 350

Arg Glu Asn Glu Arg Val Ala Lys Met Phe Glu Ile Ala Thr Glu Asp
        355                 360                 365

Ala Glu Met Arg Lys Arg Arg Ile Ser Asn Thr Leu Pro Ala Arg Val
    370                 375                 380

Ile Val Val Gly Gly Gly Leu Ala Gly Leu Ser Ala Ala Ile Glu Ala
385                 390                 395                 400

Ala Gly Cys Gly Ala Gln Val Val Leu Met Glu Lys Glu Ala Lys Leu
                405                 410                 415

Gly Gly Asn Ser Ala Lys Ala Thr Ser Gly Ile Asn Gly Trp Gly Thr
            420                 425                 430

Arg Ala Gln Ala Lys Ala Ser Ile Val Asp Gly Gly Lys Tyr Phe Glu
        435                 440                 445
```

```
Arg Asp Thr Tyr Lys Ser Gly Ile Gly Gly Asn Thr Asp Pro Ala Leu
450                 455                 460

Val Lys Thr Leu Ser Met Lys Ser Ala Asp Ala Ile Gly Trp Leu Thr
465                 470                 475                 480

Ser Leu Gly Val Pro Leu Thr Val Leu Ser Gln Leu Gly Gly His Ser
                485                 490                 495

Arg Lys Arg Thr His Arg Ala Pro Asp Lys Lys Asp Gly Thr Pro Leu
            500                 505                 510

Pro Ile Gly Phe Thr Ile Met Lys Thr Leu Glu Asp His Val Arg Gly
        515                 520                 525

Asn Leu Ser Gly Arg Ile Thr Ile Met Glu Asn Cys Ser Val Thr Ser
530                 535                 540

Leu Leu Ser Glu Thr Lys Glu Arg Pro Asp Gly Thr Lys Gln Ile Arg
545                 550                 555                 560

Val Thr Gly Val Glu Phe Thr Gln Ala Gly Ser Lys Thr Thr Ile
                565                 570                 575

Leu Ala Asp Ala Val Ile Leu Ala Thr Gly Gly Phe Ser Asn Asp Lys
                580                 585                 590

Thr Ala Asp Ser Leu Leu Arg Glu His Ala Pro His Leu Val Asn Phe
            595                 600                 605

Pro Thr Thr Asn Gly Pro Trp Ala Thr Gly Asp Gly Val Lys Leu Ala
        610                 615                 620

Gln Arg Leu Gly Ala Gln Leu Val Asp Met Asp Lys Val Gln Leu His
625                 630                 635                 640

Pro Thr Gly Leu Ile Asn Pro Lys Asp Pro Ala Asn Pro Thr Lys Phe
            645                 650                 655

Leu Gly Pro Glu Ala Leu Arg Gly Ser Gly Val Leu Leu Asn Lys
                660                 665                 670

Gln Gly Lys Arg Phe Val Asn Glu Leu Asp Leu Arg Ser Val Val Ser
            675                 680                 685

Lys Ala Ile Met Glu Gln Gly Ala Glu Tyr Pro Gly Ser Gly Gly Ser
690                 695                 700

Met Phe Ala Tyr Cys Val Leu Asn Ala Ala Gln Lys Leu Phe Gly
705                 710                 715                 720

Val Ser Ser His Glu Phe Tyr Trp Lys Lys Met Gly Leu Phe Val Lys
                725                 730                 735

Ala Asp Thr Met Arg Asp Leu Ala Ala Leu Ile Gly Cys Pro Val Glu
            740                 745                 750

Ser Val Gln Gln Thr Leu Glu Glu Tyr Glu Arg Leu Ser Ile Ser Gln
            755                 760                 765

Arg Ser Cys Pro Ile Thr Arg Lys Ser Val Tyr Pro Cys Val Leu Gly
            770                 775                 780

Thr Lys Gly Pro Tyr Tyr Val Ala Phe Val Thr Pro Ser Ile His Tyr
785                 790                 795                 800

Thr Met Gly Gly Cys Leu Ile Ser Pro Ser Ala Glu Ile Gln Met Lys
                805                 810                 815

Asn Thr Ser Ser Arg Ala Pro Leu Ser His Ser Asn Pro Ile Leu Gly
            820                 825                 830

Leu Phe Gly Ala Gly Glu Val Thr Gly Gly Val His Gly Gly Asn Arg
            835                 840                 845

Leu Gly Gly Asn Ser Leu Leu Glu Cys Val Val Phe Gly Arg Ile Ala
850                 855                 860
```

```
Gly Asp Arg Ala Ser Thr Ile Leu Gln Arg Lys Ser Ser Ala Leu Ser
865                 870                 875                 880

Phe Lys Val Trp Thr Thr Val Val Leu Arg Glu Val Arg Glu Gly Gly
                885                 890                 895

Val Tyr Gly Ala Gly Ser Arg Val Leu Arg Phe Asn Leu Pro Gly Ala
            900                 905                 910

Leu Gln Arg Ser Gly Leu Ser Leu Gly Gln Phe Ile Ala Ile Arg Gly
        915                 920                 925

Asp Trp Asp Gly Gln Gln Leu Ile Gly Tyr Tyr Ser Pro Ile Thr Leu
    930                 935                 940

Pro Asp Asp Leu Gly Met Ile Asp Ile Leu Ala Arg Ser Asp Lys Gly
945                 950                 955                 960

Thr Leu Arg Glu Trp Ile Ser Ala Leu Glu Pro Gly Asp Ala Val Glu
                965                 970                 975

Met Lys Ala Cys Gly Gly Leu Val Ile Glu Arg Arg Leu Ser Asp Lys
            980                 985                 990

His Phe Val Phe Met Gly His Ile Ile Asn Lys Leu Cys Leu Ile Ala
        995                1000                1005

Gly Gly Thr Gly Val Ala Pro Met Leu Gln Ile Ile Lys Ala Ala Phe
    1010                1015                1020

Met Lys Pro Phe Ile Asp Thr Leu Glu Ser Val His Leu Ile Tyr Ala
1025                1030                1035                1040

Ala Glu Asp Val Thr Glu Leu Thr Tyr Arg Glu Val Leu Glu Glu Arg
                1045                1050                1055

Arg Arg Glu Ser Arg Gly Lys Phe Lys Lys Thr Phe Val Leu Asn Arg
            1060                1065                1070

Pro Pro Pro Leu Trp Thr Asp Gly Val Gly Phe Ile Asp Arg Gly Ile
        1075                1080                1085

Leu Thr Asn His Val Gln Pro Pro Ser Asp Asn Leu Leu Val Ala Ile
    1090                1095                1100

Cys Gly Pro Pro Val Met Gln Arg Ile Val Lys Ala Thr Leu Lys Thr
1105                1110                1115                1120

Leu Gly Tyr Asn Met Asn Leu Val Arg Thr Val Asp Glu Thr Glu Pro
                1125                1130                1135

Ser Gly Ser

<210> SEQ ID NO 13
<211> LENGTH: 472
<212> TYPE: PRT
<213> ORGANISM: Artificial Sequence
<220> FEATURE:
<223> OTHER INFORMATION: Rhizopus oryzae fumarase amino acid sequence,
      lacking the first 23 N-terminal amino acids.

<400> SEQUENCE: 13

Met Ser Ser Ala Ser Ala Ala Leu Gln Lys Phe Arg Ala Glu Arg Asp
1               5                   10                  15

Thr Phe Gly Asp Leu Gln Val Pro Ala Asp Arg Tyr Trp Gly Ala Gln
            20                  25                  30

Thr Gln Arg Ser Leu Gln Asn Phe Asp Ile Gly Gly Pro Thr Glu Arg
        35                  40                  45

Met Pro Glu Pro Leu Ile Arg Ala Phe Gly Val Leu Lys Lys Ala Ala
    50                  55                  60

Ala Thr Val Asn Met Thr Tyr Gly Leu Asp Pro Lys Val Gly Glu Ala
65                  70                  75                  80
```

```
Ile Gln Lys Ala Ala Asp Glu Val Ile Asp Gly Ser Leu Ile Asp His
            85                  90                  95

Phe Pro Leu Val Val Trp Gln Thr Gly Ser Gly Thr Gln Thr Lys Met
        100                 105                 110

Asn Val Asn Glu Val Ile Ser Asn Arg Ala Ile Glu Leu Leu Gly Gly
        115                 120                 125

Glu Leu Gly Ser Lys Ala Pro Val His Pro Asn Asp His Val Asn Met
    130                 135                 140

Ser Gln Ser Ser Asn Asp Thr Phe Pro Thr Ala Met His Val Ala Ala
145                 150                 155                 160

Val Val Glu Ile His Gly Arg Leu Ile Pro Ala Leu Thr Thr Leu Arg
                165                 170                 175

Asp Ala Leu Gln Ala Lys Ser Ala Glu Phe Glu His Ile Ile Lys Ile
                180                 185                 190

Gly Arg Thr His Leu Gln Asp Ala Thr Pro Leu Thr Leu Gly Gln Glu
                195                 200                 205

Phe Ser Gly Tyr Thr Gln Gln Leu Thr Tyr Gly Ile Ala Arg Val Gln
    210                 215                 220

Gly Thr Leu Glu Arg Leu Tyr Asn Leu Ala Gln Gly Gly Thr Ala Val
225                 230                 235                 240

Gly Thr Gly Leu Asn Thr Arg Lys Gly Phe Asp Ala Lys Val Ala Glu
                245                 250                 255

Ala Ile Ala Ser Ile Thr Gly Leu Pro Phe Lys Thr Ala Pro Asn Lys
                260                 265                 270

Phe Glu Ala Leu Ala Ala His Asp Ala Leu Val Glu Ala His Gly Ala
            275                 280                 285

Leu Asn Thr Val Ala Cys Ser Leu Met Lys Ile Ala Asn Asp Ile Arg
    290                 295                 300

Tyr Leu Gly Ser Gly Pro Arg Cys Gly Leu Gly Glu Leu Ser Leu Pro
305                 310                 315                 320

Glu Asn Glu Pro Gly Ser Ser Ile Met Pro Gly Lys Val Asn Pro Thr
                325                 330                 335

Gln Cys Glu Ala Met Thr Met Val Cys Ala Gln Val Met Gly Asn Asn
                340                 345                 350

Thr Ala Ile Ser Val Ala Gly Ser Asn Gly Gln Phe Glu Leu Asn Val
            355                 360                 365

Phe Lys Pro Val Met Ile Lys Asn Leu Ile Gln Ser Ile Arg Leu Ile
    370                 375                 380

Ser Asp Ala Ser Ile Ser Phe Thr Lys Asn Cys Val Val Gly Ile Glu
385                 390                 395                 400

Ala Asn Glu Lys Lys Ile Ser Ser Ile Met Asn Glu Ser Leu Met Leu
                405                 410                 415

Val Thr Ala Leu Asn Pro His Ile Gly Tyr Asp Lys Ala Ala Lys Cys
            420                 425                 430

Ala Lys Lys Ala His Lys Glu Gly Thr Thr Leu Lys Glu Ala Ala Leu
    435                 440                 445

Ser Leu Gly Tyr Leu Thr Ser Glu Glu Phe Asp Gln Trp Val Arg Pro
450                 455                 460

Glu Asp Met Ile Ser Ala Lys Asp
465                 470
```

<210> SEQ ID NO 14
<211> LENGTH: 538
<212> TYPE: PRT
<213> ORGANISM: Artificial Sequence
<220> FEATURE:
<223> OTHER INFORMATION: Actinobacillus succinogenes phosphoenolpyruvate carboxykinase amino acid sequence, with EGY to DAF modification at pos 120 - 122.

<400> SEQUENCE: 14

```
Met Thr Asp Leu Asn Lys Leu Val Lys Glu Leu Asn Asp Leu Gly Leu
1               5                   10                  15

Thr Asp Val Lys Glu Ile Val Tyr Asn Pro Ser Tyr Glu Gln Leu Phe
            20                  25                  30

Glu Glu Glu Thr Lys Pro Gly Leu Glu Gly Phe Asp Lys Gly Thr Leu
        35                  40                  45

Thr Thr Leu Gly Ala Val Ala Val Asp Thr Gly Ile Phe Thr Gly Arg
    50                  55                  60

Ser Pro Lys Asp Lys Tyr Ile Val Cys Asp Glu Thr Thr Lys Asp Thr
65                  70                  75                  80

Val Trp Trp Asn Ser Glu Ala Ala Lys Asn Asp Asn Lys Pro Met Thr
                85                  90                  95

Gln Glu Thr Trp Lys Ser Leu Arg Glu Leu Val Ala Lys Gln Leu Ser
            100                 105                 110

Gly Lys Arg Leu Phe Val Val Asp Ala Phe Cys Gly Ala Ser Glu Lys
        115                 120                 125

His Arg Ile Gly Val Arg Met Val Thr Glu Val Ala Trp Gln Ala His
    130                 135                 140

Phe Val Lys Asn Met Phe Ile Arg Pro Thr Asp Glu Glu Leu Lys Asn
145                 150                 155                 160

Phe Lys Ala Asp Phe Thr Val Leu Asn Gly Ala Lys Cys Thr Asn Pro
                165                 170                 175

Asn Trp Lys Glu Gln Gly Leu Asn Ser Glu Asn Phe Val Ala Phe Asn
            180                 185                 190

Ile Thr Glu Gly Ile Gln Leu Ile Gly Gly Thr Trp Tyr Gly Gly Glu
        195                 200                 205

Met Lys Lys Gly Met Phe Ser Met Met Asn Tyr Phe Leu Pro Leu Lys
    210                 215                 220

Gly Val Ala Ser Met His Cys Ser Ala Asn Val Gly Lys Asp Gly Asp
225                 230                 235                 240

Val Ala Ile Phe Phe Gly Leu Ser Gly Thr Gly Lys Thr Thr Leu Ser
                245                 250                 255

Thr Asp Pro Lys Arg Gln Leu Ile Gly Asp Asp Glu His Gly Trp Asp
            260                 265                 270

Glu Ser Gly Val Phe Asn Phe Glu Gly Gly Cys Tyr Ala Lys Thr Ile
        275                 280                 285

Asn Leu Ser Gln Glu Asn Glu Pro Asp Ile Tyr Gly Ala Ile Arg Arg
    290                 295                 300

Asp Ala Leu Leu Glu Asn Val Val Arg Ala Asp Gly Ser Val Asp
305                 310                 315                 320

Phe Asp Asp Gly Ser Lys Thr Glu Asn Thr Arg Val Ser Tyr Pro Ile
                325                 330                 335

Tyr His Ile Asp Asn Ile Val Arg Pro Val Ser Lys Ala Gly His Ala
            340                 345                 350

Thr Lys Val Ile Phe Leu Thr Ala Asp Ala Phe Gly Val Leu Pro Pro
        355                 360                 365
```

```
Val Ser Lys Leu Thr Pro Glu Gln Thr Glu Tyr Tyr Phe Leu Ser Gly
    370                 375                 380

Phe Thr Ala Lys Leu Ala Gly Thr Glu Arg Gly Val Thr Glu Pro Thr
385                 390                 395                 400

Pro Thr Phe Ser Ala Cys Phe Gly Ala Ala Phe Leu Ser Leu His Pro
                405                 410                 415

Ile Gln Tyr Ala Asp Val Leu Val Glu Arg Met Lys Ala Ser Gly Ala
                420                 425                 430

Glu Ala Tyr Leu Val Asn Thr Gly Trp Asn Gly Thr Gly Lys Arg Ile
                435                 440                 445

Ser Ile Lys Asp Thr Arg Gly Ile Ile Asp Ala Ile Leu Asp Gly Ser
    450                 455                 460

Ile Glu Lys Ala Glu Met Gly Glu Leu Pro Ile Phe Asn Leu Ala Ile
465                 470                 475                 480

Pro Lys Ala Leu Pro Gly Val Asp Pro Ala Ile Leu Asp Pro Arg Asp
                485                 490                 495

Thr Tyr Ala Asp Lys Ala Gln Trp Gln Val Lys Ala Glu Asp Leu Ala
                500                 505                 510

Asn Arg Phe Val Lys Asn Phe Val Lys Tyr Thr Ala Asn Pro Glu Ala
                515                 520                 525

Ala Lys Leu Val Gly Ala Gly Pro Lys Ala
                530                 535
```

<210> SEQ ID NO 15
<211> LENGTH: 340
<212> TYPE: PRT
<213> ORGANISM: Artificial Sequence
<220> FEATURE:
<223> OTHER INFORMATION: Saccharomyces cerevisiae peroxisomal malate
    dehydrogenase (Mdh3) amino acid sequence, lacking the 3 C-terminal
    peroxisomal targeting sequence (SKL).

<400> SEQUENCE: 15

```
Met Val Lys Val Ala Ile Leu Gly Ala Ser Gly Gly Val Gly Gln Pro
1               5                   10                  15

Leu Ser Leu Leu Leu Lys Leu Ser Pro Tyr Val Ser Glu Leu Ala Leu
                20                  25                  30

Tyr Asp Ile Arg Ala Ala Glu Gly Ile Gly Lys Asp Leu Ser His Ile
            35                  40                  45

Asn Thr Asn Ser Ser Cys Val Gly Tyr Asp Lys Asp Ser Ile Glu Asn
    50                  55                  60

Thr Leu Ser Asn Ala Gln Val Val Leu Ile Pro Ala Gly Val Pro Arg
65                  70                  75                  80

Lys Pro Gly Leu Thr Arg Asp Asp Leu Phe Lys Met Asn Ala Gly Ile
                85                  90                  95

Val Lys Ser Leu Val Thr Ala Val Gly Lys Phe Ala Pro Asn Ala Arg
                100                 105                 110

Ile Leu Val Ile Ser Asn Pro Val Asn Ser Leu Val Pro Ile Ala Val
            115                 120                 125

Glu Thr Leu Lys Lys Met Gly Lys Phe Lys Pro Gly Asn Val Met Gly
    130                 135                 140

Val Thr Asn Leu Asp Leu Val Arg Ala Glu Thr Phe Leu Val Asp Tyr
145                 150                 155                 160

Leu Met Leu Lys Asn Pro Lys Ile Gly Gln Glu Gln Asp Lys Thr Thr
                165                 170                 175
```

```
Met His Arg Lys Val Thr Val Ile Gly Gly His Ser Gly Glu Thr Ile
            180                 185                 190

Ile Pro Ile Ile Thr Asp Lys Ser Leu Val Phe Gln Leu Asp Lys Gln
        195                 200                 205

Tyr Glu His Phe Ile His Arg Val Gln Phe Gly Gly Asp Glu Ile Val
    210                 215                 220

Lys Ala Lys Gln Gly Ala Gly Ser Ala Thr Leu Ser Met Ala Phe Ala
225                 230                 235                 240

Gly Ala Lys Phe Ala Glu Glu Val Leu Arg Ser Phe His Asn Glu Lys
                245                 250                 255

Pro Glu Thr Glu Ser Leu Ser Ala Phe Val Tyr Leu Pro Gly Leu Lys
            260                 265                 270

Asn Gly Lys Lys Ala Gln Gln Leu Val Gly Asp Asn Ser Ile Glu Tyr
        275                 280                 285

Phe Ser Leu Pro Ile Val Leu Arg Asn Gly Ser Val Val Ser Ile Asp
    290                 295                 300

Thr Ser Val Leu Glu Lys Leu Ser Pro Arg Glu Gln Leu Val Asn
305                 310                 315                 320

Thr Ala Val Lys Glu Leu Arg Lys Asn Ile Glu Lys Gly Lys Ser Phe
                325                 330                 335

Ile Leu Asp Ser
            340

<210> SEQ ID NO 16
<211> LENGTH: 1180
<212> TYPE: PRT
<213> ORGANISM: Saccharomyces cerevisiae

<400> SEQUENCE: 16

Met Ser Ser Ser Lys Lys Leu Ala Gly Leu Arg Asp Asn Phe Ser Leu
1               5                   10                  15

Leu Gly Glu Lys Asn Lys Ile Leu Val Ala Asn Arg Gly Glu Ile Pro
            20                  25                  30

Ile Arg Ile Phe Arg Ser Ala His Glu Leu Ser Met Arg Thr Ile Ala
        35                  40                  45

Ile Tyr Ser His Glu Asp Arg Leu Ser Met His Arg Leu Lys Ala Asp
    50                  55                  60

Glu Ala Tyr Val Ile Gly Glu Glu Gly Gln Tyr Thr Pro Val Gly Ala
65                  70                  75                  80

Tyr Leu Ala Met Asp Glu Ile Ile Glu Ile Ala Lys Lys His Lys Val
                85                  90                  95

Asp Phe Ile His Pro Gly Tyr Gly Phe Leu Ser Glu Asn Ser Glu Phe
            100                 105                 110

Ala Asp Lys Val Val Lys Ala Gly Ile Thr Trp Ile Gly Pro Pro Ala
        115                 120                 125

Glu Val Ile Asp Ser Val Gly Asp Lys Val Ser Ala Arg His Leu Ala
    130                 135                 140

Ala Arg Ala Asn Val Pro Thr Val Pro Gly Thr Pro Gly Pro Ile Glu
145                 150                 155                 160

Thr Val Gln Glu Ala Leu Asp Phe Val Asn Glu Tyr Gly Tyr Pro Val
                165                 170                 175

Ile Ile Lys Ala Ala Phe Gly Gly Gly Gly Arg Gly Met Arg Val Val
            180                 185                 190

Arg Glu Gly Asp Asp Val Ala Asp Ala Phe Gln Arg Ala Thr Ser Glu
        195                 200                 205
```

```
Ala Arg Thr Ala Phe Gly Asn Gly Thr Cys Phe Val Glu Arg Phe Leu
210                 215                 220

Asp Lys Pro Lys His Ile Glu Val Gln Leu Leu Ala Asp Asn His Gly
225                 230                 235                 240

Asn Val Val His Leu Phe Glu Arg Asp Cys Ser Val Gln Arg His
                245                 250                 255

Gln Lys Val Val Glu Val Ala Pro Ala Lys Thr Leu Pro Arg Glu Val
            260                 265                 270

Arg Asp Ala Ile Leu Thr Asp Ala Val Lys Leu Ala Lys Val Cys Gly
                275                 280                 285

Tyr Arg Asn Ala Gly Thr Ala Glu Phe Leu Val Asp Asn Gln Asn Arg
290                 295                 300

His Tyr Phe Ile Glu Ile Asn Pro Arg Ile Gln Val Glu His Thr Ile
305                 310                 315                 320

Thr Glu Glu Ile Thr Gly Ile Asp Ile Val Ser Ala Gln Ile Gln Ile
                325                 330                 335

Ala Ala Gly Ala Thr Leu Thr Gln Leu Gly Leu Leu Gln Asp Lys Ile
                340                 345                 350

Thr Thr Arg Gly Phe Ser Ile Gln Cys Arg Ile Thr Thr Glu Asp Pro
            355                 360                 365

Ser Lys Asn Phe Gln Pro Asp Thr Gly Arg Leu Glu Val Tyr Arg Ser
370                 375                 380

Ala Gly Gly Asn Gly Val Arg Leu Asp Gly Gly Asn Ala Tyr Ala Gly
385                 390                 395                 400

Ala Thr Ile Ser Pro His Tyr Asp Ser Met Leu Val Lys Cys Ser Cys
                405                 410                 415

Ser Gly Ser Thr Tyr Glu Ile Val Arg Arg Lys Met Ile Arg Ala Leu
            420                 425                 430

Ile Glu Phe Arg Ile Arg Gly Val Lys Thr Asn Ile Pro Phe Leu Leu
                435                 440                 445

Thr Leu Leu Thr Asn Pro Val Phe Ile Glu Gly Thr Tyr Trp Thr Thr
450                 455                 460

Phe Ile Asp Asp Thr Pro Gln Leu Phe Gln Met Val Ser Ser Gln Asn
465                 470                 475                 480

Arg Ala Gln Lys Leu Leu His Tyr Leu Ala Asp Leu Ala Val Asn Gly
            485                 490                 495

Ser Ser Ile Lys Gly Gln Ile Gly Leu Pro Lys Leu Lys Ser Asn Pro
                500                 505                 510

Ser Val Pro His Leu His Asp Ala Gln Gly Asn Val Ile Asn Val Thr
            515                 520                 525

Lys Ser Ala Pro Pro Ser Gly Trp Arg Gln Val Leu Leu Glu Lys Gly
530                 535                 540

Pro Ser Glu Phe Ala Lys Gln Val Arg Gln Phe Asn Gly Thr Leu Leu
545                 550                 555                 560

Met Asp Thr Thr Trp Arg Asp Ala His Gln Ser Leu Leu Ala Thr Arg
                565                 570                 575

Val Arg Thr His Asp Leu Ala Thr Ile Ala Pro Thr Thr Ala His Ala
            580                 585                 590

Leu Ala Gly Ala Phe Ala Leu Glu Cys Trp Gly Gly Ala Thr Phe Asp
                595                 600                 605

Val Ala Met Arg Phe Leu His Glu Asp Pro Trp Glu Arg Leu Arg Lys
610                 615                 620
```

-continued

Leu Arg Ser Leu Val Pro Asn Ile Pro Phe Gln Met Leu Leu Arg Gly
625                 630                 635                 640

Ala Asn Gly Val Ala Tyr Ser Ser Leu Pro Asp Asn Ala Ile Asp His
            645                 650                 655

Phe Val Lys Gln Ala Lys Asp Asn Gly Val Asp Ile Phe Arg Val Phe
        660                 665                 670

Asp Ala Leu Asn Asp Leu Glu Gln Leu Lys Val Gly Val Asn Ala Val
    675                 680                 685

Lys Lys Ala Gly Val Val Glu Ala Thr Val Cys Tyr Ser Gly Asp
690                 695                 700

Met Leu Gln Pro Gly Lys Lys Tyr Asn Leu Asp Tyr Tyr Leu Glu Val
705                 710                 715                 720

Val Glu Lys Ile Val Gln Met Gly Thr His Ile Leu Gly Ile Lys Asp
                725                 730                 735

Met Ala Gly Thr Met Lys Pro Ala Ala Ala Lys Leu Leu Ile Gly Ser
            740                 745                 750

Leu Arg Thr Arg Tyr Pro Asp Leu Pro Ile His Val His Ser His Asp
        755                 760                 765

Ser Ala Gly Thr Ala Val Ala Ser Met Thr Ala Cys Ala Leu Ala Gly
    770                 775                 780

Ala Asp Val Val Asp Val Ala Ile Asn Ser Met Ser Gly Leu Thr Ser
785                 790                 795                 800

Gln Pro Ser Ile Asn Ala Leu Leu Ala Ser Leu Glu Gly Asn Ile Asp
                805                 810                 815

Thr Gly Ile Asn Val Glu His Val Arg Glu Leu Asp Ala Tyr Trp Ala
            820                 825                 830

Glu Met Arg Leu Leu Tyr Ser Cys Phe Glu Ala Asp Leu Lys Gly Pro
        835                 840                 845

Asp Pro Glu Val Tyr Gln His Glu Ile Pro Gly Gly Gln Leu Thr Asn
    850                 855                 860

Leu Leu Phe Gln Ala Gln Gln Leu Gly Leu Gly Glu Gln Trp Ala Glu
865                 870                 875                 880

Thr Lys Arg Ala Tyr Arg Glu Ala Asn Tyr Leu Leu Gly Asp Ile Val
                885                 890                 895

Lys Val Thr Pro Thr Ser Lys Val Val Gly Asp Leu Ala Gln Phe Met
            900                 905                 910

Val Ser Asn Lys Leu Thr Ser Asp Asp Ile Arg Arg Leu Ala Asn Ser
        915                 920                 925

Leu Asp Phe Pro Asp Ser Val Met Asp Phe Phe Glu Gly Leu Ile Gly
    930                 935                 940

Gln Pro Tyr Gly Gly Phe Pro Glu Pro Leu Arg Ser Asp Val Leu Arg
945                 950                 955                 960

Asn Lys Arg Arg Lys Leu Thr Cys Arg Pro Gly Leu Glu Leu Glu Pro
                965                 970                 975

Phe Asp Leu Glu Lys Ile Arg Glu Asp Leu Gln Asn Arg Phe Gly Asp
            980                 985                 990

Ile Asp Glu Cys Asp Val Ala Ser Tyr Asn Met Tyr Pro Arg Val Tyr
        995                 1000                1005

Glu Asp Phe Gln Lys Ile Arg Glu Thr Tyr Gly Asp Leu Ser Val Leu
    1010                1015                1020

Pro Thr Lys Asn Phe Leu Ala Pro Ala Glu Pro Asp Glu Glu Ile Glu
1025                1030                1035                1040

Val Thr Ile Glu Gln Gly Lys Thr Leu Ile Ile Lys Leu Gln Ala Val
            1045                1050                1055

Gly Asp Leu Asn Lys Lys Thr Gly Gln Arg Glu Val Tyr Phe Glu Leu
        1060                1065                1070

Asn Gly Glu Leu Arg Lys Ile Arg Val Ala Asp Lys Ser Gln Asn Ile
        1075                1080                1085

Gln Ser Val Ala Lys Pro Lys Ala Asp Val His Asp Thr His Gln Ile
        1090                1095                1100

Gly Ala Pro Met Ala Gly Val Ile Ile Glu Val Lys Val His Lys Gly
1105                1110                1115                1120

Ser Leu Val Lys Lys Gly Glu Ser Ile Ala Val Leu Ser Ala Met Lys
                1125                1130                1135

Met Glu Met Val Val Ser Ser Pro Ala Asp Gly Gln Val Lys Asp Val
            1140                1145                1150

Phe Ile Lys Asp Gly Glu Ser Val Asp Ala Ser Asp Leu Leu Val Val
        1155                1160                1165

Leu Glu Glu Glu Thr Leu Pro Pro Ser Gln Lys Lys
        1170                1175                1180

<210> SEQ ID NO 17
<211> LENGTH: 542
<212> TYPE: PRT
<213> ORGANISM: Kluyveromyces lactis

<400> SEQUENCE: 17

Met Val Ser Val Lys Ala Ser Ala Glu Lys Lys Glu Phe Leu Gln
1               5                   10                  15

Ser Gln Ile Asp Glu Ile Glu Lys Trp Trp Ser Glu Pro Arg Trp Lys
            20                  25                  30

Asp Thr Lys Arg Ile Tyr Ser Ala Tyr Glu Ile Ala Lys Arg Arg Gly
        35                  40                  45

Ser Val Lys Pro Asn Thr Phe Pro Ser Thr Val Met Ser Gln Lys Leu
    50                  55                  60

Phe Lys Ile Leu Gly Glu His Ala Lys Asn Gly Thr Val Ser Lys Thr
65                  70                  75                  80

Phe Gly Ala Leu Asp Pro Val Gln Val Thr Gln Met Ser Lys Tyr Leu
                85                  90                  95

Asp Thr Ile Tyr Val Ser Gly Trp Gln Cys Ser Ser Thr Ala Ser Thr
            100                 105                 110

Ser Asn Glu Pro Gly Pro Asp Leu Ala Asp Tyr Pro Met Asp Thr Val
        115                 120                 125

Pro Asn Lys Val Glu His Leu Phe Lys Ala Gln Gln Phe His Asp Arg
    130                 135                 140

Lys Gln Trp Glu Arg Ile Cys Asp Gly Thr Ile Glu Glu Ser Glu Ile
145                 150                 155                 160

Ile Asp Tyr Leu Thr Pro Ile Val Ala Asp Gly Asp Ala Gly His Gly
                165                 170                 175

Gly Leu Thr Ala Val Phe Lys Leu Thr Lys Met Phe Ile Glu Arg Gly
            180                 185                 190

Ala Ala Gly Ile His Ile Glu Asp Gln Thr Ser Thr Asn Lys Lys Cys
        195                 200                 205

Gly His Met Ala Gly Arg Cys Val Ile Pro Val Gln Glu His Ile Asn
    210                 215                 220

Arg Leu Ile Thr Cys Arg Met Ala Ala Asp Val Leu Gly Ser Asp Leu
225                 230                 235                 240

```
Ile Leu Val Ala Arg Thr Asp Ser Glu Ala Ala Thr Leu Leu Ser Ser
                245                 250                 255

Thr Ala Asp Ser Arg Asp His Tyr Phe Ile Leu Gly Ala Ser Asn Pro
            260                 265                 270

Ala Val Lys Gly Lys Pro Leu Asn Asp Leu Leu Asn Lys Ala Ile Leu
        275                 280                 285

Asp Gly Ala Thr Ile Asp Leu Gln Thr Ile Glu Lys Glu Trp Leu
    290                 295                 300

Ala Lys Ala Asp Val Lys Leu Phe His Glu Val Phe Ala Asp Ala Ala
305                 310                 315                 320

Lys Ala Ala Gly Lys Asp Gln Ser Val Ile Asp Gln Phe Asn Ser Lys
                325                 330                 335

Val Asn Pro Leu Ser Glu Thr Ser Ile Tyr Glu Met Gln Ala Leu Ala
            340                 345                 350

Lys Glu Leu Leu Gly Thr Glu Leu Phe Phe Asp Trp Asp Leu Pro Arg
        355                 360                 365

Gly Arg Glu Gly Leu Tyr Arg Tyr Gln Gly Gly Thr Gln Cys Ser Val
    370                 375                 380

Met Arg Ala Arg Ala Phe Ala Pro Tyr Ala Asp Leu Cys Trp Met Glu
385                 390                 395                 400

Ser Asn Tyr Pro Asp Tyr Glu Gln Ala Lys Glu Phe Ala Glu Gly Val
                405                 410                 415

Thr Ala Lys Phe Pro Gly Lys Trp Met Ala Tyr Asn Leu Ser Pro Ser
            420                 425                 430

Phe Asn Trp Thr Lys Ala Met Ser Val Asp Glu Gln Glu Thr Phe Ile
        435                 440                 445

Gln Arg Leu Gly Asp Leu Gly Tyr Ile Trp Gln Phe Ile Thr Leu Ala
    450                 455                 460

Gly Leu His Thr Ser Gly Leu Ala Ile Glu Gln Phe Ser Lys Asn Phe
465                 470                 475                 480

Ala Lys Leu Gly Met Lys Ala Tyr Ala Gln Asp Ile Gln Lys Lys Glu
                485                 490                 495

Leu Asp Asn Gly Ile Asp Met Val Lys His Gln Lys Trp Ser Gly Ala
            500                 505                 510

Glu Tyr Ile Asp Gly Leu Leu Arg Leu Ala Gln Gly Gly Leu Ala Ala
        515                 520                 525

Thr Ala Ala Met Gly Gln Gly Val Thr Glu Asp Gln Phe Lys
    530                 535                 540

<210> SEQ ID NO 18
<211> LENGTH: 551
<212> TYPE: PRT
<213> ORGANISM: Artificial Sequence
<220> FEATURE:
<223> OTHER INFORMATION: Sacharomyces cerevisiae malate synthase amino
      acid sequence (artificial) Saccharomyces cerevisiae peroxisomal
      malate synthase (Mls1) amino acid sequence, lacking the 3
      C-terminal peroxisomal targeting

<400> SEQUENCE: 18

Met Val Lys Val Ser Leu Asp Asn Val Lys Leu Leu Val Asp Val Asp
1               5                   10                  15

Lys Glu Pro Phe Phe Lys Pro Ser Ser Thr Thr Val Gly Asp Ile Leu
                20                  25                  30

Thr Lys Asp Ala Leu Glu Phe Ile Val Leu Leu His Arg Thr Phe Asn
            35                  40                  45
```

```
Asn Lys Arg Lys Gln Leu Leu Glu Asn Arg Gln Val Gln Lys Lys
     50                  55                  60

Leu Asp Ser Gly Ser Tyr His Leu Asp Phe Leu Pro Glu Thr Ala Asn
 65                  70                  75                  80

Ile Arg Asn Asp Pro Thr Trp Gln Gly Pro Ile Leu Ala Pro Gly Leu
                 85                  90                  95

Ile Asn Arg Ser Thr Glu Ile Thr Gly Pro Pro Leu Arg Asn Met Leu
            100                 105                 110

Ile Asn Ala Leu Asn Ala Pro Val Asn Thr Tyr Met Thr Asp Phe Glu
            115                 120                 125

Asp Ser Ala Ser Pro Thr Trp Asn Asn Met Val Tyr Gly Gln Val Asn
130                 135                 140

Leu Tyr Asp Ala Ile Arg Asn Gln Ile Asp Phe Asp Thr Pro Arg Lys
145                 150                 155                 160

Ser Tyr Lys Leu Asn Gly Asn Val Ala Asn Leu Pro Thr Ile Ile Val
                165                 170                 175

Arg Pro Arg Gly Trp His Met Val Glu Lys His Leu Tyr Val Asp Asp
            180                 185                 190

Glu Pro Ile Ser Ala Ser Ile Phe Asp Phe Gly Leu Tyr Phe Tyr His
            195                 200                 205

Asn Ala Lys Glu Leu Ile Lys Leu Gly Lys Gly Pro Tyr Phe Tyr Leu
210                 215                 220

Pro Lys Met Glu His His Leu Glu Ala Lys Leu Trp Asn Asp Val Phe
225                 230                 235                 240

Cys Val Ala Gln Asp Tyr Ile Gly Ile Pro Arg Gly Thr Ile Arg Ala
                245                 250                 255

Thr Val Leu Ile Glu Thr Leu Pro Ala Ala Phe Gln Met Glu Glu Ile
            260                 265                 270

Ile Tyr Gln Leu Arg Gln His Ser Ser Gly Leu Asn Cys Gly Arg Trp
            275                 280                 285

Asp Tyr Ile Phe Ser Thr Ile Lys Arg Leu Arg Asn Asp Pro Asn His
290                 295                 300

Ile Leu Pro Asn Arg Asn Gln Val Thr Met Thr Ser Pro Phe Met Asp
305                 310                 315                 320

Ala Tyr Val Lys Arg Leu Ile Asn Thr Cys His Arg Arg Gly Val His
                325                 330                 335

Ala Met Gly Gly Met Ala Ala Gln Ile Pro Ile Lys Asp Asp Pro Ala
            340                 345                 350

Ala Asn Glu Lys Ala Met Thr Lys Val Arg Asn Asp Lys Ile Arg Glu
            355                 360                 365

Leu Thr Asn Gly His Asp Gly Ser Trp Val Ala His Pro Ala Leu Ala
370                 375                 380

Pro Ile Cys Asn Glu Val Phe Ile Asn Met Gly Thr Pro Asn Gln Ile
385                 390                 395                 400

Tyr Phe Ile Pro Glu Asn Val Val Thr Ala Ala Asn Leu Leu Glu Thr
                405                 410                 415

Lys Ile Pro Asn Gly Glu Ile Thr Glu Gly Ile Val Gln Asn Leu
            420                 425                 430

Asp Ile Gly Leu Gln Tyr Met Glu Ala Trp Leu Arg Gly Ser Gly Cys
            435                 440                 445

Val Pro Ile Asn Asn Leu Met Glu Asp Ala Ala Thr Ala Glu Val Ser
450                 455                 460
```

```
Arg Cys Gln Leu Tyr Gln Trp Val Lys His Gly Val Thr Leu Lys Asp
465                 470                 475                 480

Thr Gly Glu Lys Val Thr Pro Glu Leu Thr Glu Lys Ile Leu Lys Glu
            485                 490                 495

Gln Val Glu Arg Leu Ser Lys Ala Ser Pro Leu Gly Asp Lys Asn Lys
        500                 505                 510

Phe Ala Leu Ala Ala Lys Tyr Phe Leu Pro Glu Ile Arg Gly Glu Lys
            515                 520                 525

Phe Ser Glu Phe Leu Thr Thr Leu Leu Tyr Asp Glu Ile Val Ser Thr
        530                 535                 540

Lys Ala Thr Pro Thr Asp Leu
545                 550

<210> SEQ ID NO 19
<211> LENGTH: 416
<212> TYPE: PRT
<213> ORGANISM: Aspergillus niger

<400> SEQUENCE: 19

Met Asn Val Glu Thr Ser Leu Pro Gly Ser Gly Ser Asp Leu Glu
1               5                   10                  15

Thr Phe His His Glu Thr Lys Lys His Ala Asn His Asp Ser Gly Ile
                20                  25                  30

Ser Val Asn His Glu Ala Glu Ile Gly Val Asn His Thr Phe Glu Lys
            35                  40                  45

Pro Gly Pro Val Gly Ile Arg Glu Arg Leu Arg His Phe Thr Trp Ala
        50                  55                  60

Trp Tyr Thr Leu Thr Met Ser Cys Gly Gly Leu Ala Leu Leu Ile Val
65                  70                  75                  80

Asn Gln Pro His Asp Phe Lys Gly Leu Lys Asp Ile Ala Arg Val Val
                85                  90                  95

Tyr Cys Leu Asn Leu Ala Phe Phe Val Ile Val Thr Ser Leu Met Ala
            100                 105                 110

Ile Arg Phe Ile Leu His Lys Asn Met Trp Glu Ser Leu Gly His Asp
        115                 120                 125

Arg Glu Gly Leu Phe Phe Pro Thr Phe Trp Leu Ser Ile Ala Thr Met
    130                 135                 140

Ile Thr Gly Leu Tyr Lys Cys Phe Gly Asp Asp Ala Asn Glu Lys Phe
145                 150                 155                 160

Thr Lys Cys Leu Gln Val Leu Phe Trp Ile Tyr Cys Gly Cys Thr Met
                165                 170                 175

Ile Thr Ala Val Gly Gln Tyr Ser Phe Val Phe Ala Thr His Lys Tyr
            180                 185                 190

Glu Leu His Thr Met Met Pro Ser Trp Ile Leu Pro Ala Phe Pro Val
        195                 200                 205

Met Leu Ser Gly Thr Ile Ala Ser Val Ile Gly Ser Gly Gln Pro Ala
    210                 215                 220

Ser Asp Gly Ile Pro Ile Ile Ala Gly Ile Thr Phe Gln Gly Leu
225                 230                 235                 240

Gly Phe Ser Ile Ser Phe Met Tyr Ala His Tyr Ile Gly Arg Leu
                245                 250                 255

Met Glu Val Gly Leu Pro Ser Pro Glu His Arg Pro Gly Met Phe Ile
            260                 265                 270

Cys Val Gly Pro Pro Ala Phe Thr Ala Leu Ala Leu Val Gly Met Ala
        275                 280                 285
```

```
Lys Ala Leu Pro Asp Asp Phe Gln Ile Val Gly Asp Pro His Ala Val
        290                 295                 300

Ile Asp Gly Arg Val Met Leu Phe Leu Ala Val Ser Ala Ala Ile Phe
305                 310                 315                 320

Leu Trp Ala Leu Ser Phe Trp Phe Phe Cys Ile Ala Val Val Ala Val
                325                 330                 335

Val Arg Ser Pro Pro Lys Gly Phe His Leu Asn Trp Phe Ala Met Val
            340                 345                 350

Phe Pro Asn Thr Gly Phe Thr Leu Ala Thr Ile Thr Leu Ala Asn Met
            355                 360                 365

Phe Glu Ser Pro Gly Val Lys Gly Val Ala Thr Ala Met Ser Leu Cys
370                 375                 380

Val Ile Ile Met Phe Ile Phe Val Leu Val Ser Ala Ile Arg Ala Val
385                 390                 395                 400

Ile Arg Lys Asp Ile Met Trp Pro Gly Gln Asp Glu Asp Val Ser Glu
                405                 410                 415

<210> SEQ ID NO 20
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /organism="Artificial Sequence"
      /note="Primer 7"
      /mol_type="unassigned DNA"

<400> SEQUENCE: 20
attgacgagg agttccacta cg                                           22

<210> SEQ ID NO 21
<211> LENGTH: 77
<212> TYPE: DNA
<213> ORGANISM: Artificial Sequence
<220> FEATURE:
<221> NAME/KEY: source
<222> LOCATION: 1..77
<223> OTHER INFORMATION: /organism="Artificial Sequence"
      /note="Primer 8"
      /mol_type="unassigned DNA"

<400> SEQUENCE: 21
taaatataac ttcgtatagc atacattata cgaacggtac tcgaggtcga atattagtac   60
gtatttagtc ttgtagc                                                 77

<210> SEQ ID NO 22
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /organism="Artificial Sequence"
      /note="Primer 9"
      /mol_type="unassigned DNA"

<400> SEQUENCE: 22
gcaatttcgg ctatacgtaa c                                            21

<210> SEQ ID NO 23
<211> LENGTH: 21
<212> TYPE: DNA
<213> ORGANISM: Artificial Sequence
```

```
<220> FEATURE:
<221> NAME/KEY: source
<222> LOCATION: 1..21
<223> OTHER INFORMATION: /organism="Artificial Sequence"
      /note="Primer 10"
      /mol_type="unassigned DNA"

<400> SEQUENCE: 23
cgttcactca tggaaaatag c                                              21

<210> SEQ ID NO 24
<211> LENGTH: 70
<212> TYPE: DNA
<213> ORGANISM: Artificial Sequence
<220> FEATURE:
<221> NAME/KEY: source
<222> LOCATION: 1..70
<223> OTHER INFORMATION: /organism="Artificial Sequence"
      /note="Primer 11"
      /mol_type="unassigned DNA"

<400> SEQUENCE: 24
ttgaccgtgc tattgccatc actgctacaa gactaaatac gtactaatat tcgacctcga    60
gtaccgttcg                                                           70

<210> SEQ ID NO 25
<211> LENGTH: 71
<212> TYPE: DNA
<213> ORGANISM: Artificial Sequence
<220> FEATURE:
<221> NAME/KEY: source
<222> LOCATION: 1..71
<223> OTHER INFORMATION: /organism="Artificial Sequence"
      /note="Primer 12"
      /mol_type="unassigned DNA"

<400> SEQUENCE: 25
tattactctt gtgaatgtta tctttgtcac ccttaactat catgatcgat cggatcctac    60
cgttcgtata g                                                         71

<210> SEQ ID NO 26
<211> LENGTH: 79
<212> TYPE: DNA
<213> ORGANISM: Artificial Sequence
<220> FEATURE:
<221> NAME/KEY: source
<222> LOCATION: 1..79
<223> OTHER INFORMATION: /organism="Artificial Sequence"
      /note="Primer 13"
      /mol_type="unassigned DNA"

<400> SEQUENCE: 26
ggccggtaca taacttcgta taatgtatgc tatacgaacg gtaggatccg atcgatcatg    60
atagttaagg gtgacaaag                                                 79

<210> SEQ ID NO 27
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /organism="Artificial Sequence"
      /note="Primer 14"
      /mol_type="unassigned DNA"
```

<400> SEQUENCE: 27
tgttgggtgg tagtgggaag ag                                          22

<210> SEQ ID NO 28
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /organism="Artificial Sequence"
      /note="Primer 15"
      /mol_type="unassigned DNA"

<400> SEQUENCE: 28
tgtctcaaga tttcggcgtc tg                                          22

<210> SEQ ID NO 29
<211> LENGTH: 77
<212> TYPE: DNA
<213> ORGANISM: Artificial Sequence
<220> FEATURE:
<221> NAME/KEY: source
<222> LOCATION: 1..77
<223> OTHER INFORMATION: /organism="Artificial Sequence"
      /note="Primer 16"
      /mol_type="unassigned DNA"

<400> SEQUENCE: 29
taaatataac ttcgtatagc atacattata cgaacggtac tcgaggtcga ctatacgaat    60
ggcaagtacg gtggttg                                                   77

<210> SEQ ID NO 30
<211> LENGTH: 76
<212> TYPE: DNA
<213> ORGANISM: Artificial Sequence
<220> FEATURE:
<221> NAME/KEY: source
<222> LOCATION: 1..76
<223> OTHER INFORMATION: /organism="Artificial Sequence"
      /note="Primer 17"
      /mol_type="unassigned DNA"

<400> SEQUENCE: 30
ggccggtaca taacttcgta taatgtatgc tatacgaacg gtaggatccg tccttgtttt    60
atatattcat tgttcc                                                    76

<210> SEQ ID NO 31
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /organism="Artificial Sequence"
      /note="Primer 18"
      /mol_type="unassigned DNA"

<400> SEQUENCE: 31
gacaacaacg gcaacttcac                                             20

<210> SEQ ID NO 32
<211> LENGTH: 70
<212> TYPE: DNA
<213> ORGANISM: Artificial Sequence

```
<220> FEATURE:
<221> NAME/KEY: source
<222> LOCATION: 1..70
<223> OTHER INFORMATION: /organism="Artificial Sequence"
      /note="Primer 19"
      /mol_type="unassigned DNA"

<400> SEQUENCE: 32
ggaacatagt agaaagacaa aaacaaccac cgtacttgcc attcgtatag tcgacctcga     60
gtaccgttcg                                                           70

<210> SEQ ID NO 33
<211> LENGTH: 71
<212> TYPE: DNA
<213> ORGANISM: Artificial Sequence
<220> FEATURE:
<221> NAME/KEY: source
<222> LOCATION: 1..71
<223> OTHER INFORMATION: /organism="Artificial Sequence"
      /note="Primer 20"
      /mol_type="unassigned DNA"

<400> SEQUENCE: 33
tcatcattta aaaatgttat tctcttgtat ctatttctac tagatagatg cggatcctac     60
cgttcgtata g                                                         71

<210> SEQ ID NO 34
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /organism="Artificial Sequence"
      /note="Primer 21"
      /mol_type="unassigned DNA"

<400> SEQUENCE: 34
atcttccggt gagatcttcc                                                 20

<210> SEQ ID NO 35
<211> LENGTH: 77
<212> TYPE: DNA
<213> ORGANISM: Artificial Sequence
<220> FEATURE:
<221> NAME/KEY: source
<222> LOCATION: 1..77
<223> OTHER INFORMATION: /organism="Artificial Sequence"
      /note="Primer 22"
      /mol_type="unassigned DNA"

<400> SEQUENCE: 35
taaatataac ttcgtatagc atacattata cgaacggtac tcgaggtcga tattattggt     60
taatttttta tttgctc                                                   77

<210> SEQ ID NO 36
<211> LENGTH: 79
<212> TYPE: DNA
<213> ORGANISM: Artificial Sequence
<220> FEATURE:
<221> NAME/KEY: source
<222> LOCATION: 1..79
<223> OTHER INFORMATION: /organism="Artificial Sequence"
      /note="Primer 23"
      /mol_type="unassigned DNA"
```

-continued

<400> SEQUENCE: 36
ggccggtaca taacttcgta taatgtatgc tatacgaacg gtaggatccg catctatcta    60
gtagaaatag atacaagag                                                 79

<210> SEQ ID NO 37
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /organism="Artificial Sequence"
      /note="Priimer 24"
      /mol_type="unassigned DNA"

<400> SEQUENCE: 37
ttcagtcgag gcatgaagtg                                                20

<210> SEQ ID NO 38
<211> LENGTH: 70
<212> TYPE: DNA
<213> ORGANISM: Artificial Sequence
<220> FEATURE:
<221> NAME/KEY: source
<222> LOCATION: 1..70
<223> OTHER INFORMATION: /organism="Artificial Sequence"
      /note="Primer 25"
      /mol_type="unassigned DNA"

<400> SEQUENCE: 38
agcatcataa tattgactta ttagagcaaa taaaaaatta accaataata tcgacctcga    60
gtaccgttcg                                                           70

<210> SEQ ID NO 39
<211> LENGTH: 71
<212> TYPE: DNA
<213> ORGANISM: Artificial Sequence
<220> FEATURE:
<221> NAME/KEY: source
<222> LOCATION: 1..71
<223> OTHER INFORMATION: /organism="Artificial Sequence"
      /note="Primer 26"
      /mol_type="unassigned DNA"

<400> SEQUENCE: 39
aacaaaactg atcatcattt aaaaatgtta ttctcttgta tctatttcta cggatcctac    60
cgttcgtata g                                                         71

<210> SEQ ID NO 40
<211> LENGTH: 560
<212> TYPE: PRT
<213> ORGANISM: Saccharomyces cerevisiae
<220> FEATURE:
<223> OTHER INFORMATION: NDE1

<400> SEQUENCE: 40

Met Ile Arg Gln Ser Leu Met Lys Thr Val Trp Ala Asn Ser Ser Arg
1               5                   10                  15

Phe Ser Leu Gln Ser Lys Ser Gly Leu Val Lys Tyr Ala Lys Asn Arg
            20                  25                  30

Ser Phe His Ala Ala Arg Asn Leu Leu Glu Asp Lys Lys Val Ile Leu
        35                  40                  45

Gln Lys Val Ala Pro Thr Thr Gly Val Val Ala Lys Gln Ser Phe Phe
    50                  55                  60

```
Lys Arg Thr Gly Lys Phe Thr Leu Lys Ala Leu Leu Tyr Ser Ala Leu
 65                  70                  75                  80

Ala Gly Thr Ala Tyr Val Ser Tyr Ser Leu Tyr Arg Glu Ala Asn Pro
                 85                  90                  95

Ser Thr Gln Val Pro Gln Ser Asp Thr Phe Pro Asn Gly Ser Lys Arg
            100                 105                 110

Lys Thr Leu Val Ile Leu Gly Ser Gly Trp Gly Ser Val Ser Leu Leu
        115                 120                 125

Lys Asn Leu Asp Thr Thr Leu Tyr Asn Val Val Val Ser Pro Arg
130                 135                 140

Asn Tyr Phe Leu Phe Thr Pro Leu Leu Pro Ser Thr Pro Val Gly Thr
145                 150                 155                 160

Ile Glu Leu Lys Ser Ile Val Glu Pro Val Arg Thr Ile Ala Arg Arg
                165                 170                 175

Ser His Gly Glu Val His Tyr Tyr Glu Ala Glu Ala Tyr Asp Val Asp
            180                 185                 190

Pro Glu Asn Lys Thr Ile Lys Val Lys Ser Ser Ala Lys Asn Asn Asp
        195                 200                 205

Tyr Asp Leu Asp Leu Lys Tyr Asp Tyr Leu Val Val Gly Val Gly Ala
210                 215                 220

Gln Pro Asn Thr Phe Gly Thr Pro Gly Val Tyr Glu Tyr Ser Ser Phe
225                 230                 235                 240

Leu Lys Glu Ile Ser Asp Ala Gln Glu Ile Arg Leu Lys Ile Met Ser
                245                 250                 255

Ser Ile Glu Lys Ala Ala Ser Leu Ser Pro Lys Asp Pro Glu Arg Ala
            260                 265                 270

Arg Leu Leu Ser Phe Val Val Gly Gly Pro Thr Gly Val Glu
        275                 280                 285

Phe Ala Ala Glu Leu Arg Asp Tyr Val Asp Gln Asp Leu Arg Lys Trp
290                 295                 300

Met Pro Glu Leu Ser Lys Glu Ile Lys Val Thr Leu Val Glu Ala Leu
305                 310                 315                 320

Pro Asn Ile Leu Asn Met Phe Asp Lys Tyr Leu Val Asp Tyr Ala Gln
                325                 330                 335

Asp Leu Phe Lys Glu Glu Lys Ile Asp Leu Arg Leu Lys Thr Met Val
            340                 345                 350

Lys Lys Val Asp Ala Thr Thr Ile Thr Ala Lys Thr Gly Asp Gly Asp
        355                 360                 365

Ile Glu Asn Ile Pro Tyr Gly Val Leu Val Trp Ala Thr Gly Asn Ala
370                 375                 380

Pro Arg Glu Val Ser Lys Asn Leu Met Thr Lys Leu Glu Glu Gln Asp
385                 390                 395                 400

Ser Arg Arg Gly Leu Leu Ile Asp Asn Lys Leu Gln Leu Leu Gly Ala
                405                 410                 415

Lys Gly Ser Ile Phe Ala Ile Gly Asp Cys Thr Phe His Pro Gly Leu
            420                 425                 430

Phe Pro Thr Ala Gln Val Ala His Gln Glu Gly Glu Tyr Leu Ala Gln
        435                 440                 445

Tyr Phe Lys Lys Ala Tyr Lys Ile Asp Gln Leu Asn Trp Lys Met Thr
450                 455                 460

His Ala Lys Asp Asp Ser Glu Val Ala Arg Leu Lys Asn Gln Ile Val
465                 470                 475                 480
```

```
Lys Thr Gln Ser Gln Ile Glu Asp Phe Lys Tyr Asn His Lys Gly Ala
                485                 490                 495

Leu Ala Tyr Ile Gly Ser Asp Lys Ala Ile Ala Asp Leu Ala Val Gly
            500                 505                 510

Glu Ala Lys Tyr Arg Leu Ala Gly Ser Phe Thr Phe Leu Phe Trp Lys
        515                 520                 525

Ser Ala Tyr Leu Ala Met Cys Leu Ser Phe Arg Asn Arg Val Leu Val
    530                 535                 540

Ala Met Asp Trp Ala Lys Val Tyr Phe Leu Gly Arg Asp Ser Ser Ile
545                 550                 555                 560
```

<210> SEQ ID NO 41
<211> LENGTH: 545
<212> TYPE: PRT
<213> ORGANISM: Saccharomyces cerevisiae
<220> FEATURE:
<223> OTHER INFORMATION: NDE2

<400> SEQUENCE: 41

```
Met Leu Pro Arg Leu Gly Phe Ala Arg Thr Ala Arg Ser Ile His Arg
1               5                   10                  15

Phe Lys Met Thr Gln Ile Ser Lys Pro Phe Phe His Ser Thr Glu Val
            20                  25                  30

Gly Lys Pro Gly Pro Gln Gln Lys Leu Ser Lys Ser Tyr Thr Ala Val
        35                  40                  45

Phe Lys Lys Trp Phe Val Arg Gly Leu Lys Leu Thr Phe Tyr Thr Thr
    50                  55                  60

Leu Ala Gly Thr Leu Tyr Val Ser Tyr Glu Leu Tyr Lys Glu Ser Asn
65                  70                  75                  80

Pro Pro Lys Gln Val Pro Gln Ser Thr Ala Phe Ala Asn Gly Leu Lys
            85                  90                  95

Lys Lys Glu Leu Val Ile Leu Gly Thr Gly Trp Gly Ala Ile Ser Leu
        100                 105                 110

Leu Lys Lys Leu Asp Thr Ser Leu Tyr Asn Val Thr Val Val Ser Pro
    115                 120                 125

Arg Ser Phe Phe Leu Phe Thr Pro Leu Leu Pro Ser Thr Pro Val Gly
    130                 135                 140

Thr Ile Glu Met Lys Ser Ile Val Glu Pro Val Arg Ser Ile Ala Arg
145                 150                 155                 160

Arg Thr Pro Gly Glu Val His Tyr Ile Glu Ala Glu Ala Leu Asp Val
            165                 170                 175

Asp Pro Lys Ala Lys Lys Val Met Val Gln Ser Val Ser Glu Asp Glu
        180                 185                 190

Tyr Phe Val Ser Ser Leu Ser Tyr Asp Tyr Leu Val Val Ser Val Gly
    195                 200                 205

Ala Lys Thr Thr Thr Phe Asn Ile Pro Gly Val Tyr Gly Asn Ala Asn
    210                 215                 220

Phe Leu Lys Glu Ile Glu Asp Ala Gln Asn Ile Arg Met Lys Leu Met
225                 230                 235                 240

Lys Thr Ile Glu Gln Ala Ser Ser Phe Pro Val Asn Asp Pro Glu Arg
            245                 250                 255

Lys Arg Leu Leu Thr Phe Val Val Val Gly Gly Gly Pro Thr Gly Val
        260                 265                 270

Glu Phe Ala Ala Glu Leu Gln Asp Tyr Ile Asn Gln Asp Leu Arg Lys
    275                 280                 285
```

```
Trp Met Pro Asp Leu Ser Lys Glu Met Lys Val Ile Leu Ile Glu Ala
            290             295             300

Leu Pro Asn Ile Leu Asn Met Phe Asp Lys Thr Leu Ile Lys Tyr Ala
305             310             315             320

Glu Asp Leu Phe Ala Arg Asp Glu Ile Asp Leu Gln Val Asn Thr Ala
                325             330             335

Val Lys Val Val Glu Pro Thr Tyr Ile Arg Thr Leu Gln Asn Gly Gln
            340             345             350

Thr Asn Thr Asp Ile Glu Tyr Gly Met Leu Val Trp Ala Thr Gly Asn
            355             360             365

Glu Pro Ile Asp Phe Ser Lys Thr Leu Met Ser Arg Ile Pro Glu Gln
370             375             380

Thr Asn Arg Arg Gly Leu Leu Ile Asn Asp Lys Leu Glu Leu Leu Gly
385             390             395             400

Ser Glu Asn Ser Ile Tyr Ala Ile Gly Asp Cys Thr Ala His Thr Gly
                405             410             415

Phe Phe Pro Thr Ala Gln Val Ala His Gln Glu Gly Glu Tyr Leu Ala
            420             425             430

Lys Ile Leu Asp Lys Lys Leu Gln Ile Glu Gln Leu Glu Trp Asp Met
            435             440             445

Leu Asn Ser Thr Asp Glu Thr Glu Val Ser Arg Leu Gln Lys Glu Val
450             455             460

Asn Leu Arg Lys Ser Lys Leu Asp Lys Phe Asn Tyr Lys His Met Gly
465             470             475             480

Ala Leu Ala Tyr Ile Gly Ser Glu Thr Ala Ile Ala Asp Leu His Met
                485             490             495

Gly Asp Ser Ser Tyr Gln Leu Lys Gly Met Phe Ala Phe Leu Phe Trp
            500             505             510

Lys Ser Ala Tyr Leu Ala Met Cys Leu Ser Ile Arg Asn Arg Ile Leu
            515             520             525

Ile Ala Met Asp Trp Thr Lys Val Tyr Phe Leu Gly Arg Asp Ser Ser
            530             535             540

Val
545

<210> SEQ ID NO 42
<211> LENGTH: 649
<212> TYPE: PRT
<213> ORGANISM: Saccharomyces cerevisiae
<220> FEATURE:
<223> OTHER INFORMATION: GUT2

<400> SEQUENCE: 42

Met Phe Ser Val Thr Arg Arg Arg Ala Ala Gly Ala Ala Ala Ala Met
1               5                   10                  15

Ala Thr Ala Thr Gly Thr Leu Tyr Trp Met Thr Ser Gln Gly Asp Arg
            20                  25                  30

Pro Leu Val His Asn Asp Pro Ser Tyr Met Val Gln Phe Pro Thr Ala
        35                  40                  45

Ala Pro Pro Gln Val Ser Arg Arg Asp Leu Leu Asp Arg Leu Ala Lys
    50                  55                  60

Thr His Gln Phe Asp Val Leu Ile Ile Gly Gly Ala Thr Gly Thr
65                  70                  75                  80

Gly Cys Ala Leu Asp Ala Ala Thr Arg Gly Leu Asn Val Ala Leu Val
                85                  90                  95
```

-continued

Glu Lys Gly Asp Phe Ala Ser Gly Thr Ser Ser Lys Ser Thr Lys Met
                100                 105                 110
Ile His Gly Gly Val Arg Tyr Leu Glu Lys Ala Phe Trp Glu Phe Ser
            115                 120                 125
Lys Ala Gln Leu Asp Leu Val Ile Glu Ala Leu Asn Glu Arg Lys His
        130                 135                 140
Leu Ile Asn Thr Ala Pro His Leu Cys Thr Val Leu Pro Ile Leu Ile
145                 150                 155                 160
Pro Ile Tyr Ser Thr Trp Gln Val Pro Tyr Ile Tyr Met Gly Cys Lys
                165                 170                 175
Phe Tyr Asp Phe Phe Ala Gly Ser Gln Asn Leu Lys Lys Ser Tyr Leu
            180                 185                 190
Leu Ser Lys Ser Ala Thr Val Glu Lys Ala Pro Met Leu Thr Thr Asp
        195                 200                 205
Asn Leu Lys Ala Ser Leu Val Tyr His Asp Gly Ser Phe Asn Asp Ser
210                 215                 220
Arg Leu Asn Ala Thr Leu Ala Ile Thr Ala Val Glu Asn Gly Ala Thr
225                 230                 235                 240
Val Leu Asn Tyr Val Glu Val Gln Lys Leu Ile Lys Asp Pro Thr Ser
                245                 250                 255
Gly Lys Val Ile Gly Ala Glu Ala Arg Asp Val Glu Thr Asn Glu Leu
            260                 265                 270
Val Arg Ile Asn Ala Lys Cys Val Val Asn Ala Thr Gly Pro Tyr Ser
        275                 280                 285
Asp Ala Ile Leu Gln Met Asp Arg Asn Pro Ser Gly Leu Pro Asp Ser
        290                 295                 300
Pro Leu Asn Asp Asn Ser Lys Ile Lys Ser Thr Phe Asn Gln Ile Ala
305                 310                 315                 320
Val Met Asp Pro Lys Met Val Ile Pro Ser Ile Gly Val His Ile Val
                325                 330                 335
Leu Pro Ser Phe Tyr Cys Pro Lys Asp Met Gly Leu Leu Asp Val Arg
            340                 345                 350
Thr Ser Asp Gly Arg Val Met Phe Phe Leu Pro Trp Gln Gly Lys Val
        355                 360                 365
Leu Ala Gly Thr Thr Asp Ile Pro Leu Lys Gln Val Pro Glu Asn Pro
370                 375                 380
Met Pro Thr Glu Ala Asp Ile Gln Asp Ile Leu Lys Glu Leu Gln His
385                 390                 395                 400
Tyr Ile Glu Phe Pro Val Lys Arg Glu Asp Val Leu Ser Ala Trp Ala
                405                 410                 415
Gly Val Arg Pro Leu Val Arg Asp Pro Arg Thr Ile Pro Ala Asp Gly
            420                 425                 430
Lys Lys Gly Ser Ala Thr Gln Gly Val Val Arg Ser His Phe Leu Phe
        435                 440                 445
Thr Ser Asp Asn Gly Leu Ile Thr Ile Ala Gly Gly Lys Trp Thr Thr
450                 455                 460
Tyr Arg Gln Met Ala Glu Glu Thr Val Asp Lys Val Val Glu Val Gly
465                 470                 475                 480
Gly Phe His Asn Leu Lys Pro Cys His Thr Arg Asp Ile Lys Leu Ala
                485                 490                 495
Gly Ala Glu Glu Trp Thr Gln Asn Tyr Val Ala Leu Leu Ala Gln Asn
            500                 505                 510

Tyr His Leu Ser Ser Lys Met Ser Asn Tyr Leu Val Gln Asn Tyr Gly
          515                 520                 525

Thr Arg Ser Ser Ile Ile Cys Glu Phe Phe Lys Glu Ser Met Glu Asn
    530                 535                 540

Lys Leu Pro Leu Ser Leu Ala Asp Lys Glu Asn Asn Val Ile Tyr Ser
545                 550                 555                 560

Ser Glu Glu Asn Asn Leu Val Asn Phe Asp Thr Phe Arg Tyr Pro Phe
                565                 570                 575

Thr Ile Gly Glu Leu Lys Tyr Ser Met Gln Tyr Glu Tyr Cys Arg Thr
            580                 585                 590

Pro Leu Asp Phe Leu Leu Arg Arg Thr Arg Phe Ala Phe Leu Asp Ala
        595                 600                 605

Lys Glu Ala Leu Asn Ala Val His Ala Thr Val Lys Val Met Gly Asp
    610                 615                 620

Glu Phe Asn Trp Ser Glu Lys Lys Arg Gln Trp Glu Leu Glu Lys Thr
625                 630                 635                 640

Val Asn Phe Ile Lys Thr Phe Gly Val
                645

<210> SEQ ID NO 43
<211> LENGTH: 4946
<212> TYPE: DNA
<213> ORGANISM: Artificial Sequence
<220> FEATURE:
<221> NAME/KEY: source
<222> LOCATION: 1..4946
<223> OTHER INFORMATION: /organism="Artificial Sequence"
      /note="pSUC227"
      /mol_type="unassigned DNA"

<400> SEQUENCE: 43

```
aaatgacatg gaggcccaga ataccctcct tgacagtctt gacgtgcgca gctcaggggc      60
atgatgtgac tgtcgcccgt acatttagcc catacatccc catgtataat catttgcatc     120
catacatttt gatggccgca cggcgcgaag caaaaattac ggctcctcgc tgcagacctg     180
cgagcaggga acgctccccc tcacagacgc gttgaattgt ccccacgccg cgccctgta     240
gagaaatata aaaggttagg atttgccact gaggttcttc tttctatatac ttcctttttaa     300
aatcttgcta ggatacagtt ctcacatcac atccgaacat aaacaaccat gggtaaggaa     360
aagactcacg tttcgaggcc gcgattaaat tccaacatgg atgctgattt atatgggtat     420
aaatgggctc gcgataatgt cgggcaatca ggtgcgacaa tctatcgatt gtatgggaag     480
cccgatgcgc cagagttgtt tctgaaacat ggcaaaggta gcgttgccaa tgatgttaca     540
gatgagatgg tcagactaaa ctggctgacg gaatttatgc ctcttccgac catcaagcat     600
tttatccgta ctcctgatga tgcatggtta ctcaccactg cgatcccggg caaaacagca     660
ttccaggtat tagaagaata tcctgattca ggtgaaaata ttgttgatgc gctggcagtg     720
ttcctgcgcc ggttgcattc gattcctgtt tgtaattgtc cttttaacag cgatcgcgta     780
tttcgtctcg ctcaggcgca atcacgaatg aataacggtt tggttgatgc gagtgatttt     840
gatgacgagc gtaatggctg gcctgttgaa caagtctgga agaaaatgca taagcttttg     900
ccattctcac cggattcagt cgtcactcat ggtgatttct cacttgataa ccttatttt     960
gacgagggga aattaatagg ttgtattgat gttggacgag tcggaatcgc agaccgatac    1020
caggatcttg ccatcctatg gaactgcctc ggtgagtttt ctccttcatt acagaaacgg    1080
ctttttcaaa aatatggtat tgataatcct gatatgaata aattgcagtt tcatttgatg    1140
```

```
ctcgatgagt ttttctaatc agtactgaca ataaaaagat tcttgttttc aagaacttgt   1200
catttgtata gttttttttat attgtagttg ttctatttta atcaaatgtt agcgtgattt   1260 atatttttt tcgcctcgac atcatctgcc cagatgcgaa gttaagtgcg cagaaagtaa    1320
tatcatgcgt caatcgtatg tgaatgctgg tcgctatact gatttaaata taacttcgta   1380
tagcatacat tatacgaacg gtactcgagg tcgacgggcc ccagctgggc gccaggcctg   1440
cggccgcggc gcgccgagct catggcgcgc ctaggccttg acggccttcc gccaattcgc   1500
cctatagtga gtcgtattac gtcgcgctca ctggccgtcg ttttacaacg tcgtgactgg   1560
gaaaaccctg gcgttaccca acttaatcgc cttgcagcac atcccccttt cgccagctgg   1620
cgtaatagcg aagaggcccg caccgaaacg cccttcccaa cagttgcgca gcctgaatgg   1680
cgaatgggag cgccctgtag cggccactca accctatctc ggtctattct tttgatttat   1740
aagggatttt gccgatttcg gcctattggt taaaaaatga gctgatttaa caaaaattta   1800
acgcgaattt taacaaaata ttaacgctta caatttaggt ggcactttc ggggaaatgt    1860 gcgcggaacc cctatttgtt tatttttcta aatacattca aatatgtatc cgctcatgag   1920
acaataaccc tgataaatgc ttcaataata ttgaaaaagg aagagtatga gtattcaaca   1980
tttccgtgtc gcccttattc cctttttttgc ggcattttgc cttcctgttt ttgctcaccc   2040
agaaacgctg gtgaaagtaa aagatgctga agatcagttg ggtgcacgag tgggttacat   2100
cgaactggat ctcaacagcg gtaagatcct tgagagtttt cgccccgaag aacgttttcc   2160
aatgatgagc acttttaaag ttctgctatg tggcgcggta ttatcccgta ttgacgccgg   2220
gcaagagcaa ctcggtcgcc gcatacacta ttctcagaat gacttggttg agtactcacc   2280
agtcacagaa aagcatctta cggatggcat gacagtaaga gaattatgca gtgctgccat   2340
aaccatgagt gataacactg cggccaactt acttctgaca acgatcggag gaccgaagga   2400
gctaaccgct tttttgcaca acatggggga tcatgtaact cgccttgatc gttgggaacc   2460
ggagctgaat gaagccatac caaacgacga gcgtgacacc acgatgcctg tagcaatggc   2520
aacaacgttg cgcaaactat taactggcga actacttact ctagcttccc ggcaacaatt   2580
aatagactgg atggaggcgg ataaagttgc aggaccactt ctgcgctcgg cccttccggc   2640
tggctggttt attgctgata aatctggagc cggtgagcgt ggttctcgcg gtatcattgc   2700
agcactgggg ccagatggta agccctcccg tatcgtagtt atctacacga cggggagtca   2760
ggcaactatg gatgaacgaa atagacagat cgctgagata ggtgcctcac tgattaagca   2820
ttggtaactg tcagaccaag tttactcata tatactttag attgatttaa aacttcattt   2880
ttaatttaaa aggatctagg tgaagatcct ttttgataat ctcatgacca aaatccctta   2940
acgtgagttt tcgttccact gagcgtcaga ccccgtagaa aagatcaaag gatcttcttg   3000
agatcctttt tttctgcgcg taatctgctg cttgcaaaca aaaaaaccac cgctaccagc   3060
ggtggtttgt ttgccggatc aagagctacc aactctttt ccgaaggtaa ctggcttcag    3120
cagagcgcag ataccaaata ctgttcttct agtgtagccg tagttaggcc accacttcaa   3180
gaactctgta gcaccgccta catacctcgc tctgctaatc ctgttaccag tggctgctgc   3240
cagtggcgat aagtcgtgtc ttaccgggtt ggactcaaga cgatagttac cggataaggc   3300
gcagcggtcg ggctgaacgg ggggttcgtg cacacagccc agcttggagc gaacgaccta   3360
caccgaactg agatacctac agcgtgagct atgagaaagc gccacgcttc ccgaagggag   3420
aaaggcggac aggtatccgg taagcggcag ggtcggaaca ggagagcgca cgagggagct   3480
tccaggggga aacgcctggt atctttatag tcctgtcggg tttcgccacc tctgacttga   3540
```

```
gcgtcgattt ttgtgatgct cgtcaggggg gcggagccta tggaaaaacg ccagcaacgc      3600
ggccttttta cggttcctgg cctttttgctg gccttttgct cattaggcac cccaggcttt     3660
acccgaacga ccgagcgcag cgagtcagtg agcgaggaag cggagagcgc ccaatacgca      3720
aggaaacagc tatgaccatg ttaatgcagc tggcacgaca ggtttcccga ctggaaagcg      3780
ggcagtgagc ggaaggccca tgaggccagt taattaagag gtaccggcgc gccgcaattt     3840
cggctatacg taacagggtg ttataagcaa tccccagaaa tgccagatta cgtatatcct     3900
ggcagcgatc gctattttcc atgagtgaac gaacctggtc gaaatcagtg cgttcgaacg     3960
ctagagcctg ttttgcacgt tcaccggcat caacgttttc ttttcggatc cgccgcataa     4020
ccagtgaaac agcattgctg tcacttggtc gtggcagccc ggaccgacga tgaagcatgt     4080
ttagctggcc caaatgttgc tggatagttt ttactgccag accgcgcgcc tgaagatata     4140
gaagataatc gcgaacatct tcaggttctg cgggaaacca tttccggtta ttcaacttgc     4200
accatgccgc ccacgaccgg caaacggaca gaagcatttt ccaggtatgc tcagaaaacg     4260
cctggcgatc cctgaacatg tccatcaggt tcttgcgaac ctcatcactc gttgcatcga     4320
ccggtaatgc aggcaaattt tggtgtacgg tcagtaaatt ggacatttaa cactcagata     4380
atggttttaa gtaaagtgta caggatcggc tctgcccctc gacggtatcg ataagcttga     4440
tatcgaattc ctgcagcccg ggggatccac tagttctaga atccggggtt ttttctcctt     4500
gacgttaaag tatagaggta tattaacaat ttttttgttga tactttttatt acatttgaat    4560 aagaagtaat acaaaccgaa atgttgaaa gtattagtta aagtggttat gcagttttg       4620 catttatata tctgttaata gatcaaaaat catcgcttcg ctgattaatt accccagaaa     4680
taaggctaaa aaactaatcg cattatcatc ctatggttgt taatttgatt cgttcatttg    4740
aaggtttgtg gggccaggtt actgccaatt tttcctcttc ataaccataa aagctagtat    4800
tgtagaatct ttattgttcg gagcagtgcg gcgcgaggca catctgcgtt tcaggaacgc    4860
gaccggtgaa gacgaggacg cacggaggag agtcttcctt cggagggctg tcacccgctc    4920
ggcggcttct aatccgtact agattt                                         4946
```

<210> SEQ ID NO 44
<211> LENGTH: 3654
<212> TYPE: DNA
<213> ORGANISM: Artificial Sequence
<220> FEATURE:
<221> NAME/KEY: source
<222> LOCATION: 1..3654
<223> OTHER INFORMATION: /organism="Artificial Sequence"
    /note="pSUC225"
    /mol_type="unassigned DNA"

<400> SEQUENCE: 44

```
ctaaattgta agcgttaata ttttgttaaa attcgcgtta aattttgtt aaatcagctc      60 attttttaac caataggccg aaatcggcaa atcccttat aaatcaaaag aatagaccga     120
gatagggttg agtggccgct acagggcgct cccattcgcc attcaggctg cgcaactgtt    180
gggaagggcg tttcggtgcg ggcctcttcg ctattacgcc agctggcgaa aggggatgt     240 gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggcctaggc gcgccatgag ctcggccggc cttcgttcac tcatggaaaa tagcgatcgc    420
tgccaggata tacgtaatct ggcatttctg gggattgctt ataacaccct gttacgtata    480
gccgaaattg ccaggatcag ggttaaagat atctcacgta ctgacggtgg gagaatgtta    540
```

```
atccatattg gcagaacgaa aacgctggtt agcaccgcag gtgtagagaa ggcacttagc    600
ctggggtaa  ctaaactggt cgagcgatgg atttccgtct ctggtgtagc tgatgatccg   660
aataactacc tgttttgccg ggtcagaaaa aatggtgttg ccgcgccatc tgccaccagc    720
cagctatcaa ctcgcgccct ggaagggatt tttgaagcaa ctcatcgatt gatttacggc    780
gctaaggatg actctggtca gagatacctg gcctggtctg gacacagtgc ccgtgtcgga    840
gccgcgcgag atatggcccg cgctggagtt caataccgg  agatcatgca agctggtggc    900
tggaccaatg taaatattgt catgaactat atccgtaccc tggatagtga acaggggca     960
atggtgcgcc tgctggaaga tggcgattag ccattaacgc gtaaatgatt gctataatta   1020
tttgatattt atggtgacat atgagaaagg atttcaacat cgacggaaaa tatgtagtgc   1080
tgtctgtaag cactaatatt cagtcgccag ccgtcattgt cactgtaaag ctgagcgata   1140
gaatgcctga tattgactca atatccgttg cgtttcctgt caaaagtatg cgtagtgctg   1200
aacatttcgt gatgaatgcc accgaggaag aagcacggcg cggttttgct taaagtgatg   1260
tctgagtttg gcgaactctt gggtaaggtt ggaattgtcg acctcgagtc atgtaattag   1320
ttatgtcacg cttacattca cgccctcccc ccacatccgc tctaaccgaa aaggaaggag   1380
ttagacaacc tgaagtctag gtccctattt attttttat  agttatgtta gtattaagaa   1440
cgttatttat atttcaaatt tttctttttt ttctgtacag acgcgtgtac gcatgtaaca   1500
ttatactgaa aaccttgctt gagaaggttt tgggacgctc gaaggcttta atttgcggcc   1560
ggtacataac ttcgtataat gtatgctata cgaacggtag gatccgaatt cgggccccag   1620
ctgggcgcca tttaaatagg cctggcgcgc cgcggccgcg gccggccggt acctcttaat   1680
taactggcct catgggcctt ccgctcactg cccgctttcc agtcgggaaa cctgtcgtgc   1740
cagctgcatt aacatggtca tagctgtttc cttgcgtatt gggcgctctc cgcttcctcg   1800
ctcactgact cgctgcgctc ggtcgttcgg gtaaagcctg gggtgcctaa tgagcaaaag   1860
gccagcaaaa ggccaggaac cgtaaaaagg ccgcgttgct ggcgttttc  cataggctcc   1920
gcccccctga cgagcatcac aaaaatcgac gctcaagtca gaggtggcga aacccgacag   1980
gactataaag ataccaggcg tttccccctg gaagctccct cgtgcgctct cctgttccga   2040
ccctgccgct taccggatac ctgtccgcct ttctcccttc gggaagcgtg gcgctttctc   2100
atagctcacg ctgtaggtat ctcagttcgg tgtaggtcgt tcgctccaag ctgggctgtg   2160
tgcacgaacc ccccgttcag cccgaccgct gcgccttatc cggtaactat cgtcttgagt   2220
ccaacccggt aagacacgac ttatcgccac tggcagcagc cactggtaac aggattagca   2280
gagcgaggta tgtaggcggt gctacagagt tcttgaagtg gtggcctaac tacggctaca   2340
ctagaagaac agtatttggt atctgcgctc tgctgaagcc agttaccttc ggaaaaagag   2400
ttggtagctc ttgatccggc aaacaaacca ccgctggtag cggtggtttt tttgtttgca   2460
agcagcagat tacgcgcaga aaaaaaggat ctcaagaaga tcctttgatc ttttctacgg   2520
ggtctgacgc tcagtggaac gaaaactcac gttaagggat tttggtcatg agattatcaa   2580
aaaggatctt cacctagatc cttttaaatt aaaaatgaag ttttaaatca atctaaagta   2640
tatatgagta aacttggtct gacagttacc aatgcttaat cagtgaggca cctatctcag   2700
cgatctgtct atttcgttca tccatagttg cctgactccc cgtcgtgtag ataactacga   2760
tacgggaggg cttaccatct ggccccagtg ctgcaatgat accgcgagaa ccacgctcac   2820
cggctccaga tttatcagca ataaaccagc cagccggaag ggccgagcgc agaagtggtc   2880
ctgcaacttt atccgcctcc atccagtcta ttaattgttg ccgggaagct agagtaagta   2940
```

```
gttcgccagt taatagtttg cgcaacgttg ttgccattgc tacaggcatc gtggtgtcac    3000
gctcgtcgtt tggtatggct tcattcagct ccggttccca acgatcaagg cgagttacat    3060 gatccccat gttgtgcaaa aaagcggtta gctccttcgg tcctccgatc gttgtcagaa     3120
gtaagttggc cgcagtgtta tcactcatgg ttatggcagc actgcataat tctcttactg    3180
tcatgccatc cgtaagatgc ttttctgtga ctggtgagta ctcaaccaag tcattctgag    3240
aatagtgtat gcggcgaccg agttgctctt gcccggcgtc aatacgggat aataccgcgc    3300
cacatagcag aactttaaaa gtgctcatca ttggaaaacg ttcttcgggg cgaaaactct    3360
caaggatctt accgctgttg agatccagtt cgatgtaacc cactcgtgca cccaactgat    3420
cttcagcatc ttttactttc accagcgttt ctgggtgagc aaaaacagga aggcaaaatg    3480
ccgcaaaaaa gggaataagg gcgacacgga aatgttgaat actcatactc ttcctttttc    3540
aatattattg aagcatttat cagggttatt gtctcatgag cggatacata tttgaatgta    3600
tttagaaaaa taaacaaata ggggttccgc gcacatttcc ccgaaaagtg ccac          3654

<210> SEQ ID NO 45
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /organism="Artificial Sequence"
      /note="Primer 27"
      /mol_type="unassigned DNA"

<400> SEQUENCE: 45
acctatagag ccgggcagag                                                 20

<210> SEQ ID NO 46
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /organism="Artificial Sequence"
      /note="Primer 28"
      /mol_type="unassigned DNA"

<400> SEQUENCE: 46
ctttatatta tcaatatttg tgtttgtgg                                       29

<210> SEQ ID NO 47
<211> LENGTH: 70
<212> TYPE: DNA
<213> ORGANISM: Artificial Sequence
<220> FEATURE:
<221> NAME/KEY: source
<222> LOCATION: 1..70
<223> OTHER INFORMATION: /organism="Artificial Sequence"
      /note="Primer 29"
      /mol_type="unassigned DNA"

<400> SEQUENCE: 47
tatattgtac accccccccc tccacaaaca caaatattga atatataaag tcgacctcga    60
gtaccgttcg                                                            70

<210> SEQ ID NO 48
<211> LENGTH: 71
<212> TYPE: DNA
<213> ORGANISM: Artificial Sequence
```

```
<220> FEATURE:
<221> NAME/KEY: source
<222> LOCATION: 1..71
<223> OTHER INFORMATION: /organism="Artificial Sequence"
      /note="Primer 30"
      /mol_type="unassigned DNA"

<400> SEQUENCE: 48
cctcgaaaaa agtgggggaa agtatgatat gttatctttc tccaataaat cggatcctac    60
cgttcgtata g                                                        71

<210> SEQ ID NO 49
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /organism="Artificial Sequence"
      /note="Primer 31"
      /mol_type="unassigned DNA"

<400> SEQUENCE: 49
atttattgga gaaagataac atatcatac                                     29

<210> SEQ ID NO 50
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /organism="Artificial Sequence"
      /note="Primer 32"
      /mol_type="unassigned DNA"

<400> SEQUENCE: 50
tggtgtgctt gcagtcattg                                               20

<210> SEQ ID NO 51
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /organism="Artificial Sequence"
      /note="Primer 33"
      /mol_type="unassigned DNA"

<400> SEQUENCE: 51
cgcagcagca agtaactgtg ac                                            22

<210> SEQ ID NO 52
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /organism="Artificial Sequence"
      /note="Primer 34"
      /mol_type="unassigned DNA"

<400> SEQUENCE: 52
tgataaggaa ggggagcgaa gg                                            22
```

```
<210> SEQ ID NO 53
<211> LENGTH: 70
<212> TYPE: DNA
<213> ORGANISM: Artificial Sequence
<220> FEATURE:
<221> NAME/KEY: source
<222> LOCATION: 1..70
<223> OTHER INFORMATION: /organism="Artificial Sequence"
      /note="Primer 35"
      /mol_type="unassigned DNA"

<400> SEQUENCE: 53
agattcaatt ctctttccct ttccttttcc ttcgctcccc ttccttatca tcgacctcga    60
gtaccgttcg                                                           70

<210> SEQ ID NO 54
<211> LENGTH: 75
<212> TYPE: DNA
<213> ORGANISM: Artificial Sequence
<220> FEATURE:
<221> NAME/KEY: source
<222> LOCATION: 1..75
<223> OTHER INFORMATION: /organism="Artificial Sequence"
      /note="Primer 36"
      /mol_type="unassigned DNA"

<400> SEQUENCE: 54
ctgtagtaat gttactagta gtagttgtag aacttgtgta taatgataaa ttgcggatcc    60
taccgttcgt atagc                                                     75

<210> SEQ ID NO 55
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /organism="Artificial Sequence"
      /note="Primer 37"
      /mol_type="unassigned DNA"

<400> SEQUENCE: 55
cacaagttct acaactacta ctag                                           24

<210> SEQ ID NO 56
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /organism="Artificial Sequence"
      /note="Primer 38"
      /mol_type="unassigned DNA"

<400> SEQUENCE: 56
tttccttggc ggcatcgaaa tc                                             22

<210> SEQ ID NO 57
<211> LENGTH: 391
<212> TYPE: PRT
<213> ORGANISM: Saccharomyces cerevisiae
<220> FEATURE:
<223> OTHER INFORMATION: GPD1
```

<400> SEQUENCE: 57

```
Met Ser Ala Ala Ala Asp Arg Leu Asn Leu Thr Ser Gly His Leu Asn
1               5                   10                  15
Ala Gly Arg Lys Arg Ser Ser Ser Val Ser Leu Lys Ala Ala Glu
            20                  25                  30
Lys Pro Phe Lys Val Thr Val Ile Gly Ser Gly Asn Trp Gly Thr Thr
            35                  40                  45
Ile Ala Lys Val Val Ala Glu Asn Cys Lys Gly Tyr Pro Glu Val Phe
    50                  55                  60
Ala Pro Ile Val Gln Met Trp Val Phe Glu Glu Ile Asn Gly Glu
65                  70                  75                  80
Lys Leu Thr Glu Ile Ile Asn Thr Arg His Gln Asn Val Lys Tyr Leu
                85                  90                  95
Pro Gly Ile Thr Leu Pro Asp Asn Leu Val Ala Asn Pro Asp Leu Ile
            100                 105                 110
Asp Ser Val Lys Asp Val Asp Ile Ile Val Phe Asn Ile Pro His Gln
            115                 120                 125
Phe Leu Pro Arg Ile Cys Ser Gln Leu Lys Gly His Val Asp Ser His
    130                 135                 140
Val Arg Ala Ile Ser Cys Leu Lys Gly Phe Glu Val Gly Ala Lys Gly
145                 150                 155                 160
Val Gln Leu Leu Ser Ser Tyr Ile Thr Glu Glu Leu Gly Ile Gln Cys
                165                 170                 175
Gly Ala Leu Ser Gly Ala Asn Ile Ala Thr Glu Val Ala Gln Glu His
            180                 185                 190
Trp Ser Glu Thr Thr Val Ala Tyr His Ile Pro Lys Asp Phe Arg Gly
            195                 200                 205
Glu Gly Lys Asp Val Asp His Lys Val Leu Lys Ala Leu Phe His Arg
    210                 215                 220
Pro Tyr Phe His Val Ser Val Ile Glu Asp Val Ala Gly Ile Ser Ile
225                 230                 235                 240
Cys Gly Ala Leu Lys Asn Val Val Ala Leu Gly Cys Gly Phe Val Glu
                245                 250                 255
Gly Leu Gly Trp Gly Asn Asn Ala Ser Ala Ala Ile Gln Arg Val Gly
            260                 265                 270
Leu Gly Glu Ile Ile Arg Phe Gly Gln Met Phe Phe Pro Glu Ser Arg
    275                 280                 285
Glu Glu Thr Tyr Tyr Gln Glu Ser Ala Gly Val Ala Asp Leu Ile Thr
290                 295                 300
Thr Cys Ala Gly Gly Arg Asn Val Lys Val Ala Arg Leu Met Ala Thr
305                 310                 315                 320
Ser Gly Lys Asp Ala Trp Glu Cys Glu Lys Glu Leu Leu Asn Gly Gln
                325                 330                 335
Ser Ala Gln Gly Leu Ile Thr Cys Lys Glu Val His Glu Trp Leu Glu
            340                 345                 350
Thr Cys Gly Ser Val Glu Asp Phe Pro Leu Phe Glu Ala Val Tyr Gln
            355                 360                 365
Ile Val Tyr Asn Asn Tyr Pro Met Lys Asn Leu Pro Asp Met Ile Glu
    370                 375                 380
Glu Leu Asp Leu His Glu Asp
385                 390
```

<210> SEQ ID NO 58
<211> LENGTH: 392
<212> TYPE: PRT
<213> ORGANISM: Saccharomyces cerevisiae
<220> FEATURE:
<223> OTHER INFORMATION: GPD2

<400> SEQUENCE: 58

```
Met Thr Ala His Thr Asn Ile Lys Gln His Lys His Cys His Glu Asp
1               5                   10                  15

His Pro Ile Arg Arg Ser Asp Ser Ala Val Ser Ile Val His Leu Lys
            20                  25                  30

Arg Ala Pro Phe Lys Val Thr Val Ile Gly Ser Gly Asn Trp Gly Thr
        35                  40                  45

Thr Ile Ala Lys Val Ile Ala Glu Asn Thr Glu Leu His Ser His Ile
    50                  55                  60

Phe Glu Pro Glu Val Arg Met Trp Val Phe Asp Glu Lys Ile Gly Asp
65                  70                  75                  80

Glu Asn Leu Thr Asp Ile Ile Asn Thr Arg His Gln Asn Val Lys Tyr
                85                  90                  95

Leu Pro Asn Ile Asp Leu Pro His Asn Leu Val Ala Asp Pro Asp Leu
            100                 105                 110

Leu His Ser Ile Lys Gly Ala Asp Ile Leu Val Phe Asn Ile Pro His
        115                 120                 125

Gln Phe Leu Pro Asn Ile Val Lys Gln Leu Gln Gly His Val Ala Pro
    130                 135                 140

His Val Arg Ala Ile Ser Cys Leu Lys Gly Phe Glu Leu Gly Ser Lys
145                 150                 155                 160

Gly Val Gln Leu Leu Ser Ser Tyr Val Thr Asp Glu Leu Gly Ile Gln
                165                 170                 175

Cys Gly Ala Leu Ser Gly Ala Asn Leu Ala Pro Glu Val Ala Lys Glu
            180                 185                 190

His Trp Ser Glu Thr Thr Val Ala Tyr Gln Leu Pro Lys Asp Tyr Gln
        195                 200                 205

Gly Asp Gly Lys Asp Val Asp His Lys Ile Leu Lys Leu Leu Phe His
    210                 215                 220

Arg Pro Tyr Phe His Val Asn Val Ile Asp Asp Val Ala Gly Ile Ser
225                 230                 235                 240

Ile Ala Gly Ala Leu Lys Asn Val Val Ala Leu Ala Cys Gly Phe Val
                245                 250                 255

Glu Gly Met Gly Trp Gly Asn Asn Ala Ser Ala Ala Ile Gln Arg Leu
            260                 265                 270

Gly Leu Gly Glu Ile Ile Lys Phe Gly Arg Met Phe Phe Pro Glu Ser
        275                 280                 285

Lys Val Glu Thr Tyr Tyr Gln Glu Ser Ala Gly Val Ala Asp Leu Ile
    290                 295                 300

Thr Thr Cys Ser Gly Gly Arg Asn Val Lys Val Ala Thr Tyr Met Ala
305                 310                 315                 320

Lys Thr Gly Lys Ser Ala Leu Glu Ala Glu Lys Glu Leu Leu Asn Gly
                325                 330                 335

Gln Ser Ala Gln Gly Ile Ile Thr Cys Arg Glu Val His Glu Trp Leu
            340                 345                 350

Gln Thr Cys Glu Leu Thr Gln Glu Phe Pro Leu Phe Glu Ala Val Tyr
        355                 360                 365
```

Gln Ile Val Tyr Asn Asn Val Arg Met Glu Asp Leu Pro Glu Met Ile
        370                 375                 380

Glu Glu Leu Asp Ile Asp Asp Glu
385                 390

<210> SEQ ID NO 59
<211> LENGTH: 348
<212> TYPE: PRT
<213> ORGANISM: Saccharomyces cerevisiae
<220> FEATURE:
<223> OTHER INFORMATION: ADH1

<400> SEQUENCE: 59

Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Val Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

```
Val Gly Leu Ser Thr Leu Pro Glu Ile Tyr Glu Lys Met Glu Lys Gly
            325                 330                 335

Gln Ile Val Gly Arg Tyr Val Val Asp Thr Ser Lys
            340                 345

<210> SEQ ID NO 60
<211> LENGTH: 277
<212> TYPE: PRT
<213> ORGANISM: Saccharomyces cerevisiae
<220> FEATURE:
<223> OTHER INFORMATION: ADH2

<400> SEQUENCE: 60

Met Ser Ile Pro Glu Thr Gln Lys Ala Ile Ile Phe Tyr Glu Ser Asn
1               5                   10                  15

Gly Lys Leu Glu His Lys Asp Ile Pro Val Pro Lys Pro Lys Pro Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Thr Lys Leu Pro Leu Val
    50                  55                  60

Gly Gly His Glu Gly Ala Gly Val Val Val Ala Ile Gly Asp Asn Val
65                  70                  75                  80

Arg Gly Trp Lys Val Gly Asp Leu Ala Gly Ile Lys Trp Leu Asn Ser
                85                  90                  95

Ser Cys Thr Gly His Trp Val Ala Ile Ser Gly Ala Ala Gly Gly Leu
            100                 105                 110

Gly Ser Leu Ala Val Gln Tyr Ala Lys Ala Met Gly Tyr Arg Val Leu
        115                 120                 125

Gly Ile Asp Gly Gly Pro Gly Lys Glu Glu Leu Phe Thr Ser Leu Gly
    130                 135                 140

Gly Glu Val Phe Ile Asp Phe Thr Lys Glu Lys Asp Ile Val Ser Ala
145                 150                 155                 160

Val Val Lys Ala Thr Asn Gly Gly Ala His Gly Ile Ile Asn Val Ser
                165                 170                 175

Val Ser Glu Ala Ala Ile Glu Ala Ser Thr Arg Tyr Cys Arg Ala Asn
            180                 185                 190

Gly Thr Val Val Leu Val Gly Leu Pro Ala Gly Ala Lys Cys Ser Ser
        195                 200                 205

Asp Val Phe Asn His Val Val Lys Ser Ile Ser Ile Val Gly Ser Tyr
    210                 215                 220

Val Gly Asn Arg Ala Asp Thr Arg Glu Ala Leu Asp Phe Phe Ala Arg
225                 230                 235                 240

Gly Leu Val Lys Ser Pro Ile Lys Val Val Gly Leu Ser Ser Leu Pro
                245                 250                 255

Glu Ile Tyr Glu Lys Met Glu Lys Gly Gln Ile Ala Gly Arg Tyr Val
            260                 265                 270

Val Asp Thr Ser Lys
        275

<210> SEQ ID NO 61
<211> LENGTH: 375
<212> TYPE: PRT
<213> ORGANISM: Saccharomyces cerevisiae
<220> FEATURE:
<223> OTHER INFORMATION: ADH3
```

<400> SEQUENCE: 61

```
Met Leu Arg Thr Ser Thr Leu Phe Thr Arg Arg Val Gln Pro Ser Leu
1               5                   10                  15

Phe Ser Arg Asn Ile Leu Arg Leu Gln Ser Thr Ala Ala Ile Pro Lys
            20                  25                  30

Thr Gln Lys Gly Val Ile Phe Tyr Glu Asn Lys Gly Lys Leu His Tyr
        35                  40                  45

Lys Asp Ile Pro Val Pro Glu Pro Lys Pro Asn Glu Ile Leu Ile Asn
    50                  55                  60

Val Lys Tyr Ser Gly Val Cys His Thr Asp Leu His Ala Trp His Gly
65                  70                  75                  80

Asp Trp Pro Leu Pro Val Lys Leu Pro Leu Val Gly Gly His Glu Gly
                85                  90                  95

Ala Gly Val Val Val Lys Leu Gly Ser Asn Val Lys Gly Trp Lys Val
            100                 105                 110

Gly Asp Leu Ala Gly Ile Lys Trp Leu Asn Gly Ser Cys Met Thr Cys
        115                 120                 125

Glu Phe Cys Glu Ser Gly His Glu Ser Asn Cys Pro Asp Ala Asp Leu
    130                 135                 140

Ser Gly Tyr Thr His Asp Gly Ser Phe Gln Gln Phe Ala Thr Ala Asp
145                 150                 155                 160

Ala Ile Gln Ala Ala Lys Ile Gln Gln Gly Thr Asp Leu Ala Glu Val
                165                 170                 175

Ala Pro Ile Leu Cys Ala Gly Val Thr Val Tyr Lys Ala Leu Lys Glu
            180                 185                 190

Ala Asp Leu Lys Ala Gly Asp Trp Val Ala Ile Ser Gly Ala Ala Gly
        195                 200                 205

Gly Leu Gly Ser Leu Ala Val Gln Tyr Ala Thr Ala Met Gly Tyr Arg
    210                 215                 220

Val Leu Gly Ile Asp Ala Gly Glu Glu Lys Glu Lys Leu Phe Lys Lys
225                 230                 235                 240

Leu Gly Gly Glu Val Phe Ile Asp Phe Thr Lys Thr Lys Asn Met Val
                245                 250                 255

Ser Asp Ile Gln Glu Ala Thr Lys Gly Gly Pro His Gly Val Ile Asn
            260                 265                 270

Val Ser Val Ser Glu Ala Ala Ile Ser Leu Ser Thr Glu Tyr Val Arg
        275                 280                 285

Pro Cys Gly Thr Val Val Leu Val Gly Leu Pro Ala Asn Ala Tyr Val
    290                 295                 300

Lys Ser Glu Val Phe Ser His Val Val Lys Ser Ile Asn Ile Lys Gly
305                 310                 315                 320

Ser Tyr Val Gly Asn Arg Ala Asp Thr Arg Glu Ala Leu Asp Phe Phe
                325                 330                 335

Ser Arg Gly Leu Ile Lys Ser Pro Ile Lys Ile Val Gly Leu Ser Glu
            340                 345                 350

Leu Pro Lys Val Tyr Asp Leu Met Glu Lys Gly Lys Ile Leu Gly Arg
        355                 360                 365

Tyr Val Val Asp Thr Ser Lys
    370                 375
```

<210> SEQ ID NO 62
<211> LENGTH: 382
<212> TYPE: PRT
<213> ORGANISM: Saccharomyces cerevisiae

<220> FEATURE:
<223> OTHER INFORMATION: ADH4

<400> SEQUENCE: 62

```
Met Ser Ser Val Thr Gly Phe Tyr Ile Pro Pro Ile Ser Phe Phe Gly
1               5                   10                  15

Glu Gly Ala Leu Glu Glu Thr Ala Asp Tyr Ile Lys Asn Lys Asp Tyr
            20                  25                  30

Lys Lys Ala Leu Ile Val Thr Asp Pro Gly Ile Ala Ala Ile Gly Leu
        35                  40                  45

Ser Gly Arg Val Gln Lys Met Leu Glu Glu Arg Gly Leu Asn Val Ala
    50                  55                  60

Ile Tyr Asp Lys Thr Gln Pro Asn Pro Asn Ile Ala Asn Val Thr Ala
65                  70                  75                  80

Gly Leu Lys Val Leu Lys Glu Glu Asn Ser Glu Ile Val Val Ser Ile
                85                  90                  95

Gly Gly Gly Ser Ala His Asp Asn Ala Lys Ala Ile Ala Leu Leu Ala
            100                 105                 110

Thr Asn Gly Gly Glu Ile Gly Asp Tyr Glu Gly Val Asn Gln Ser Lys
        115                 120                 125

Lys Ala Ala Leu Pro Leu Phe Ala Ile Asn Thr Thr Ala Gly Thr Ala
130                 135                 140

Ser Glu Met Thr Arg Phe Thr Ile Ile Ser Asn Glu Glu Lys Lys Ile
145                 150                 155                 160

Lys Met Ala Ile Ile Asp Asn Asn Val Thr Pro Ala Val Ala Val Asn
                165                 170                 175

Asp Pro Ser Thr Met Phe Gly Leu Pro Pro Ala Leu Thr Ala Ala Thr
            180                 185                 190

Gly Leu Asp Ala Leu Thr His Cys Ile Glu Ala Tyr Val Ser Thr Ala
        195                 200                 205

Ser Asn Pro Ile Thr Asp Ala Cys Ala Leu Lys Gly Ile Asp Leu Ile
    210                 215                 220

Asn Glu Ser Leu Val Ala Ala Tyr Lys Asp Gly Lys Asp Lys Lys Ala
225                 230                 235                 240

Arg Thr Asp Met Cys Tyr Ala Glu Tyr Leu Ala Gly Met Ala Phe Asn
                245                 250                 255

Asn Ala Ser Leu Gly Tyr Val His Ala Leu Ala His Gln Leu Gly Gly
            260                 265                 270

Phe Tyr His Leu Pro His Gly Val Cys Asn Ala Val Leu Leu Pro His
        275                 280                 285

Val Gln Glu Ala Asn Met Gln Cys Pro Lys Ala Lys Lys Arg Leu Gly
    290                 295                 300

Glu Ile Ala Leu His Cys Gly Ala Ser Gln Glu Asp Pro Glu Thr
305                 310                 315                 320

Ile Lys Ala Leu His Val Leu Asn Arg Thr Met Asn Ile Pro Arg Asn
                325                 330                 335

Leu Lys Asp Leu Gly Val Lys Thr Glu Asp Phe Asp Ile Leu Ala Glu
            340                 345                 350

His Ala Met His Asp Ala Cys His Leu Thr Asn Pro Val Gln Phe Thr
        355                 360                 365

Lys Glu Gln Val Val Ala Ile Ile Lys Lys Ala Tyr Glu Tyr
    370                 375                 380
```

<210> SEQ ID NO 63
<211> LENGTH: 351
<212> TYPE: PRT
<213> ORGANISM: Saccharomyces cerevisiae
<220> FEATURE:
<223> OTHER INFORMATION: ADH5

<400> SEQUENCE: 63

Met Pro Ser Gln Val Ile Pro Glu Lys Gln Lys Ala Ile Val Phe Tyr
1               5                   10                  15

Glu Thr Asp Gly Lys Leu Glu Tyr Lys Asp Val Thr Val Pro Glu Pro
            20                  25                  30

Lys Pro Asn Glu Ile Leu Val His Val Lys Tyr Ser Gly Val Cys His
        35                  40                  45

Ser Asp Leu His Ala Trp His Gly Asp Trp Pro Phe Gln Leu Lys Phe
    50                  55                  60

Pro Leu Ile Gly Gly His Glu Gly Ala Gly Val Val Lys Leu Gly
65                  70                  75                  80

Ser Asn Val Lys Gly Trp Lys Val Gly Asp Phe Ala Gly Ile Lys Trp
                85                  90                  95

Leu Asn Gly Thr Cys Met Ser Cys Glu Tyr Cys Glu Val Gly Asn Glu
            100                 105                 110

Ser Gln Cys Pro Tyr Leu Asp Gly Thr Gly Phe Thr His Asp Gly Thr
        115                 120                 125

Phe Gln Glu Tyr Ala Thr Ala Asp Ala Val Gln Ala Ala His Ile Pro
    130                 135                 140

Pro Asn Val Asn Leu Ala Glu Val Ala Pro Ile Leu Cys Ala Gly Ile
145                 150                 155                 160

Thr Val Tyr Lys Ala Leu Lys Arg Ala Asn Val Ile Pro Gly Gln Trp
                165                 170                 175

Val Thr Ile Ser Gly Ala Cys Gly Gly Leu Gly Ser Leu Ala Ile Gln
            180                 185                 190

Tyr Ala Leu Ala Met Gly Tyr Arg Val Ile Gly Ile Asp Gly Gly Asn
        195                 200                 205

Ala Lys Arg Lys Leu Phe Glu Gln Leu Gly Gly Glu Ile Phe Ile Asp
    210                 215                 220

Phe Thr Glu Glu Lys Asp Ile Val Gly Ala Ile Ile Lys Ala Thr Asn
225                 230                 235                 240

Gly Gly Ser His Gly Val Ile Asn Val Ser Val Ser Glu Ala Ala Ile
                245                 250                 255

Glu Ala Ser Thr Arg Tyr Cys Arg Pro Asn Gly Thr Val Val Leu Val
            260                 265                 270

Gly Met Pro Ala His Ala Tyr Cys Asn Ser Asp Val Phe Asn Gln Val
        275                 280                 285

Val Lys Ser Ile Ser Ile Val Gly Ser Cys Val Gly Asn Arg Ala Asp
    290                 295                 300

Thr Arg Glu Ala Leu Asp Phe Phe Ala Arg Gly Leu Ile Lys Ser Pro
305                 310                 315                 320

Ile His Leu Ala Gly Leu Ser Asp Val Pro Glu Ile Phe Ala Lys Met
                325                 330                 335

Glu Lys Gly Glu Ile Val Gly Arg Tyr Val Val Glu Thr Ser Lys
            340                 345                 350

```
<210> SEQ ID NO 64
<211> LENGTH: 360
<212> TYPE: PRT
<213> ORGANISM: Saccharomyces cerevisiae
<220> FEATURE:
<223> OTHER INFORMATION: ADH6

<400> SEQUENCE: 64

Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60

Val Val Gly His Glu Ile Val Gly Lys Val Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255

Ile Asp Phe Asn Ile Met Pro Lys Ala Met Lys Val Gly Gly Arg Ile
            260                 265                 270

Val Ser Ile Ser Ile Pro Glu Gln His Glu Met Leu Ser Leu Lys Pro
        275                 280                 285

Tyr Gly Leu Lys Ala Val Ser Ile Ser Tyr Ser Ala Leu Gly Ser Ile
    290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
            340                 345                 350

Gly Tyr Asp Lys Glu Phe Ser Asp
        355                 360
```

<210> SEQ ID NO 65
<211> LENGTH: 206
<212> TYPE: PRT
<213> ORGANISM: Saccharomyces cerevisiae
<220> FEATURE:
<223> OTHER INFORMATION: ALD2

<400> SEQUENCE: 65

Met Ala Cys Trp Lys Leu Gln Gly Ala Leu Ala Ala Gly Asn Thr Val
1               5                   10                  15

Ile Ile Lys Pro Ala Glu Asn Thr Ser Leu Ser Leu Leu Tyr Phe Ala
                20                  25                  30

Thr Leu Ile Lys Lys Ala Gly Phe Pro Pro Gly Val Val Asn Ile Val
            35                  40                  45

Pro Gly Tyr Gly Ser Leu Val Gly Gln Ala Leu Ala Ser His Met Asp
        50                  55                  60

Ile Asp Lys Ile Ser Phe Thr Gly Ser Thr Lys Val Gly Gly Phe Val
65                  70                  75                  80

Leu Glu Ala Ser Gly Gln Ser Asn Leu Lys Asp Val Thr Leu Glu Cys
                85                  90                  95

Gly Gly Lys Ser Pro Ala Leu Val Asp Glu Ile Phe Gly Pro Val Val
                100                 105                 110

Val Val Ser Lys Phe Thr Asn Tyr Asp Asp Ala Leu Lys Leu Ala Asn
            115                 120                 125

Asp Thr Cys Tyr Gly Leu Ala Ser Ala Val Phe Thr Lys Asp Val Lys
        130                 135                 140

Lys Ala His Met Phe Ala Arg Asp Ile Lys Ala Gly Thr Val Trp Ile
145                 150                 155                 160

Asn Ser Ser Asn Asp Glu Asp Val Thr Val Pro Phe Gly Gly Phe Lys
                165                 170                 175

Met Ser Gly Ile Gly Arg Glu Leu Gly Gln Ser Gly Val Asp Thr Tyr
                180                 185                 190

Leu Gln Thr Lys Ala Val His Ile Asn Leu Ser Leu Asp Asn
            195                 200                 205

<210> SEQ ID NO 66
<211> LENGTH: 263
<212> TYPE: PRT
<213> ORGANISM: Saccharomyces cerevisiae
<220> FEATURE:
<223> OTHER INFORMATION: ALD3

<400> SEQUENCE: 66

Met Gly Glu Thr Ile Pro Leu Thr Phe Asn Lys Phe Ala Tyr Thr Leu
1               5                   10                  15

Lys Val Pro Phe Gly Val Val Ala Gln Ile Val Pro Trp Asn Tyr Pro
                20                  25                  30

Leu Ala Met Ala Cys Arg Lys Met Gln Gly Ala Leu Ala Ala Gly Asn
            35                  40                  45

Thr Val Ile Ile Lys Pro Ala Glu Asn Thr Ser Leu Ser Leu Leu Tyr
        50                  55                  60

Phe Ala Thr Leu Ile Lys Lys Ala Gly Phe Pro Pro Gly Val Val Asn
65                  70                  75                  80

Val Ile Pro Gly Tyr Gly Ser Val Val Gly Lys Ala Leu Gly Thr His
                85                  90                  95

Met Asp Ile Asp Lys Ile Ser Phe Thr Gly Ser Thr Lys Val Gly Gly
                100                 105                 110

```
Ser Val Leu Glu Ala Ser Gly Gln Ser Asn Leu Lys Asp Ile Thr Leu
            115                 120                 125
Glu Cys Gly Gly Lys Ser Pro Ala Leu Val Phe Glu Asp Ala Asp Leu
130                 135                 140
Asp Lys Ala Ile Glu Trp Val Ala Asn Gly Lys Thr Ser Lys Leu Leu
145                 150                 155                 160
Arg Asp Glu Ile Phe Gly Pro Val Val Val Ser Lys Phe Thr Asn
            165                 170                 175
Tyr Asp Asp Ala Leu Lys Leu Ala Asn Asp Thr Cys Tyr Gly Leu Ala
            180                 185                 190
Ser Ala Val Phe Thr Lys Asp Val Lys Lys Ala His Met Phe Ala Arg
            195                 200                 205
Asp Ile Lys Ala Gly Thr Val Trp Ile Asn Gln Thr Asn Gln Glu Glu
210                 215                 220
Ala Lys Val Pro Phe Gly Gly Phe Lys Met Ser Gly Ile Gly Arg Glu
225                 230                 235                 240
Ser Gly Asp Thr Gly Val Asp Asn Tyr Leu Gln Ile Lys Ser Val His
            245                 250                 255
Val Asp Leu Ser Leu Asp Lys
            260

<210> SEQ ID NO 67
<211> LENGTH: 519
<212> TYPE: PRT
<213> ORGANISM: Saccharomyces cerevisiae
<220> FEATURE:
<223> OTHER INFORMATION: ALD4

<400> SEQUENCE: 67

Met Phe Ser Arg Ser Thr Leu Cys Leu Lys Thr Ser Ala Ser Ser Ile
1               5                   10                  15
Gly Arg Leu Gln Leu Arg Tyr Phe Ser His Leu Pro Met Thr Val Pro
            20                  25                  30
Ile Lys Leu Pro Asn Gly Leu Glu Tyr Glu Gln Pro Thr Gly Leu Phe
        35                  40                  45
Ile Asn Asn Lys Phe Val Pro Ser Lys Gln Asn Lys Thr Phe Glu Val
    50                  55                  60
Ile Asn Pro Ser Thr Glu Glu Ile Cys His Ile Tyr Glu Gly Arg
65                  70                  75                  80
Glu Asp Asp Val Glu Glu Ala Val Gln Ala Ala Asp Arg Ala Phe Ser
                85                  90                  95
Asn Gly Ser Trp Asn Gly Ile Asp Pro Ile Asp Arg Gly Lys Ala Leu
            100                 105                 110
Tyr Arg Leu Ala Glu Leu Ile Glu Gln Asp Lys Asp Val Ile Ala Ser
            115                 120                 125
Ile Glu Thr Leu Asp Asn Gly Lys Ala Ile Ser Ser Ser Arg Gly Asp
        130                 135                 140
Val Asp Leu Val Ile Asn Tyr Leu Lys Ser Ser Ala Gly Phe Ala Asp
145                 150                 155                 160
Lys Ile Asp Gly Arg Met Ile Asp Thr Gly Arg Thr His Phe Ser Tyr
                165                 170                 175
Thr Lys Arg Gln Pro Leu Gly Val Cys Gly Gln Ile Ile Pro Trp Asn
            180                 185                 190
Phe Pro Leu Leu Met Trp Ala Trp Lys Ile Ala Pro Ala Leu Val Thr
            195                 200                 205
```

Gly Asn Thr Val Val Leu Lys Thr Ala Glu Ser Thr Pro Leu Ser Ala
    210                 215                 220

Leu Tyr Val Ser Lys Tyr Ile Pro Gln Ala Gly Ile Pro Pro Gly Val
225                 230                 235                 240

Ile Asn Ile Val Ser Gly Phe Gly Lys Ile Val Gly Glu Ala Ile Thr
                245                 250                 255

Asn His Pro Lys Ile Lys Lys Val Ala Phe Thr Gly Ser Thr Ala Thr
            260                 265                 270

Gly Arg His Ile Tyr Gln Ser Ala Ala Gly Leu Lys Lys Val Thr
        275                 280                 285

Leu Glu Leu Gly Gly Lys Ser Pro Asn Ile Val Phe Ala Asp Ala Glu
    290                 295                 300

Leu Lys Lys Ala Val Gln Asn Ile Ile Leu Gly Ile Tyr Tyr Asn Ser
305                 310                 315                 320

Gly Glu Val Cys Cys Ala Gly Ser Arg Val Tyr Val Glu Glu Ser Ile
                325                 330                 335

Tyr Asp Lys Phe Ile Glu Glu Phe Lys Ala Ala Ser Glu Ser Ile Lys
            340                 345                 350

Val Gly Asp Pro Phe Asp Glu Ser Thr Phe Gln Gly Ala Gln Thr Ser
        355                 360                 365

Gln Met Gln Leu Asn Lys Ile Leu Lys Tyr Val Asp Ile Gly Lys Asn
    370                 375                 380

Glu Gly Ala Thr Leu Ile Thr Gly Gly Glu Arg Leu Gly Ser Lys Gly
385                 390                 395                 400

Tyr Phe Ile Lys Pro Thr Val Phe Gly Asp Val Lys Glu Asp Met Arg
                405                 410                 415

Ile Val Lys Glu Glu Ile Phe Gly Pro Val Val Thr Val Thr Lys Phe
            420                 425                 430

Lys Ser Ala Asp Glu Val Ile Asn Met Ala Asn Asp Ser Glu Tyr Gly
        435                 440                 445

Leu Ala Ala Gly Ile His Thr Ser Asn Ile Asn Thr Ala Leu Lys Val
    450                 455                 460

Ala Asp Arg Val Asn Ala Gly Thr Val Trp Ile Asn Thr Tyr Asn Asp
465                 470                 475                 480

Phe His His Ala Val Pro Phe Gly Gly Phe Asn Ala Ser Gly Leu Gly
                485                 490                 495

Arg Glu Met Ser Val Asp Ala Leu Gln Asn Tyr Leu Gln Val Lys Ala
            500                 505                 510

Val Arg Ala Lys Leu Asp Glu
        515

<210> SEQ ID NO 68
<211> LENGTH: 520
<212> TYPE: PRT
<213> ORGANISM: Saccharomyces cerevisiae
<220> FEATURE:
<223> OTHER INFORMATION: ALD5

<400> SEQUENCE: 68

Met Leu Ser Arg Thr Arg Ala Ala Pro Asn Ser Arg Ile Phe Thr
1               5                   10                  15

Arg Ser Leu Leu Arg Leu Tyr Ser Gln Ala Pro Leu Arg Val Pro Ile
            20                  25                  30

Thr Leu Pro Asn Gly Phe Thr Tyr Glu Gln Pro Thr Gly Leu Phe Ile
        35                  40                  45

```
Asn Gly Glu Phe Val Ala Ser Lys Gln Lys Lys Thr Phe Asp Val Ile
    50              55                  60

Asn Pro Ser Asn Glu Glu Lys Ile Thr Thr Val Tyr Lys Ala Met Glu
65              70                  75                  80

Asp Asp Val Asp Glu Ala Val Ala Ala Lys Lys Ala Phe Glu Thr
                85              90              95

Lys Trp Ser Ile Val Glu Pro Glu Val Arg Ala Lys Ala Leu Phe Asn
                100             105             110

Leu Ala Asp Leu Val Glu Lys His Gln Glu Thr Leu Ala Ala Ile Glu
            115             120             125

Ser Met Asp Asn Gly Lys Ser Leu Phe Cys Ala Arg Gly Asp Val Ala
130             135             140

Leu Val Ser Lys Tyr Leu Arg Ser Cys Gly Gly Trp Ala Asp Lys Ile
145             150             155             160

Tyr Gly Asn Val Ile Asp Thr Gly Lys Asn His Phe Thr Tyr Ser Ile
                165             170             175

Lys Glu Pro Leu Gly Val Cys Gly Gln Ile Ile Pro Trp Asn Phe Pro
            180             185             190

Leu Leu Met Trp Ser Trp Lys Ile Gly Pro Ala Leu Ala Thr Gly Asn
            195             200             205

Thr Val Val Leu Lys Pro Ala Glu Thr Thr Pro Leu Ser Ala Leu Phe
    210             215             220

Ala Ser Gln Leu Cys Gln Glu Ala Gly Ile Pro Ala Gly Val Val Asn
225             230             235             240

Ile Leu Pro Gly Ser Gly Arg Val Val Gly Glu Arg Leu Ser Ala His
            245             250             255

Pro Asp Val Lys Lys Ile Ala Phe Thr Gly Ser Thr Ala Thr Gly Arg
            260             265             270

His Ile Met Lys Val Ala Ala Asp Thr Val Lys Lys Val Thr Leu Glu
            275             280             285

Leu Gly Gly Lys Ser Pro Asn Ile Val Phe Ala Asp Ala Asp Leu Asp
    290             295             300

Lys Ala Val Lys Asn Ile Ala Phe Gly Ile Phe Tyr Asn Ser Gly Glu
305             310             315             320

Val Cys Cys Ala Gly Ser Arg Ile Tyr Ile Gln Asp Thr Val Tyr Glu
                325             330             335

Glu Val Leu Gln Lys Leu Lys Asp Tyr Thr Glu Ser Leu Lys Val Gly
            340             345             350

Asp Pro Phe Asp Glu Glu Val Phe Gln Gly Ala Gln Thr Ser Asp Lys
            355             360             365

Gln Leu His Lys Ile Leu Asp Tyr Val Asp Val Ala Lys Ser Glu Gly
    370             375             380

Ala Arg Leu Val Thr Gly Gly Ala Arg His Gly Ser Lys Gly Tyr Phe
385             390             395             400

Val Lys Pro Thr Val Phe Ala Asp Val Lys Glu Asp Met Arg Ile Val
            405             410             415

Lys Glu Glu Val Phe Gly Pro Ile Val Thr Val Ser Lys Phe Ser Thr
            420             425             430

Val Asp Glu Val Ile Ala Met Ala Asn Asp Ser Gln Tyr Gly Leu Ala
        435             440             445

Ala Gly Ile His Thr Asn Asp Ile Asn Lys Ala Val Asp Val Ser Lys
450             455             460
```

```
Arg Val Lys Ala Gly Thr Val Trp Ile Asn Thr Tyr Asn Asn Phe His
465                 470                 475                 480

Gln Asn Val Pro Phe Gly Gly Phe Gly Gln Ser Gly Ile Gly Arg Glu
            485                 490                 495

Met Gly Glu Ala Ala Leu Ser Asn Tyr Thr Gln Thr Lys Ser Val Arg
500                 505                 510

Ile Ala Ile Asp Lys Pro Ile Arg
515                 520

<210> SEQ ID NO 69
<211> LENGTH: 500
<212> TYPE: PRT
<213> ORGANISM: Saccharomyces cerevisiae
<220> FEATURE:
<223> OTHER INFORMATION: ALD6

<400> SEQUENCE: 69

Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
            20                  25                  30

Lys Phe Met Lys Ala Gln Asp Gly Lys Thr Tyr Pro Val Glu Asp Pro
        35                  40                  45

Ser Thr Glu Asn Thr Val Cys Glu Val Ser Ser Ala Thr Thr Glu Asp
50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
290                 295                 300
```

```
Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
            325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
            355                 360                 365

Gly Ala Lys Ile Leu Thr Gly Glu Lys Val Gly Asp Lys Gly Tyr
370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
            405                 410                 415

Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
            435                 440                 445

Lys Met Leu Lys Ala Gly Thr Val Trp Ile Asn Thr Tyr Asn Asp Phe
450                 455                 460

Asp Ser Arg Val Pro Phe Gly Val Lys Gln Ser Gly Tyr Gly Arg
465                 470                 475                 480

Glu Met Gly Glu Glu Val Tyr His Ala Tyr Thr Glu Val Lys Ala Val
            485                 490                 495

Arg Ile Lys Leu
            500

<210> SEQ ID NO 70
<211> LENGTH: 499
<212> TYPE: PRT
<213> ORGANISM: Arabidopsis thaliana
<220> FEATURE:
<223> OTHER INFORMATION: fumarase

<400> SEQUENCE: 70

Met Ala Ala Leu Thr Met Gln Phe Glu Gly Glu Lys Lys Asn Val Ser
1               5                   10                  15

Glu Val Ala Asp Val Thr Leu Lys Gln Glu Asp Glu Gln Gln Glu Arg
            20                  25                  30

Arg Ser Tyr Ser Thr Pro Phe Arg Glu Glu Arg Asp Thr Phe Gly Pro
        35                  40                  45

Ile Gln Val Pro Ser Asp Lys Leu Trp Gly Ala Gln Thr Gln Arg Ser
50                  55                  60

Leu Gln Asn Phe Glu Ile Gly Gly Asp Arg Glu Arg Met Pro Glu Pro
65                  70                  75                  80

Ile Val Arg Ala Phe Gly Val Leu Lys Lys Cys Ala Ala Lys Val Asn
            85                  90                  95

Met Glu Tyr Gly Leu Asp Pro Met Ile Gly Glu Ala Ile Met Glu Ala
            100                 105                 110

Ala Gln Glu Val Ala Glu Gly Lys Leu Asn Asp His Phe Pro Leu Val
        115                 120                 125

Val Trp Gln Thr Gly Ser Gly Thr Gln Ser Asn Met Asn Ala Asn Glu
130                 135                 140

Val Ile Ala Asn Arg Ala Ala Glu Ile Leu Gly His Lys Arg Gly Glu
145                 150                 155                 160
```

```
Lys Ile Val His Pro Asn Asp His Val Asn Arg Ser Gln Ser Ser Asn
                165                 170                 175

Asp Thr Phe Pro Thr Val Met His Ile Ala Ala Thr Glu Ile Thr
                180                 185                 190

Ser Arg Leu Ile Pro Ser Leu Lys Asn Leu His Ser Ser Leu Glu Ser
            195                 200                 205

Lys Ser Phe Glu Phe Lys Asp Ile Val Lys Ile Gly Arg Thr His Thr
    210                 215                 220

Gln Asp Ala Thr Pro Leu Thr Leu Gly Gln Glu Phe Gly Gly Tyr Ala
225                 230                 235                 240

Thr Gln Val Glu Tyr Gly Leu Asn Arg Val Ala Cys Thr Leu Pro Arg
                245                 250                 255

Ile Tyr Gln Leu Ala Gln Gly Gly Thr Ala Val Gly Thr Gly Leu Asn
                260                 265                 270

Thr Lys Lys Gly Phe Asp Val Lys Ile Ala Ala Ala Val Ala Glu Glu
            275                 280                 285

Thr Asn Leu Pro Phe Val Thr Ala Glu Asn Lys Phe Glu Ala Leu Ala
    290                 295                 300

Ala His Asp Ala Cys Val Glu Thr Ser Gly Ser Leu Asn Thr Ile Ala
305                 310                 315                 320

Thr Ser Leu Met Lys Ile Ala Asn Asp Ile Arg Phe Leu Gly Ser Gly
                325                 330                 335

Pro Arg Cys Gly Leu Gly Glu Leu Ser Leu Pro Glu Asn Glu Pro Gly
                340                 345                 350

Ser Ser Ile Met Pro Gly Lys Val Asn Pro Thr Gln Cys Glu Ala Leu
            355                 360                 365

Thr Met Val Cys Ala Gln Val Met Gly Asn His Val Ala Val Thr Ile
    370                 375                 380

Gly Gly Ser Asn Gly His Phe Glu Leu Asn Val Phe Lys Pro Val Ile
385                 390                 395                 400

Ala Ser Ala Leu Leu His Ser Ile Arg Leu Ile Ala Asp Ala Ser Ala
                405                 410                 415

Ser Phe Glu Lys Asn Cys Val Arg Gly Ile Glu Ala Asn Arg Glu Arg
                420                 425                 430

Ile Ser Lys Leu Leu His Glu Ser Leu Met Leu Val Thr Ser Leu Asn
            435                 440                 445

Pro Lys Ile Gly Tyr Asp Asn Ala Ala Ala Val Ala Lys Arg Ala His
    450                 455                 460

Lys Glu Gly Cys Thr Leu Lys His Ala Ala Met Lys Leu Gly Val Leu
465                 470                 475                 480

Thr Ser Glu Glu Phe Asp Thr Leu Val Val Pro Glu Lys Met Ile Gly
                485                 490                 495

Pro Ser Asp
```

YEAST HOST CELLS FOR DICARBOXYLIC ACID PRODUCTION

This application is the U.S. national phase of International Application No. PCT/EP2016/082415 filed Dec. 22, 2016, which designated the U.S. and claims priority to EP Patent Application No. 15202593.8 filed Dec. 23, 2015, the entire contents of each of which are hereby incorporated by reference.

SUMMARY OF THE INVENTION

The present invention is based on the finding that the deletion of one or more genes encoding enzymes resulting, directly or indirectly, in the oxidation of one or more cofactors, such as NADH, can increase dicarboxylic acid production in a host cell (which cell is capable of producing the dicarboxylic acid), such as production of succinic acid.

Accordingly, the invention relates to a host cell which is capable of producing a dicarboxylic acid and which comprises at least one genetic modification in its genome resulting in the deficiency of at least one enzymatic step catalysing the oxidation of a cofactor.

The invention also relates to:
a method for improving dicarboxylic acid production in a host cell, which method comprises:
  providing a host cell capable of producing a dicarboxylic acid; and
  modifying the host cell in its genome to result in a deficiency of at least one enzymatic step catalysing the oxidation of a cofactor, thereby to improve dicarboxylic acid production in the host cell;
a process for producing a dicarboxylic acid, which method comprises fermenting a host cell of the invention in a suitable fermentation medium and producing the dicarboxylic acid; and
use of a modification in the genome of a host cell to result in a deficiency of at least one enzymatic step catalysing the oxidation of a cofactor, thereby to increase dicarboxylic acid production in the host cell.

DESCRIPTION OF THE SEQUENCE LISTING

Figure 1:
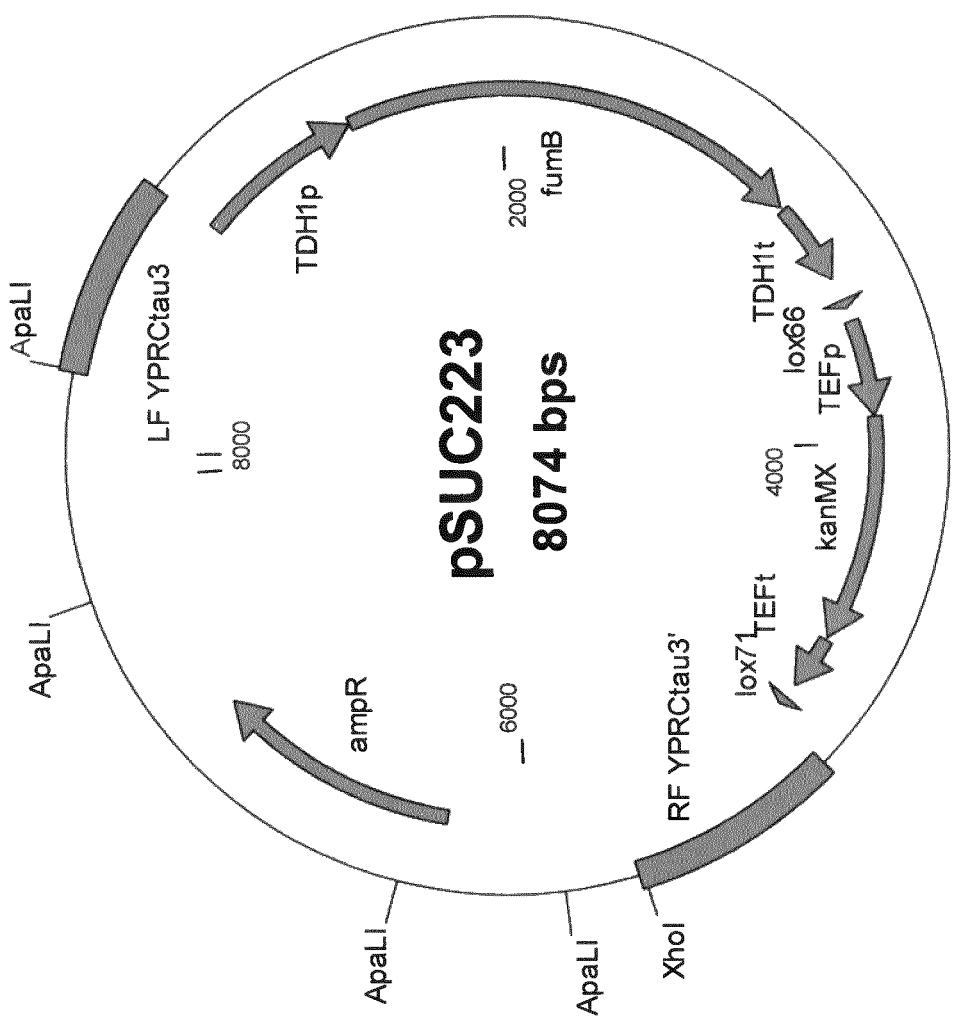
FIG. 1 sets out the plasmid map of pSUC223.

SEQ ID NO: 1 sets out the *Escherichia coli* fumarase fumB amino acid sequence.
SEQ ID NO: 2 sets out the complete nucleic acid sequence of plasmid pSUC223.
SEQ ID NO: 3 sets out the amino acid sequence of FRD1 (encoded by YEL047c) lacking the first 19 amino acids.
SEQ ID NO: 4 sets out the nucleic acid sequence of the synthetic TDH3p-FRD1-TDH3t gene.
SEQ ID NO: 5 sets out the nucleic acid sequence of primer 1 (TDH3p FW with PDC6 5' overhang).
SEQ ID NO: 6 sets out the nucleic acid sequence of primer 2 (TDH3t REV with overhang to pSUC228 Cre-1).
SEQ ID NO: 7 sets out the nucleic acid sequence of primer 3 (pSUC228 Cre-1 FW with overhang TDH3t).
SEQ ID NO: 8 sets out the nucleic acid sequence of primer 4 (DBC-03373, pSUC228 Cre-1 REV).
SEQ ID NO: 9 sets out the complete nucleic acid sequence of plasmid pSUC228.
SEQ ID NO: 10 sets out the nucleic acid sequence of primer 5 (DBC-03374, pSUC225 Cre-2 FW).
SEQ ID NO: 11 sets out the nucleic acid sequence of primer 6 (pSUC225 Cre-2 REV with PDC6 3' overhang).
SEQ ID NO: 12 sets out the glycosomal *Trypanosoma brucei* fumarate reductase (FRDg) amino acid sequence lacking a 3 amino acid C-terminal targeting signal.
SEQ ID NO: 13 sets out the *Rhizopus oryzae* fumarase amino acid sequence, lacking the first 23 N-terminal amino acids.
SEQ ID NO: 14 sets out the *Actinobacillus succinogenes* phosphoenolpyruvate carboxykinase amino acid sequence, with EGY to DAF modification at position 120-122.
SEQ ID NO: 15 sets out the *Saccharomyces cerevisiae* peroxisomal malate dehydrogenase (Mdh3) amino acid sequence, lacking the C-terminal peroxisomal targeting sequence (amino acids SKL).
SEQ ID NO: 16 sets out the *Saccharomyces cerevisiae* pyruvate carboxylase amino acid sequence.
SEQ ID NO: 17 sets out the *Kluyveromyces lactis* isocitrate lyase amino acid sequence.
SEQ ID NO: 18 sets out *Saccharomyces cerevisiae* peroxisomal malate synthase (Mls1) amino acid sequence, lacking the 3 C-terminal peroxisomal targeting sequence.
SEQ ID NO: 19 sets out the amino acid sequence of a dicarboxylic acid transporter from *Aspergillus niger*.
SEQ ID NO: 20 sets out the nucleic acid sequence of primer 7 (FW upstream GUT2).
SEQ ID NO: 21 sets out the nucleic acid sequence of primer 8 (REV upstream GUT2 50 bp Lox66).
SEQ ID NO: 22 sets out the nucleic acid sequence of primer 9 (Cre_1 REV).
SEQ ID NO: 23 sets out the nucleic acid sequence of primer 10 (Cre_2 FW).
SEQ ID NO: 24 sets out the nucleic acid sequence of primer 11 (FW GUT2-KO-Cre_1).
SEQ ID NO: 25 sets out the nucleic acid sequence of primer 12 (REV GUT2-KO-Cre_2).
SEQ ID NO: 26 sets out the nucleic acid sequence of primer 13 (FW downstream GUT2 50bp Lox71).
SEQ ID NO: 27 sets out the nucleic acid sequence of primer 14 (REV downstream GUT2).
SEQ ID NO: 28 sets out the nucleic acid sequence of primer 15 (FW upstream NDE2).
SEQ ID NO: 29 sets out the nucleic acid sequence of primer 16 (REV upstream NDE2 50bp Lox66).
SEQ ID NO: 30 sets out the nucleic acid sequence of primer 17 (FW downstream NDE2 50bp Lox71).
SEQ ID NO: 31 sets out the nucleic acid sequence of primer 18 (REV downstream NDE2).
SEQ ID NO: 32 sets out the nucleic acid sequence of primer 19 (FW NDE2-KO-Cre_1).

SEQ ID NO: 33 sets out the nucleic acid sequence of primer 20 (REV NDE2-KO-Cre_2).

SEQ ID NO: 34 sets out the nucleic acid sequence of primer 21 (FW upstream NDE1).

SEQ ID NO: 35 sets out the nucleic acid sequence of primer 22 (REV upstream NDE1 50bp Lox66).

SEQ ID NO: 36 sets out the nucleic acid sequence of primer 23 (FW downstream NDE1 50bp Lox71).

SEQ ID NO: 37 sets out the nucleic acid sequence of primer 24 (REV downstream NDE1).

SEQ ID NO: 38 sets out the nucleic acid sequence of primer 25 (FW NDE1-KO-Cre_1).

SEQ ID NO: 39 sets out the nucleic acid sequence of primer 26 (REV NDE1-KO-Cre_2).

SEQ ID NO: 40 sets out the *Saccharomyces cerevisiae* amino acid sequence of NDE1.

SEQ ID NO: 41 sets out the *Saccharomyces cerevisiae* amino acid sequence of NDE2.

SEQ ID NO: 42 sets out the *Saccharomyces cerevisiae* amino acid sequence of GUT2.

SEQ ID NO: 43 sets out the nucleic acid sequence of pSUC227.

SEQ ID NO: 44 sets out the nucleic acid sequence of pSUC225.

SEQ ID NO: 45 sets out the nucleic acid sequence of primer 27 (FW upstream gpd1).

SEQ ID NO: 46 sets out the nucleic acid sequence of primer 28 (REV upstream gpd1).

SEQ ID NO: 47 sets out the nucleic acid sequence of primer 29 (FW GPD1-KO-Cre_1).

SEQ ID NO: 48 sets out the nucleic acid sequence of primer 30 (REV GPD1-KO-Cre_2).

SEQ ID NO: 49 sets out the nucleic acid sequence of primer 31 (FW downstream gpd1).

SEQ ID NO: 50 sets out the nucleic acid sequence of primer 32 (REV downstream gpd1).

SEQ ID NO: 51 sets out the nucleic acid sequence of primer 33 (FW upstream gpd2).

SEQ ID NO: 52 sets out the nucleic acid sequence of primer 34 (REV upstream gpd2).

SEQ ID NO: 53 sets out the nucleic acid sequence of primer 35 (FW gpd2-KO-Cre_1).

SEQ ID NO: 54 sets out the nucleic acid sequence of primer 36 (REV gpd KO Cre-2).

SEQ ID NO: 55 sets out the nucleic acid sequence of primer 37 (FW downstream gpd2).

SEQ ID NO: 56 sets out the nucleic acid sequence of primer 38 (REV downstream gpd2).

SEQ ID NO: 57 sets out the *Saccharomyces cerevisiae* amino acid sequence of GPD1 (glycerol 3-phosphate dehydrogenase 1).

SEQ ID NO: 58 sets out the *Saccharomyces cerevisiae* amino acid sequence of GPD2 (glycerol 3-phosphate dehydrogenase 2).

SEQ ID NO: 59 sets out the *Saccharomyces cerevisiae* amino acid sequence of ADH1 (alcohol dehydrogenase 1).

SEQ ID NO: 60 sets out the *Saccharomyces cerevisiae* amino acid sequence of ADH2 (alcohol dehydrogenase 2).

SEQ ID NO: 61 sets out the *Saccharomyces cerevisiae* amino acid sequence of ADH3 (alcohol dehydrogenase 3).

SEQ ID NO: 62 sets out the *Saccharomyces cerevisiae* amino acid sequence of ADH4 (alcohol dehydrogenase 4).

SEQ ID NO: 63 sets out the *Saccharomyces cerevisiae* amino acid sequence of ADH5 (alcohol dehydrogenase 5).

SEQ ID NO: 64 sets out the *Saccharomyces cerevisiae* amino acid sequence of ADH6 (alcohol dehydrogenase 6).

SEQ ID NO: 65 sets out the *Saccharomyces cerevisiae* amino acid sequence of ALD2 (aldehyde dehydrogenase 2).

SEQ ID NO: 66 sets out the *Saccharomyces cerevisiae* amino acid sequence of ALD3 (aldehyde dehydrogenase 3).

SEQ ID NO: 67 sets out the *Saccharomyces cerevisiae* amino acid sequence of ALD4 (aldehyde dehydrogenase 4).

SEQ ID NO: 68 sets out the *Saccharomyces cerevisiae* amino acid sequence of ALD5 (aldehyde dehydrogenase 5).

SEQ ID NO: 69 sets out the *Saccharomyces cerevisiae* amino acid sequence of ALD6 (aldehyde dehydrogenase 6).

SEQ ID NO: 70 sets out the *Arabidopsis thaliana* fumarase amino acid sequence.

DETAILED DESCRIPTION OF THE INVENTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to at least one) of the grammatical object of the article. By way of example, "an element" may mean "one element or more than one element" or "at least one element".

The present invention is based on the finding that the deletion of one or more genes encoding enzymes involved, directly or indirectly, in the oxidation of one or more cofactors, such as NADH, can increase dicarboxylic acid production in a host cell (which cell is capable of producing the dicarboxylic acid), such as production of succinic acid.

According to the invention, there is thus provided a host cell which is capable of producing a dicarboxylic acid and which comprises at least one genetic modification in its genome resulting in the deficiency of at least one enzymatic step catalysing the oxidation of a cofactor.

Deficiency of an enzymatic step catalysing the oxidation of a cofactor referred to herein is defined as a phenotypic feature wherein the host cell of the invention, due to modification in the genome, generates in said enzymatic step less of the cofactor in a partially or fully oxidized state as compared to the parent host cell that has not been modified in its genome according to the invention and when analysed under substantially identical conditions.

That is to say, deficiency of an enzymatic step catalysing the oxidation of a cofactor in the host cell of the invention results in reduced oxidation of a partially or fully reduced form of the cofactor in said step as compared to the parent host cell that has not been modified in its genome according to the invention (when analysed under substantially identical conditions).

Thus, in the host cell of the invention the availability of one or more cofactor in a more reduced state (partially or fully reduced) is increased as compared to the parent host cell which has not been modified in its genome according to the invention (when analysed under substantially identical conditions).

Deficiency of an enzymatic step catalysing the oxidation of a cofactor in the host cell of the invention is typically the result of a modification in the genome of wherein the cell: a) produces less of a polypeptide and/or b) has a reduced expression level of the mRNA transcribed from a gene encoding the polypeptide and/or c) produces a polypeptide having a decreased protein activity or decreased specific protein activity and/or d) produces less of a product produced by the polypeptide and combinations of one or more of these possibilities as compared to the parent host cell that has not been modified in its genome according to the invention, when analysed under substantially identical conditions. The polypeptide may be one which directly or indirectly leads to oxidation of one or more cofactors.

In this context, a gene is herewith defined as a polynucleotide containing an open reading frame (ORF) together with its transcriptional control elements (promoter and terminator), the ORF being the region on the gene that will be transcribed and translated into the protein sequence.

Therefore, deficiency of an enzymatic step may be measured by determining the amount and/or (specific) activity of a polypeptide that directly or indirectly leads to oxidation of one or more cofactors produced by the host cell of the invention as defined above and/or it may be measured by determining the amount of mRNA transcribed from a gene encoding the polypeptide and/or it may be measured by determining the amount of a product produced by the polypeptide in the host cell of the invention as defined above and/or it may be measured by gene or genome sequencing if compared to the parent host cell that has not been modified in its genome according to the invention (when analysed under substantially identical conditions). Deficiency in the production of a polypeptide can be measured using any assay available to the skilled person, such as transcriptional profiling, Northern blotting RT-PCR, Q-PCR, proteomics, and Western blotting.

Modification of a genome of a host cell is herein defined as any event resulting in a change in a polynucleotide sequence in the genome of the cell. A modification is construed as one or more modifications. Modification can be introduced by classical strain improvement, random mutagenesis followed by selection. Modification may be accomplished by the introduction (insertion), substitution or removal (deletion) of one or more nucleotides in a nucleotide sequence. This modification may for example be in a coding sequence or a regulatory element required for the transcription or translation of the polynucleotide. For example, nucleotides may be inserted or removed so as to result in the introduction of a stop codon, the removal of a start codon or a change or a frame-shift of the open reading frame of a coding sequence. The modification of a coding sequence or a regulatory element thereof may be accomplished by site-directed or random mutagenesis, DNA shuffling methods, DNA reassembly methods, gene synthesis (see for example *Young and Dong*, (2004), *Nucleic Acids Research* 32, (7) *electronic access http://nar.oupjournals.org/cgi/reprint/32/7/e59 or Gupta et al.* (1968), *Proc. Natl. Acad. Sci USA,* 60: 1338-1344; *Scarpulla et al.* (1982), *Anal. Biochem.* 121: 356-365; *Stemmer et al.* (1995), *Gene* 164: 49-53), or PCR generated mutagenesis in accordance with methods known in the art. Examples of random mutagenesis procedures are well known in the art, such as for example chemical (NTG for example) mutagenesis or physical (UV for example) mutagenesis. Examples of directed mutagenesis procedures are the QuickChange™ site-directed mutagenesis kit (Stratagene Cloning Systems, La Jolla, Calif.), the 'The Altered Sites® II in vitro Mutagenesis Systems' (Promega Corporation) or by overlap extension using PCR as described in *Gene* (1989) 77(1):51-9 (Ho S N, Hunt H D, Horton R M, Pullen J K, Pease L R "Site-directed mutagenesis by overlap extension using the polymerase chain reaction") or using PCR as described in *Molecular Biology: Current Innovations and Future Trends.* (Eds. A. M. Griffin and H. G. Griffin. ISBN 1-898486-01-8; 1995 *Horizon Scientific Press, PO Box* 1, *Wymondham, Norfolk, U.K.*).

A modification in the genome can be determined by comparing the DNA sequence of the modified host cell to the sequence of the parent host cell. Sequencing of DNA and genome sequencing can be done using standard methods known to the person skilled in the art, for example using Sanger sequencing technology and/or next generation sequencing technologies such as Illumina GA2, Roche 454, etc. as reviewed in *Elaine R. Mardis* (2008), *Next-Generation DNA Sequencing Methods, Annual Review of Genomics and Human Genetics,* 9: 387-402. (doi:10.1146/annurev.genom.9.081307.164359).

Preferred methods of modification are based on techniques of gene replacement, gene deletion, or gene disruption.

For example, in case of replacement of a polynucleotide, nucleic acid construct or expression cassette, an appropriate DNA sequence may be introduced at the target locus to be replaced. The appropriate DNA sequence is preferably present on a cloning vector. Preferred integrative cloning vectors comprise a DNA fragment, which is homologous to the polynucleotide and/or has homology to the polynucleotides flanking the locus to be replaced for targeting the integration of the cloning vector to this pre-determined locus. In order to promote targeted integration, the cloning vector is preferably linearized prior to transformation of the cell. Preferably, linearization is performed such that at least one but preferably either end of the cloning vector is flanked by sequences homologous to the DNA sequence (or flanking sequences) to be replaced. This process is called homologous recombination and this technique may also be used in order to achieve (partial) gene deletion or gene disruption.

For example, for gene disruption, a polynucleotide corresponding to the endogenous polynucleotide may be replaced by a defective polynucleotide, that is a polynucleotide that fails to produce a (fully functional) protein. By homologous recombination, the defective polynucleotide replaces the endogenous polynucleotide. It may be desirable that the defective polynucleotide also encodes a marker, which may be used for selection of transformants in which the nucleic acid sequence has been modified.

Alternatively, modification, wherein said host cell produces less of or is deficient in the production of one of the polypeptides described herein may be performed by established anti-sense techniques using a nucleotide sequence complementary to the nucleic acid sequence of the polynucleotide. More specifically, expression of the polynucleotide by a host cell of the invention may be reduced or eliminated by introducing a nucleotide sequence complementary to the nucleic acid sequence of the polynucleotide, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated. An example of expressing an antisense-RNA is shown in *Appl. Environ. Microbiol.* (2000) February; 66(2):775-82 (*Characterization of a foldase, protein disulfide isomerase A, in the protein secretory pathway of Aspergillus niger.* Ngiam C, Jeenes D J, Punt P J, Van Den Hondel C A, Archer D B) or (Zrenner R, Willmitzer L, Sonnewald U. *Analysis of the expression of potato uridinediphosphate-glucose pyrophosphorylase and its inhibition by antisense RNA. Planta.* (1993); 190(2):247-52).

Furthermore, modification, downregulation or inactivation of a polynucleotide may be obtained via the RNA interference (RNAi) technique (*FEMS Microb. Lett.* 237 (2004): 317-324). In this method, identical sense and antisense parts of the nucleotide sequence, which expression is to be affected, are cloned behind each other with a nucleotide spacer in between, and inserted into an expression vector. After such a molecule is transcribed, formation of small nucleotide fragments will lead to a targeted degradation of the mRNA, which is to be affected. The elimination of the specific mRNA can be to various extents. The RNA interference techniques described in WO2008/053019, WO2005/05672A1, WO2005/026356A1, Oliveira et al., "*Efficient cloning system for construction of gene silencing vectors in Aspergillus niger*" (2008) *Appl. Microbiol. and Biotechnol.* 80 (5): 917-924 and/or Barnes et al., "*siRNA as a molecular tool for use in Aspergillus niger*" (2008) *Biotechnology Letters* 30 (5): 885-890 may be used for downregulation, modification or inactivation of a polynucleotide.

Herein, a cofactor typically refers to a non-protein chemical compound that is required for the biological activity of a protein, such an enzyme. That is to say, the cofactor can be considered a "helper molecule" that assists in a biochemical transformation. In the context of the invention, the terms "cofactor" and "coenzyme" have the same meaning herein and are used interchangeably.

Typically, the modification in the genome of the host cell of the invention will result in a deficiency in the oxidation of an organic cofactor. Such cofactors are typically small organic molecules (typically a molecular mass less than 1000 Da) that can be either loosely or tightly bound to the enzyme and may directly participate in the reaction. A cofactor can be tightly bound in some enzymes, while it is loosely bound in others.

In a host cell of the invention, the modification in the genome typically results in a deficiency in oxidation of a partially or fully reduced form of the cofactor. In the invention, the cofactor may be NADH, NADPH or FAD $H_2$.

The modification in the genome of a host cell in the invention may result directly or indirectly in a deficiency in the oxidation of a cofactor.

In a host cell of the invention, the modification in the genome typically results in the deficiency of the at least one enzymatic step catalysing the oxidation of a cofactor in the cytosol.

In a host cell of the invention, the host cell comprises at least one genetic modification in its genome resulting in the deficiency of:
 at least one mitochondrial external NADH dehydrogenase; or
 at least one mitochondrial glycerol-3-phosphate dehydrogenase; or
 at least one cytosolic glycerol-3-phosphate dehydrogenase; or
 at least one alcohol dehydrogenase; or
 at least one aldehyde dehydrogenase; or
 a combination thereof.

In a host cell of the invention, the mitochondrial external NADH dehydrogenase has an amino acid sequence comprising a sequence as set out in SEQ ID NO: 40 or SEQ ID NO: 41 or comprising a sequence having at least 35% identity, more preferably at least 40% identity, more preferably at least 45% identity, more preferably at least 50% identity, even more preferably at least 55% identity, even more preferably at least 60% identity, even more preferably at least 65% identity, even more preferably at least 70% identity, even more preferably at least 75% identity, even more preferably at least 80% identity, even more preferably at least 85% identity, even more preferably at least 90% identity, for example at least 91% identity, for example at least 92% identity, for example at least 93% identity, for example at least 94% identity, for example at least 95% identity, for example at least 96% identity, for example at least 97% identity, for example at least 98% identity, for example at least 99% identity with SEQ ID NO: 40 or SEQ ID NO:41.

In a host cell of the invention, the mitochondrial glycerol-3-phosphate dehydrogenase has an amino acid sequence comprising a sequence as set out in SEQ ID NO: 42 or comprising a sequence having at least 35% identity, more preferably at least 40% identity, more preferably at least 45% identity, more preferably at least 50% identity, even more preferably at least 55% identity, even more preferably at least 60% identity, even more preferably at least 65% identity, even more preferably at least 70% identity, even more preferably at least 75% identity, even more preferably at least 80% identity, even more preferably at least 85% identity, even more preferably at least 90% identity, for example at least 91% identity, for example at least 92% identity, for example at least 93% identity, for example at least 94% identity, for example at least 95% identity, for example at least 96% identity, for example at least 97% identity, for example at least 98% identity, for example at least 99% identity with SEQ ID NO: 42.

In a host cell of the invention, the cytosolic glycerol-3-phosphate dehydrogenase has an amino acid sequence comprising a sequence as set out in SEQ ID NO: 57 or SEQ ID NO: 58 or comprising a sequence having at least 35% identity, more preferably at least 40% identity, more preferably at least 45% identity, more preferably at least 50% identity, even more preferably at least 55% identity, even more preferably at least 60% identity, even more preferably at least 65% identity, even more preferably at least 70% identity, even more preferably at least 75% identity, even more preferably at least 80% identity, even more preferably at least 85% identity, even more preferably at least 90% identity, for example at least 91% identity, for example at least 92% identity, for example at least 93% identity, for example at least 94% identity, for example at least 95% identity, for example at least 96% identity, for example at least 97% identity, for example at least 98% identity, for example at least 99% identity with SEQ ID NO: 57 or SEQ ID NO: 58.

In a host cell of the invention, the alcohol dehydrogenase has an amino acid sequence comprising a sequence as set out in SEQ ID NO: 59, SEQ ID NO: 60, SEQ ID NO: 61, SEQ ID NO: 62, SEQ ID NO: 63 or SEQ ID NO: 64 or comprising a sequence having at least 35% identity, more preferably at least 40% identity, more preferably at least 45% identity, more preferably at least 50% identity, even more preferably at least 55% identity, even more preferably at least 60% identity, even more preferably at least 65% identity, even more preferably at least 70% identity, even more preferably at least 75% identity, even more preferably at least 80% identity, even more preferably at least 85% identity, even more preferably at least 90% identity, for example at least 91% identity, for example at least 92% identity, for example at least 93% identity, for example at least 94% identity, for example at least 95% identity, for example at least 96% identity, for example at least 97% identity, for example at least 98% identity, for example at least 99% identity with SEQ ID NO: 59, SEQ ID NO: 60, SEQ ID NO: 61, SEQ ID NO: 62, SEQ ID NO: 63 or SEQ ID NO: 64.

In a host cell of the invention, the aldehyde dehydrogenase has an amino acid sequence comprising a sequence as set out in SEQ ID NO: 65, SEQ ID NO: 66, SEQ ID NO: 67, SEQ ID NO: 68 or SEQ ID NO: 69 or comprising a sequence having at least 35% identity, more preferably at least 40% identity, more preferably at least 45% identity, more preferably at least 50% identity, even more preferably at least 55% identity, even more preferably at least 60% identity, even more preferably at least 65% identity, even more preferably at least 70% identity, even more preferably at least 75% identity, even more preferably at least 80% identity, even more preferably at least 85% identity, even more preferably at least 90% identity, for example at least 91% identity, for example at least 92% identity, for example at least 93% identity, for example at least 94% identity, for example at least 95% identity, for example at least 96% identity, for example at least 97% identity, for example at least 98% identity, for example at least 99% identity with SEQ ID NO: 65, SEQ ID NO: 66, SEQ ID NO: 67, SEQ ID NO: 68 or SEQ ID NO: 69.

In an embodiment, the host cell of the invention comprises at least one genetic modification in its genome resulting in the deficiency of:
  at least one mitochondrial external NADH dehydrogenase.

In particular, the host cell of the invention comprises at least one genetic modification in its genome resulting in the deficiency of:
  at least one mitochondrial external NADH dehydrogenase having an amino acid sequence comprising a sequence as set out in SEQ ID NO: 40 or SEQ ID NO: 41 or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:40 or SEQ ID NO: 41;

More in particular, the host cell of the invention comprises at least one genetic modification in its genome resulting in the deficiency of:
  a mitochondrial external NADH dehydrogenase having an amino acid sequence comprising a sequence as set out in SEQ ID NO: 40 or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:40; and
  a mitochondrial external NADH dehydrogenase having an amino acid sequence comprising a sequence as set out in SEQ ID NO: 41 or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:41.

In yet another embodiment, the host cell of the invention comprises at least one genetic modification in its genome resulting in the deficiency of:
  at least one mitochondrial external NADH dehydrogenase; and
  at least one mitochondrial glycerol-3-phosphate dehydrogenase.

In particular, the host cell of the invention comprises at least one genetic modification in its genome resulting in the deficiency of:
  at least one mitochondrial external NADH dehydrogenase having an amino acid sequence comprising a sequence as set out in SEQ ID NO: 40 or SEQ ID NO: 41 or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:40 or SEQ ID NO: 41; and
  at least one mitochondrial glycerol-3-phosphate dehydrogenase having an amino acid sequence comprising a sequence as set out in SEQ ID NO: 42 or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:42.

More in particular, the host cell of the invention comprises at least one genetic modification in its genome resulting in the deficiency of:
  a mitochondrial external NADH dehydrogenase having an amino acid sequence comprising a sequence as set out in SEQ ID NO: 40 or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:40; and
  a mitochondrial external NADH dehydrogenase having an amino acid sequence comprising a sequence as set out in SEQ ID NO: 41 or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:41; and
  a mitochondrial glycerol-3-phosphate dehydrogenase having an amino acid sequence comprising a sequence as set out in SEQ ID NO: 42 or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:42.

Even more in particular, the host cell of the invention comprises at least one genetic modification in its genome resulting in the deficiency of:
- a mitochondrial external NADH dehydrogenase having an amino acid sequence comprising a sequence having at least 70% identity with SEQ ID NO:40; and
- a mitochondrial external NADH dehydrogenase having an amino acid sequence comprising a sequence having at least 70% identity with SEQ ID NO:41; and
- a mitochondrial glycerol-3-phosphate dehydrogenase having an amino acid sequence comprising a sequence having at least 70% identity with SEQ ID NO:42.

Even more in particular, the host cell of the invention comprises at least one genetic modification in its genome resulting in the deficiency of:
- a mitochondrial external NADH dehydrogenase having an amino acid sequence comprising a sequence having at least 80% identity with SEQ ID NO:40; and
- a mitochondrial external NADH dehydrogenase having an amino acid sequence comprising a sequence having at least 80% identity with SEQ ID NO:41; and
- a mitochondrial glycerol-3-phosphate dehydrogenase having an amino acid sequence comprising a sequence having at least 80% identity with SEQ ID NO:42.

Even more in particular, the host cell of the invention comprises at least one genetic modification in its genome resulting in the deficiency of:
- a mitochondrial external NADH dehydrogenase having an amino acid sequence comprising a sequence having at least 90% identity with SEQ ID NO:40; and
- a mitochondrial external NADH dehydrogenase having an amino acid sequence comprising a sequence having at least 90% identity with SEQ ID NO:41; and
- a mitochondrial glycerol-3-phosphate dehydrogenase having an amino acid sequence comprising a sequence having at least 90% identity with SEQ ID NO:42.

Even more in particular, the host cell of the invention comprises at least one genetic modification in its genome resulting in the deficiency of:
- a mitochondrial external NADH dehydrogenase having an amino acid sequence comprising a sequence having at least 95% identity with SEQ ID NO:40; and
- a mitochondrial external NADH dehydrogenase having an amino acid sequence comprising a sequence having at least 95% identity with SEQ ID NO:41; and
- a mitochondrial glycerol-3-phosphate dehydrogenase having an amino acid sequence comprising a sequence having at least 95% identity with SEQ ID NO:42.

Most in particular, the host cell of the invention comprises at least one genetic modification in its genome resulting in the deficiency of:
- a mitochondrial external NADH dehydrogenase having an amino acid sequence comprising the sequence as set out in SEQ ID NO: 40; and
- a mitochondrial external NADH dehydrogenase having an amino acid sequence comprising the sequence as set out in SEQ ID NO: 41; and
- a mitochondrial glycerol-3-phosphate dehydrogenase having an amino acid sequence comprising the sequence as set out in SEQ ID NO: 42.

In another embodiment, the host cell of the invention comprises at least one genetic modification in its genome resulting in the deficiency of:
- at least one mitochondrial external NADH dehydrogenase; and
- at least one mitochondrial glycerol-3-phosphate dehydrogenase; and
- at least one cytosolic glycerol-3-phosphate dehydrogenase.

In particular, the host cell of the invention comprises at least one genetic modification in its genome resulting in the deficiency of:
- at least one mitochondrial external NADH dehydrogenase having an amino acid sequence comprising a sequence as set out in SEQ ID NO: 40 or SEQ ID NO: 41, or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:40 or SEQ ID NO: 41; and
- at least one mitochondrial glycerol-3-phosphate dehydrogenase having an amino acid sequence comprising a sequence as set out in SEQ ID NO: 42 or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:42; and
- at least one cytosolic glycerol-3-phosphate dehydrogenase having an amino acid sequence comprising a sequence as set out in SEQ ID NO: 57 or SEQ ID NO: 58, or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO: 57 or SEQ ID NO: 58.

More in particular, the host cell of the invention comprises at least one genetic modification in its genome resulting in the deficiency of:
- a mitochondrial external NADH dehydrogenase having an amino acid sequence comprising a sequence as set out in SEQ ID NO: 40 or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:40; and
- a mitochondrial external NADH dehydrogenase having an amino acid sequence comprising a sequence as set out in SEQ ID NO: 41 or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:41; and
- a mitochondrial glycerol-3-phosphate dehydrogenase having an amino acid sequence comprising a sequence as set out in SEQ ID NO: 42 or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:42; and
a cytosolic glycerol-3-phosphate dehydrogenase having an amino acid sequence comprising a sequence as set out in SEQ ID NO: 57 or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO: 57; and a cytosolic glycerol-3-phosphate dehydrogenase having an amino acid sequence comprising a sequence as set out in SEQ ID NO: 58 or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO: 58.

Even more in particular, the host cell of the invention comprises at least one genetic modification in its genome resulting in the deficiency of:
a mitochondrial external NADH dehydrogenase having an amino acid sequence comprising a sequence having at least 70% identity with SEQ ID NO:40; and
a mitochondrial external NADH dehydrogenase having an amino acid sequence comprising a sequence having at least 70% identity with SEQ ID NO:41; and
a mitochondrial glycerol-3-phosphate dehydrogenase having an amino acid sequence comprising a sequence having at least 70% identity with SEQ ID NO:42; and
a cytosolic glycerol-3-phosphate dehydrogenase having an amino acid sequence comprising a sequence having at least 70% identity with SEQ ID NO: 57; and
a cytosolic glycerol-3-phosphate dehydrogenase having an amino acid sequence comprising a sequence having at least 70% identity with SEQ ID NO: 58.

Even more in particular, the host cell of the invention comprises at least one genetic modification in its genome resulting in the deficiency of:
a mitochondrial external NADH dehydrogenase having an amino acid sequence comprising a sequence having at least 80% identity with SEQ ID NO:40; and
a mitochondrial external NADH dehydrogenase having an amino acid sequence comprising a sequence having at least 80% identity with SEQ ID NO:41; and
a mitochondrial glycerol-3-phosphate dehydrogenase having an amino acid sequence comprising a sequence having at least 80% identity with SEQ ID NO:42; and
a cytosolic glycerol-3-phosphate dehydrogenase having an amino acid sequence comprising a sequence having at least 80% identity with SEQ ID NO: 57; and
a cytosolic glycerol-3-phosphate dehydrogenase having an amino acid sequence comprising a sequence having at least 80% identity with SEQ ID NO: 58.

Even more in particular, the host cell of the invention comprises at least one genetic modification in its genome resulting in the deficiency of:
a mitochondrial external NADH dehydrogenase having an amino acid sequence comprising a sequence having at least 90% identity with SEQ ID NO:40; and
a mitochondrial external NADH dehydrogenase having an amino acid sequence comprising a sequence having at least 90% identity with SEQ ID NO:41; and
a mitochondrial glycerol-3-phosphate dehydrogenase having an amino acid sequence comprising a sequence having at least 90% identity with SEQ ID NO:42; and
a cytosolic glycerol-3-phosphate dehydrogenase having an amino acid sequence comprising a sequence having at least 90% identity with SEQ ID NO: 57; and
a cytosolic glycerol-3-phosphate dehydrogenase having an amino acid sequence comprising a sequence having at least 90% identity with SEQ ID NO: 58.

Even more in particular, the host cell of the invention comprises at least one genetic modification in its genome resulting in the deficiency of:
a mitochondrial external NADH dehydrogenase having an amino acid sequence comprising a sequence having at least 95% identity with SEQ ID NO:40; and
a mitochondrial external NADH dehydrogenase having an amino acid sequence comprising a sequence having at least 95% identity with SEQ ID NO:41; and
a mitochondrial glycerol-3-phosphate dehydrogenase having an amino acid sequence comprising a sequence having at least 95% identity with SEQ ID NO:42; and
a cytosolic glycerol-3-phosphate dehydrogenase having an amino acid sequence comprising a sequence having at least 95% identity with SEQ ID NO: 57; and
a cytosolic glycerol-3-phosphate dehydrogenase having an amino acid sequence comprising a sequence having at least 95% identity with SEQ ID NO: 58.

Most in particular, the host cell of the invention comprises at least one genetic modification in its genome resulting in the deficiency of:
a mitochondrial external NADH dehydrogenase having an amino acid sequence comprising the sequence as set out in SEQ ID NO: 40; and
a mitochondrial external NADH dehydrogenase having an amino acid sequence comprising the sequence as set out in SEQ ID NO: 41; and
a mitochondrial glycerol-3-phosphate dehydrogenase having an amino acid sequence comprising the sequence as set out in SEQ ID NO: 42; and
a cytosolic glycerol-3-phosphate dehydrogenase having an amino acid sequence comprising the sequence as set out in SEQ ID NO: 57; and
a cytosolic glycerol-3-phosphate dehydrogenase having an amino acid sequence comprising the sequence as set out in SEQ ID NO: 58.

In yet another embodiment, the host cell of the invention comprises at least one genetic modification in its genome resulting in the deficiency of:
at least one cytosolic glycerol-3-phosphate dehydrogenase.

In particular, the host cell of the invention comprises at least one genetic modification in its genome resulting in the deficiency of:
at least one cytosolic glycerol-3-phosphate dehydrogenase having an amino acid sequence comprising a sequence as set out in SEQ ID NO: 57 or SEQ ID NO: 58, or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO: 57 or SEQ ID NO: 58.

More in particular, the host cell of the invention comprises at least one genetic modification in its genome resulting in the deficiency of:
- a cytosolic glycerol-3-phosphate dehydrogenase having an amino acid sequence comprising a sequence as set out in SEQ ID NO: 57 or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO: 57; and
- a cytosolic glycerol-3-phosphate dehydrogenase having an amino acid sequence comprising a sequence as set out in SEQ ID NO: 58 or comprising a sequence having at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO: 58.

Even more in particular, the host cell of the invention comprises at least one genetic modification in its genome resulting in the deficiency of:
- a cytosolic glycerol-3-phosphate dehydrogenase having an amino acid sequence comprising a sequence having at least 70% identity with SEQ ID NO: 57; and
- a cytosolic glycerol-3-phosphate dehydrogenase having an amino acid sequence comprising a sequence having at least 70% identity with SEQ ID NO: 58.

Even more in particular, the host cell of the invention comprises at least one genetic modification in its genome resulting in the deficiency of:
- a cytosolic glycerol-3-phosphate dehydrogenase having an amino acid sequence comprising a sequence having at least 80% identity with SEQ ID NO: 57; and
- a cytosolic glycerol-3-phosphate dehydrogenase having an amino acid sequence comprising a sequence having at least 80% identity with SEQ ID NO: 58.

Even more in particular, the host cell of the invention comprises at least one genetic modification in its genome resulting in the deficiency of:
- a cytosolic glycerol-3-phosphate dehydrogenase having an amino acid sequence comprising a sequence having at least 90% identity with SEQ ID NO: 57; and
- a cytosolic glycerol-3-phosphate dehydrogenase having an amino acid sequence comprising a sequence having at least 90% identity with SEQ ID NO: 58.

Even more in particular, the host cell of the invention comprises at least one genetic modification in its genome resulting in the deficiency of:
- a cytosolic glycerol-3-phosphate dehydrogenase having an amino acid sequence comprising a sequence having at least 95% identity with SEQ ID NO: 57; and
- a cytosolic glycerol-3-phosphate dehydrogenase having an amino acid sequence comprising a sequence having at least 95% identity with SEQ ID NO: 58.

Most in particular, the host cell of the invention comprises at least one genetic modification in its genome resulting in the deficiency of:
- a cytosolic glycerol-3-phosphate dehydrogenase having an amino acid sequence comprising the sequence as set out in SEQ ID NO: 57; and
- a cytosolic glycerol-3-phosphate dehydrogenase having an amino acid sequence comprising the sequence as set out in SEQ ID NO: 58.

In a yet another further embodiment, the host cell of the invention as described herein above further comprises at least one genetic modification in its genome resulting in the deficiency of at least one alcohol dehydrogenase and/or at least one aldehyde dehydrogenase. Preferred embodiments of the alcohol dehydrogenase and the aldehyde dehydrogenase are as described herein above.

Preferably, in a host cell of the invention, the deficiency in the production of one or more of the polypeptides identified herein is a reduction in production of at least 20%, more preferably by at least 30%, more preferably by at least 40%, even more preferably at least 50%, even more preferably at least 60%, in particular at least 70%, more in particular at least 80%, for example at least 85%, for example at least 90%, for example at least 95%, for example at least 100% (as compared to the parent host cell that has not been modified in its genome according to the invention, when analysed under substantially identical conditions).

Preferably, in a host cell of the invention, the deficiency in the expression level of the mRNA transcribed from one or more genes encoding the one or more polypeptides identified herein is a reduction in expression of at least 20%, more preferably by at least 30%, more preferably by at least 40%, even more preferably at least 50%, even more preferably at least 60%, in particular at least 70%, more in particular at least 80%, for example at least 85%, for example at least 90%, for example at least 95%, for example at least 100% (as compared to the parent host cell that has not been modified in its genome according to the invention, when analysed under substantially identical conditions).

Preferably, in a host cell of the invention, the deficiency in the protein activity or in the specific protein activity of the one or more polypeptides identified herein is a reduction in activity or specific activity of at least 20%, more preferably by at least 30%, more preferably by at least 40%, even more preferably at least 50%, even more preferably at least 60%, in particular at least 70%, more in particular at least 80%, for example at least 85%, for example at least 90%, for example at least 95%, for example at least 100% (as compared to the parent host cell that has not been modified in its genome according to the invention, when analysed under substantially identical conditions).

Preferably, in a host cell of the invention, the deficiency in product produced by the one or more polypeptides is a reduction in production of at least 20%, more preferably by at least 30%, more preferably by at least 40%, even more preferably at least 50%, even more preferably at least 60%, in particular at least 70%, more in particular at least 80%, for example at least 85%, for example at least 90%, for example at least 95%, for example at least 100% (as compared to the parent host cell that has not been modified in its genome according to the invention, when analysed under substantially identical conditions).

A host cell of the invention is capable of producing a dicarboxylic acid, such as malic acid, fumaric acid and/or succinic acid.

The terms "dicarboxylic acid" and "dicarboxylate", such as "succinic acid" and "succinate", have the same meaning herein and are used interchangeably, the first being the hydrogenated form of the latter.

As described herein above, a host cell of the invention is a genetically modified host cell that comprises at least one genetic modification in its genome (e.g. a deletion or disruption of an endogenous or homologous nucleotide sequence), thereby resulting in the deficiency of at least one enzymatic step catalysing the oxidation of a cofactor. A host cell of the invention is derived or generated from a "parent host cell" (which has not been modified in its genome according to the invention). The parent host cell may be a wild-type strain or a genetically modified host cell. For example, a parent host cell may be any wild type strain producing a dicarboxylic acid. Alternatively, a parent host cell may be any wild type strain of interest that has been subjected to a classical mutagenic treatment or to recombinant nucleic acid transformation for dicarboxylic acid production. For example, the parent host cell may contain a homologous or heterologous expression construct that encodes a polypeptide involved in the production of a dicarboxylic acid.

The person skilled in the art will be aware of methods for modification of a cell, such as microbial cells, so that it is capable of production of the polypeptide involved in the production of the dicarboxylic acid. For this purpose, methods of recombinant gene technology are well established in the art and are described in *Sambrook and Russel* (2001) "*Molecular Cloning: A Laboratory Manual* (3rd edition), *Cold Spring Harbor Laboratory, Cold Spring Harbor Laboratory Press* or *F. Ausubel et al, eds., "Current protocols in molecular biology", Green Publishing and Wiley Interscience, New York* (1987).

The term "nucleic acid" as used herein, includes reference to a deoxyribonucleotide (DNA) or ribonucleotide (RNA) polymer, i.e. a polynucleotide, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof.

As used herein, a "gene" may refer to an isolated nucleic acid molecule. Accordingly, the term "gene", in the context of the present application, does not refer only to naturally-occurring sequences.

The term "heterologous" as used herein refers to nucleic acid or amino acid sequences not naturally occurring in a host cell. In other words, the nucleic acid or amino acid sequence is not identical to that naturally found in the host cell.

As used herein, the term "endogenous" or "homologous" refers to a nucleic acid or amino acid sequence naturally occurring in a host cell.

A suitable host cell of the invention may be a prokaryotic cell. Preferably, the prokaryotic cell is a bacterial cell. The term "bacterial cell" includes both Gram-negative and Gram-positive microorganisms.

Suitable bacteria may be selected from e.g. *Escherichia, Anabaena, Caulobactert, Gluconobacter, Rhodobacter, Pseudomonas, Paracoccus, Bacillus, Brevibacterium, Corynebacterium, Rhizobium* (*Sinorhizobium*), *Flavobacterium, Klebsiella, Enterobacter, Lactobacillus, Lactococcus, Methylobacterium, Staphylococcus* or *Actinomycetes* such as *Streptomyces* and *Actinoplanes* species. Preferably, the bacterial cell is selected from the group consisting of *Bacillus subtilis, B. amyloliquefaciens, B. licheniformis, B. puntis, B. megaterium, B. halodurans, B. pumilus, Gluconobacter oxydans, Caulobacter crescentus* CB 15, *Methylobacterium extorquens, Rhodobacter sphaeroides, Pseudomonas zeaxanthinifaciens, Pseudomonas putida, Pseudomonas fluorescens, Paracoccus denitrificans, Escherichia coli, Corynebacterium glutamicum, Staphylococcus carnosus, Streptomyces lividans, Streptomyces clavuligerus, Sinorhizobium melioti* and *Rhizobium radiobacter*.

A host cell according to the invention may be a eukaryotic host cell. Preferably, the eukaryotic host cell is a mammalian, insect, plant, fungal, or algal cell. More preferably, the eukaryotic host cell is a fungal cell. A suitable fungal host cell may for instance belong to genera *Saccharomyces, Schizosaccharomyces, Aspergillus, Penicillium, Pichia, Kluyveromyces, Yarrowia, Candida, Hansenula, Humicola, Issatchenkia, Kloeckera, Schwanniomyces, Torulaspora, Trichosporon, Brettanomyces, Rhizopus, Zygosaccharomyces, Pachysolen* or *Yamadazyma*. A fungal cell may for instance belong to a species of *Saccharomyces cerevisiae, S. uvarum, S. bayanus S. pastorianus, S. carlsbergensis, Aspergillus niger, Penicillium chrysogenum, Pichia stipidis, P. pastoris, Kluyveromyces marxianus, K. lactis, K. thermotolerans, Yarrowia lipolytica, Candida sonorensis, C. revkaufi, C. pulcherrima, C. tropicalis, C. utilis, C. kruisei, C. glabrata, Hansenula polymorpha, Issatchenkia orientalis, Torulaspora delbrueckii, Brettanomyces bruxellensis, Rhizopus oryzae* or *Zygosaccharomyces bailii*. In one embodiment, a fungal host cell of the present invention is a yeast, for instance belonging to a *Saccharomyces* sp., such as a *Saccharomyces cerevisiae*.

Examples of specific yeast host cells include *C. sonorensis, K. marxianus, K. thermotolerans, C. methanesorbosa, Saccharomyces bulderi* (*S. bulden*), *I. orientalis, C. lambica, C. sorboxylosa, C. zemplinina, C. geochares, P. membranifaciens, Z. kombuchaensis, C. sorbosivorans, C. vanderwaltii, C. sorbophila, Z. bisporus, Z. lentus, Saccharomyces bayanus* (*S. bayanus*), *D. casteffii, C, boidinii, C. etchellsii, K. lactis, P. jadinii, P. anomala, Saccharomyces cerevisiae* (*S. cerevisiae*), *Pichia galeiformis, Pichia* sp. YB-4149 (NRRL designation), *Candida ethanolica, P. deserticola, P. membranifaciens, P. fermentans* and *Saccharomycopsis crataegensis* (*S. crataegensis*). Suitable strains of *K. marxianus* and *C. sonorensis* include those described in WO 00/71738 A1, WO 02/42471 A2, WO 03/049525 A2, WO 03/102152 A2 and WO 03/102201A2. Suitable strains of *I. orientalis* are ATCC strain 32196 and ATCC strain PTA-6648. In the invention, the host cell may be a Crabtree negative as a wild-type strain. The Crabtree effect is defined as the occurrence of fermentative metabolism under aerobic conditions due to the inhibition of oxygen consumption by a microorganism when cultured at high specific growth rates (long-term effect) or in the presence of high concentrations of glucose (short-term effect). Crabtree negative phenotypes do not exhibit this effect, and are thus able to consume oxygen even in the presence of high concentrations of glucose or at high growth rates.

The eukaryotic cell may be a filamentous fungal host cell. Filamentous fungi include all filamentous forms of the subdivision *Eumycota* and *Oomycota* (as defined by *Hawks-* worth et al., In, *Ainsworth and Bisby's Dictionary of The Fungi*, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete Podospora, Pycnoporus, Rhizopus, Schizophyllum, Sordaria, Talaromyces, Rasamsonia, Thermoascus, Thielavia, Tolypocladium, Trametes* and *Trichoderma*. Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla*. Reference host cells for the comparison of fermentation characteristics of transformed and untransformed cells, include e.g. *Aspergillus niger* CBS120.49, CBS 513.88, *Aspergillus oryzae* ATCC16868, ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Thielavia terrestris* NRRL8126, *Talaromyces emersonii* CBS 124.902, *Rasamsonia emersonii* CBS393.64, *Acremonium chrysogenum* ATCC 36225, ATCC 48272, *Trichoderma reesei* ATCC 26921, ATCC 56765, ATCC 26921, *Aspergillus sojae* ATCC11906, *Chrysosporium lucknowense* ATCC44006 and derivatives of all of these strains.

A more preferred host cell belongs to the genus *Aspergillus*, more preferably the host cell belongs to the species *Aspergillus niger*. When the host cell according to the invention is an *Aspergillus niger* host cell, the host cell preferably is CBS 513.88, CBS124.903 or a derivative thereof.

In a preferred embodiment, a host cell according to the invention is a yeast host cell selected from the group consisting of *Candida, Hansenula, Issatchenkia, Kluyveromyces, Pichia, Saccharomyces, Schizosaccharomyces*, or *Yarrowia* strains, or a filamentous fungal host cell selected from the group consisting of filamentous fungal cells belong to a species of *Acremonium, Aspergillus, Chrysosporium, Myceliophthora, Penicillium, Talaromyces, Rasamsonia, Thielavia, Fusarium* or *Trichoderma*.

A host cell of the invention may comprise an active reductive tricarboxylic acid (TCA) pathway. The reductive TCA pathway is one of the primary pathways by which a microorganism can produce dicarboxylic acids. In recent years, introduction of the reductive TCA pathway in a host cell has proven to be the best economic option for the (microbial) production of dicarboxylic acids, e.g. succinic acid.

In one embodiment, a host cell of the invention is genetically modified to comprise a reductive TCA pathway. That is to say, the host cell of the invention may comprise a recombinant reductive TCA pathway for dicarboxylic acid production.

In yet another embodiment, a host cell of the invention is genetically modified to comprise a reductive TCA pathway which is active in the cytosol. That is to say, the host cell of the invention may comprise a recombinant reductive TCA pathway that is active in the cytosol.

In this context, the term "recombinant" refers to the fact that the TCA pathway is generated by means of recombinant gene technology well established in the art.

The enzymes involved in said reductive TCA pathway may be homologous or heterologous enzymes.

In one preferred embodiment, said reductive TCA pathway comprises the conversion of phosphoenolpyruvate or pyruvate to succinate.

Accordingly, a host cell of the invention may comprise homologous or heterologous enzymes selected from the group of enzymes catalyzing the reactions of:
pyruvate to oxaloacetate and/or phosphoenolpyruvate to oxaloacetate;
oxaloacetate to malate;
malate to fumarate; and
fumarate to succinate.

A host cell of the invention may further comprise a dicarboxylic acid transporter which exports the dicarboxylic acid, e.g. succinic acid, from inside the cell to the extracellular environment.

Accordingly, a host cell of the invention may comprise one or more copies of a nucleic acid encoding one or more of a phosphoenolpyruvate carboxykinase, a phosphoenolpyruvate carboxylase, a pyruvate carboxylase, a malate dehydrogenase, a fumarase, a fumarate reductase and/or a dicarboxylic acid transporter.

Accordingly, a host cell of the invention may overexpress one or more copies of a nucleic acid encoding one or more of a phosphoenolpyruvate carboxykinase, a phosphoenolpyruvate carboxylase, a pyruvate carboxylase, a malate dehydrogenase, a fumarase, a fumarate reductase and/or a dicarboxylic acid transporter. Preferably, where one or more of such enzymes are overexpressed, they are active in the cytosol.

Preferably, a host cell of the present invention is a fungal host cell, e.g. a yeast host cell. More preferably, the fungal host cell of the invention comprises genetic modifications according to the preferred embodiments as described herein below.

The fungal host cell of the present invention may comprise a genetic modification with a pyruvate carboxylase (PYC) that catalyses the reaction from pyruvate to oxaloacetate (EC 6.4.1.1). The pyruvate carboxylase may for instance be active in the cytosol upon expression of the gene. For instance, the fungal host cell overexpresses a pyruvate carboxylase, for instance an endogenous or homologous pyruvate carboxylase is overexpressed. The fungal host cell according to the present invention may be genetically modified with a pyruvate carboxylase which has at least 70%, preferably at least 75%, 80%, 85%, 90%, 91%, 92%, 93%, 94%, 95%, 96%, 97%, 98%, 99% or 100% sequence identity with amino acid sequence encoded by the nucleic acid sequence of SEQ ID NO: 16.

Preferably, the fungal host cell of the present invention expresses a nucleotide sequence encoding a phosphoenolpyruvate (PEP) carboxykinase in the cytosol. Preferably, a nucleotide sequence encoding a PEP carboxykinase is overexpressed. The PEP carboxykinase (EC 4.1.1.49) preferably is a heterologous enzyme, preferably derived from bacteria, more preferably the enzyme having PEP carboxykinase activity is derived from *Escherichia coil, Mannheimia* sp., *Actinobacillus* sp., or *Anaerobiospirillum* sp., more preferably *Mannheimia succiniciproducens*. A gene encoding a PEP carboxykinase may be overexpressed and active in the cytosol of a fungal cell. Preferably, a fungal host cell according to the present invention is genetically modified with a PEP carboxykinase which has at least 70%, preferably at least 75%, 80%, 85%, 90%, 91%, 92%, 93%, 94%, 95%, 96%, 97%, 98%, 99% or 100% sequence identity with amino acid sequence of SEQ ID NO: 14.

Preferably, the fungal host cell of the present invention expresses a nucleotide sequence encoding a phosphoenolpyruvate (PEP) carboxylase in the cytosol. Preferably a nucleotide sequence encoding a PEP carboxylase is overexpressed. The PEP carboxylase (EC 4.1.1.31) preferably is a heterologous enzyme, preferably derived from bacteria.

In one embodiment, the fungal host cell of the present invention is further genetically modified with a gene encoding a malate dehydrogenase (MDH) active in the cytosol upon expression of the gene. Cytosolic expression may be obtained by deletion of a peroxisomal targeting signal. The malate dehydrogenase may be overexpressed. A cytosolic MDH may be any suitable homologous or heterologous malate dehydrogenase, catalyzing the reaction from oxaloacetate to malate (EC 1.1.1.37), for instance derived from *S. cerevisiae*.

Preferably, the MDH is *S. cerevisiae* MDH3, more preferably one which has a C-terminal SKL deletion such that it is active in the cytosol. Preferably, the fungal host cell of the present invention comprises a nucleotide sequence encoding a malate dehydrogenase that has at least 70%, preferably at least 75%, 80%, 85%, 90%, 91%, 92%, 93%, 94%, 95%, 96%, 97%, 98%, 99% or 100% sequence identity with the amino acid sequence of SEQ ID NO: 15.

In another embodiment, the fungal host cell of the present invention is further genetically modified with a gene encoding a fumarase, that catalyses the reaction from malic acid to fumaric acid (EC 4.2.1.2). A gene encoding fumarase may be derived from any suitable origin, preferably from microbial origin, for instance a yeast such as *Saccharomyces* or a filamentous fungus, such *Rhizopus oryzae*, or a bacterium such a *Escherichia coli*. The fungal host cell of the present invention may overexpress a nucleotide sequence encoding a fumarase. The fumarase may be active in the cytosol upon expression of the nucleotide sequence, for instance by deleting a peroxisomal targeting signal. It was found that cytosolic activity of a fumarase resulted in a high productivity of a dicarboxylic acid by the fungal cell.

Preferably, the fungal host cell of the present invention overexpresses a nucleotide sequence encoding a fumarase that has at least 70%, preferably at least 75%, 80%, 85%, 90%, 91%, 92%, 93%, 94%, 95%, 96%, 97%, 98%, 99% or 100% sequence identity with the amino acid sequence of SEQ ID NO: 1, SEQ ID NO: 13 or SEQ ID NO: 70.

In another embodiment, the fungal host cell of the invention is genetically modified with any suitable heterologous or homologous gene encoding a NAD(H)-dependent fumarate reductase, catalyzing the reaction from fumarate to succinate (EC 1.3.1.6). The NADH-dependent fumarate reductase may be a heterologous enzyme, which may be derived from any suitable origin, for instance bacteria, fungi, protozoa or plants. A fungal cell of the present disclosure comprises a heterologous NAD(H)-dependent fumarate reductase, preferably derived from a *Trypanosoma* sp, for instance a *Trypanosoma brucei*. In one embodiment, the NAD(H)-dependent fumarate reductase is expressed and active in the cytosol, for instance by deleting a peroxisomal targeting signal. The fungal cell may overexpress a gene encoding a NAD(H)-dependent fumarate reductase.

Preferably, the fungal host cell according to the present invention is genetically modified with a NAD(H)-dependent fumarate reductase, which has at least at least 70%, preferably at least 75%, 80%, 85%, 90%, 91%, 92%, 93%, 94%, 95%, 96%, 97%, 98%, 99% or 100% sequence identity with the amino acid sequence of SEQ ID NO: 12.

In another embodiment, the fungal host cell of the present invention is genetically modified with a variant polypeptide having fumarate reductase activity as disclosed in WO2015/086839.

In another embodiment, the fungal host cell of the invention expresses a nucleotide sequence encoding a dicarboxylic acid transporter protein. Preferably, the dicarboxylic acid transporter protein is overexpressed. A dicarboxylic acid transporter protein may be any suitable homologous or heterologous protein. Preferably, the dicarboxylic acid transporter protein is a heterologous protein. A dicarboxylic acid transporter protein may be derived from any suitable organism, preferably from yeast or fungi such as *Schizosaccharomyces pombe* or *Aspergillus niger*. Preferably, a dicarboxylic acid transporter protein is a dicarboxylic acid transporter/malic acid transporter protein, e.g. from *Aspergillus niger* which at least 70%, preferably at least 75%, 80%, 85%, 90%, 91%, 92%, 93%, 94%, 95%, 96%, 97%, 98%, 99% or 100% sequence identity with the amino acid sequence of SEQ ID NO: 19.

The fungal host cell of the invention may further comprise a genetic modification with a gene encoding an isocitrate lyase (EC 4.1.3.1), which may be any suitable heterologous or homologous enzyme. The isocitrate lyase may for instance be obtained from *Kluyveromyces lactis* or *Escherichia coli*.

The fungal host cell according to the present invention is genetically modified with a isocitrate lyase which has at least 70%, preferably at least 75%, 80%, 85%, 90%, 91%, 92%, 93%, 94%, 95%, 96%, 97%, 98%, 99% or 100% sequence identity with amino acid sequence encoded by the nucleic acid sequence of SEQ ID NO: 17.

The fungal host cell of the present invention may further comprise a genetic modification with a malate synthase (EC 2.3.3.9). The malate synthase may be overexpressed and/or active in the cytosol, for instance by deletion of a peroxisomal targeting signal. In the event the malate synthase is a *S. cerevisiae* malate synthase, for instance the native malate synthase is altered by the deletion of the SKL carboxyterminal sequence.

The fungal host cell of the present invention is genetically modified with a malate synthase which at least 70%, preferably at least 75%, 80%, 85%, 90%, 91%, 92%, 93%, 94%, 95%, 96%, 97%, 98%, 99% or 100% sequence identity with amino acid sequence encoded by the nucleic acid sequence of SEQ ID NO: 18.

In another embodiment, the fungal host cell of the invention disclosed herein comprises a disruption of a gene encoding a pyruvate decarboxylase (EC 4.1.1.1), catalyzing the reaction from pyruvate to acetaldehyde.

Preferably, the fungal host cell of the present invention may overexpress a homologous or heterologous nucleotide sequence comprising sequence encoding one or more of a PEP carboxykinase, a PEP carboxylase, a pyruvate carboxylase, a malate dehydrogenase, a fumarase, a fumarate reductase, and/or a dicarboxylic acid transporter. More preferably, where one or more of such enzymes are overexpressed they are active in the cytosol. Preferred embodiments of the enzymes are as described herein above.

Preferably, the fungal host cell of the present invention is a yeast host cell. Preferred embodiments of the yeast host cell are as described herein above for the fungal host cell.

Cytosolic expression of the enzymes described above may be obtained by deletion of a peroxisomal or mitochondrial targeting signal. The presence of a peroxisomal or mitochondrial targeting signal may for instance be determined by the method disclosed by *Schlüter et al., Nucleid Acid Research* 2007, 35, D815-D822.

Standard genetic techniques, such as overexpression of enzymes in the host cells, genetic modification of host cells, or hybridisation techniques, are known methods in the art, such as described in *Sambrook and Russel* (2001) *"Molecular Cloning: A Laboratory Manual* (3$^{rd}$ *edition), Cold Spring Harbor Laboratory, Cold Spring Harbor Laboratory Press* or F. *Ausubel et al, eds., "Current protocols in molecular biology", Green Publishing and Wiley Interscience, New York* (1987). Methods for transformation, e.g. genetic modification of fungal host cells, are known from e.g. EP-A-0 635 574, WO 98/46772, WO 99/60102 and WO 00/37671, WO90/14423, EP-A-0481008, EP-A-0635 574 and U.S. Pat. No. 6,265,186.

A comparison of sequences and determination of percentage of sequence identity between two sequences can be accomplished using a mathematical algorithm. The skilled person will be aware of the fact that several different computer programs are available to align two sequences and determine the identity between two sequences (*Kruskal, J. B.* (1983) *An overview of sequence comparison In D. Sankoff and J. B. Kruskal,* (ed.), *Time warps, string edits and macromolecules: the theory and practice of sequence comparison, pp.* 1-44 *Addison Wesley*). The percent sequence identity between two amino acid sequences or between two nucleotide sequences may be determined using the Needleman and Wunsch algorithm for the alignment of two sequences (*Needleman, S. B. and Wunsch, C. D.* (1970) *J. Mol. Biol.* 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, *EMBOSS: The European Molecular Biology Open Software Suite* (2000) Rice, P. Longden, I. and Bleasby, A. *Trends in Genetics* 16, (6) *pp* 276-277, *http://emboss.bioinformatics.nl/*). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the blastn and blastx programs (version 2.2.31 or above) of *Altschul, et al.* (1990) *J. Mol. Biol.* 215:403-10. BLAST nucleotide searches can be performed with the blastn program, score=100, word-size=11 to obtain nucleotide sequences homologous to nucleic acid molecules of the invention. BLAST protein searches can be performed with the blastx program, score=50, word-size=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., blastx and blastn) can be used. See the homepage of the National Center for Biotechnology Information at *http://www.ncbi.nlm.nih.gov/*.

According to the present invention, there is provided a method for improving dicarboxylic acid production in a host cell, which method comprises:

providing a host cell capable of producing a dicarboxylic acid; and modifying the host cell in its genome to result in a deficiency in the oxidation of one or more cofactor, thereby to improve dicarboxylic acid production in the host cell.

Preferred embodiments of the host cell capable of producing a dicarboxylic acid and of the genetic modifications resulting in a deficiency in the oxidation of one or more cofactor are as described herein above.

According to the present invention, there is also provided a process for the production of a dicarboxylic acid which process comprises fermenting the host cell of the invention as described herein above, under conditions suitable for production of the dicarboxylic acid, and optionally, recovering the dicarboxylic acid from the fermentation medium.

In the process, the host cell of the invention is fermented in a vessel comprising a suitable fermentation medium. The term fermenting, fermentation or fermented and the like as used herein refers to the cell (e.g. microbial) production of compounds, here dicarboxylic acids from carbohydrates.

Preferably, the fermentation product is a dicarboxylic acid, preferably malic acid, fumaric acid and/or succinic acid, preferably succinic acid.

A batch fermentation is defined herein as a fermentation wherein all nutrients are added at the start of a fermentation.

A fed-batch fermentation is a batch fermentation wherein the nutrients are added during the fermentation. Products in a batch and fed-batch fermentation may be harvested at a suitable moment, for instance when one or more nutrients are exhausted.

A continuous fermentation is a fermentation wherein nutrients are continuously added to the fermentation and wherein products are continuously removed from the fermentation.

In one embodiment, fermenting the host cell of the invention in the process of the invention is carried out under carbohydrate limiting conditions. As used herein, carbohydrate limiting conditions are defined as maintaining the carbohydrate concentration below 10 g/l, for example about 5 g/l.

The process for the production of dicarboxylic acid according to the present invention may be carried out in any suitable volume and scale, preferably on an industrial scale. Industrial scale is defined herein as a volume of at least 10, or 100 litres, preferably at least 1 cubic metre, preferably at least 10, or 100 cubic metres, preferably at least 1000 cubic metres, usually below 10,000 cubic metres.

Fermenting the host cell of the invention in the process of the invention may be carried out in any suitable fermentation medium comprising a suitable nitrogen source, carbohydrate and other nutrients required for growth and production of a dicarboxylic acid in the process of the invention. A suitable carbohydrate in the fermentation process according to the invention may be glucose, galactose, xylose, arabinose, sucrose, or maltose.

In one embodiment, the fermentation process is carried out under a partial $CO_2$ pressure of between 5% and 60%, preferably about 50%.

The pH during the process for the production of dicarboxylic acid usually lowers during the production of the dicarboxylic acid. Preferably, the pH in the process for the production of dicarboxylic acid ranges between 1 and 5, preferably between 1.5 and 4.5, more preferably between 2 and 4.

In another preferred embodiment, the process according to the present invention comprises a step of pre-culturing the host cell of the present invention under aerobic conditions in the presence of a carbohydrate. Preferably, the fermentation of the host cell during pre-culturing is carried out at a pH of between 4 and 6. Preferably, the carbohydrate during pre-culturing is a non-repressing carbohydrate, preferably galactose. It has been found advantageous to pre-culture host cells on a non-repressing carbohydrate, since this prevents glucose repression occurring, which may negatively influence the amount of biomass produced. In addition, it has been found that a step of pre-culturing host cells under aerobic conditions results in a higher biomass yield and a faster growth. Preferably, the pre-culturing is carried out in batch mode.

A propagation step for producing increased biomass is typically carried out, preferably under carbohydrate limiting conditions.

The process for producing a dicarboxylic acid may be carried out at any suitable temperature. A suitable temperature may for instance be between about 10 and about 40 degrees Celsius, for instance between about 15 and about 30 degrees Celsius.

In an embodiment, the process of the invention is carried out in such a way that at least a portion of the host cells of the present invention is re-used, i.e. recycled. The host cells may be recycled back into the original vessel or into a second vessel. Preferably, the medium into which the recycled host cells are introduced is supplemented with a vitamin and/or a trace element.

In a preferred embodiment, the fermentation medium comprises an amount of dicarboxylic acid, such as succinic acid, of between 1 and 150 g/l, preferably between 5 and 100 g/l, more preferably between 10 and 80 g/l or between 15 and 60 g/l. In any event, the host cell of the present invention will typically be capable of accumulating more dicarboxylic acid in the fermentation medium as compared to the parent host cell that has not been modified in its genome according to the invention (and when analysed under substantially identical conditions). The host cell of the invention will typically display an increase in the titer of a dicarboxylic acid, e.g. succinic acid, by at least 1%, more preferably by at least 2%, even more preferably by at least 4%, in particular by at least 5%, more in particular by at least 6%, for example by at least 8%, for example by at least 10%, as compared to the parent host cell that has not been modified in its genome according to the invention (and when analysed under substantially identical conditions). In this context, the titer of a dicarboxylic acid (g dicarboxylic acid/l supernatant) is calculated by dividing the amount of produced dicarboxylic acid by the total volume of culture supernatant.

In a further preferred embodiment, the host cell of the invention will typically display an increase in the fermentation yield of a dicarboxylic acid, e.g. succinic acid, by at least 1%, more preferably by at least 2%, even more preferably by at least 4%, in particular by at least 5%, more in particular by at least 6%, for example by at least 8%, for example by at least 10%, as compared to the parent host cell that has not been modified in its genome according to the invention (and when analysed under substantially identical conditions). In this context, the fermentation yield of a dicarboxylic acid (g dicarboxylic acid/g glucose) is calculated by dividing the amount of produced dicarboxylic acid by the total amount of consumed sugars, including during the biomass propagation phase.

The process for the production of a dicarboxylic acid may further comprise recovering the dicarboxylic acid. Recovery of the dicarboxylic acid may be carried out by any suitable method known in the art, for instance by crystallization, ammonium precipitation, ion exchange technology, centrifugation or filtration or any suitable combination of these methods.

In a preferred embodiment, the recovery of the dicarboxylic acid comprises crystallizing the dicarboxylic acid and forming dicarboxylic acid crystals. Preferably, the crystallizing of the dicarboxylic acid comprises removing part of the fermentation medium, preferably by evaporation, to obtain a concentrated medium.

According to the present invention, the dicarboxylic acid, such as succinic acid, may be recovered by crystallizing the dicarboxylic acid, such as succinic acid, from an aqueous solution having a pH of between 1 and 5 and comprising said dicarboxylic acid, comprising evaporating part of the aqueous solution to obtain a concentrated solution, lowering the temperature of the concentrated solution to a value of between 5 and 35 degrees Celsius, wherein dicarboxylic acid crystals are formed. Preferably, the crystallizing comprises bringing the temperature of the concentrated medium to a temperature of between 10 and 30 degrees Celsius, preferably between 15 and 25 degrees Celsius. Preferably, the aqueous solution comprising the dicarboxylic acid has a pH of between 1.5 and 4.5, preferably between 2 and 4.

It has been found that crystallizing the dicarboxylic acid, such as succinic acid, at higher temperatures such as between 10 and 30 degrees Celsius results in crystals of a dicarboxylic acid, such as succinic acid, with a lower amount of impurities such as organic acid, protein, color and/or odor, than crystals of a dicarboxylic acid, such as succinic acid, that were crystallized at a low temperature of below 10 degrees.

Another advantage of crystallizing the dicarboxylic acid, such as succinic acid, at a higher temperature is that it requires a lower amount of energy for cooling the aqueous solution as compared to a process wherein crystallizing the dicarboxylic acid is carried out below 10 or 5 degrees Celsius, resulting in a more economical and sustainable process.

Preferably, the crystallizing of the dicarboxylic acid, such as succinic acid, comprises a step of washing the dicarboxylic acid crystals. Dicarboxylic acid, such as succinic acid, may be crystallized directly from the fermentation medium having a pH of between 1 and 5 to a purity of at least 90% w/w, preferably at least 95, 96, 97, or at least 98%, or 99 to 100% w/w.

In a preferred embodiment, the process for the production of a dicarboxylic acid further comprises using the dicarboxylic acid in an industrial process.

Preferably, the dicarboxylic acid, such as succinic acid, that is prepared in the process according to the present invention is further converted into a desirable product. A desirable product may for instance be a polymer, such as polybutylene succinic acid (PBS), a deicing agent, a food additive, a cosmetic additive or a surfactant. That is to say, the invention provides a method for the production of a product, for example, a polymer, such as polybutylene succinic acid (PBS), a deicing agent, a food additive, a cosmetic additive or a surfactant, which method comprises: producing a dicarboxylic acid as described herein; and using said dicarboxylic acid in the production of said product.

According to the present invention, there is also provided a use of a modification in the genome of a host cell to result in a deficiency of at least one enzymatic step catalysing the oxidation of a cofactor, thereby to increase dicarboxylic acid production in the host cell. Preferred embodiments for the genetic modifications and the host cells are as described herein above.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

General Materials and Methods
DNA Procedures

Standard DNA procedures were carried out as described elsewhere (Sambrook et al., 1989, Molecular cloning: a laboratory manual, 2nd Ed., Cold Spring Harbor Laboratory Press, Cold Spring Harbor, N.Y.) unless otherwise stated. DNA was amplified using the proofreading enzyme Phusion polymerase (Finnzymes). Restriction enzymes were from Invitrogen or New England Biolabs.

MTP Fermentation of Succinic Acid Poduction Strains

To determine succinic acid production, strains were grown in triplicate in microtiter plates (MTP) in humidity shakers (Infors) for 3 days at 30 degrees at 550 rpm and 80% humidity. The medium was based on Verduyn medium (Verduyn C, Postma E, Scheffers W A, Van Dijken J P. Yeast, 1992 July; 8(7):501-517), but modifications in carbon and nitrogen source were made as described herein below.

TABLE 1

MTP pre-culture medium composition

| Raw material | | Concentration (g/l) |
|---|---|---|
| Galactose | $C_6H_{12}O_6 \cdot H_2O$ | 40.00 |
| Urea | $(NH_2)_2CO$ | 2.30 |
| Potassium dihydrogen phosphate | $KH_2PO_4$ | 3.00 |
| Magnesium sulphate | $MgSO_4 \cdot 7H_2O$ | 0.50 |
| Trace element solution[a] | | 1.00 |
| Vitamin solution[b] | | 1.00 |

| Component | Formula | Concentration (g/kg) |
|---|---|---|
| [a]Trace elements solution | | |
| EDTA | $C_{10}H_{14}N_2Na_2O_8 \cdot 2H_2O$ | 15.00 |
| Zincsulphate•7H2O | $ZnSO_4 \cdot 7H_2O$ | 4.50 |
| Manganesechloride•2H2O | $MnCl_2 \cdot 2H_2O$ | 0.84 |
| Cobalt (II) chloride•6H2O | $CoCl_2 \cdot 6H_2O$ | 0.30 |
| Copper (II) sulphate•5H2O | $CuSO_4 \cdot 5H_2O$ | 0.30 |
| Sodium molybdenum•2H2O | $Na_2MoO_4 \cdot 2H_2O$ | 0.40 |
| Calciumchloride•2H2O | $CaCl_2 \cdot 2H_2O$ | 4.50 |
| Ironsulphate•7H2O | $FeSO_4 \cdot 7H_2O$ | 3.00 |

TABLE 1-continued

MTP pre-culture medium composition

| Boric acid | $H_3BO_3$ | 1.00 |
|---|---|---|
| Potassium iodide | KI | 0.10 |
| [b]Vitamin solution | | |
| Biotin (D−) | $C_{10}H_{16}N_2O_3S$ | 0.05 |
| Ca D(+) panthothenate | $C_{18}H_{32}CaN_2O_{10}$ | 1.00 |
| Nicotinic acid | $C_6H_5NO_2$ | 1.00 |
| Myo-inositol | $C_6H_{12}O_6$ | 25.00 |
| Thiamine chloride hydrochloride | $C_{12}H_{18}Cl_2N_4OS \cdot xH_2O$ | 1.00 |
| Pyridoxol hydrochloride | $C_8H_{12}ClNO_3$ | 1.00 |
| p-aminobenzoic acid | $C_7H_7NO_2$ | 0.20 |

A total of 80 microliters of pre-culture was used to inoculate 2.5 ml of medium with 1.5% galactose as carbon source in 24-well plates. The cultures were grown for 72 hours in humidity shakers (Infors) at 30° C., 550 rpm, 80% humidity. After generating biomass, a production experiment was started by re-suspending cells into 2.5 ml of mineral medium with glucose as carbon source. The main cultures were incubated in humidity shakers (Infors) at 30 degrees at 550 rpm and 80% humidity and samples were taken after 48 hours of cultivation.

Metabolite Analysis of MTP Samples by NMR

For metabolite analysis of MTP samples, 90 microliter of supernatant of fermentation samples is mixed with 10 microliter of NMR standard (20 g/l maleic acid) and 100 microliter of 10% D2O solution. The samples are lyophilized and subsequently dissolved in 1 mL D2O.

1D 1H NMR spectra are recorded on a BEST Bruker Avance III spectrometer, operating at a proton frequency of 500 MHz, equipped with a He-cooled cryo probe, using a pulse program without water suppression (ZG) at a temperature of 300 K, with a 90 degree excitation pulse, acquisition time of 2.0 seconds and a relaxation delay of 40 seconds. The number of scans was set at 8, dummy scans are not used.

The Succinic acid concentration [in g/L] is calculated based on the following signals (δ relative to 4,4-dimethyl-4-silapentane-1-sulfonic acid):

Succinic acid: succinic acid signal at 2.67 ppm (s, 4H)
The signal used for the standard: maleic acid peak around 6.3 ppm (S, 2H)

Example 1

Construction of Yeast Strain SUC-947

The Saccharomyces cerevisiae strain SUC-632 was constructed as described in WO2013/004670. Strain SUC-632 was used as a starting point to construct strain SUC-947. Strain SUC-708 is a mutant of strain SUC-632 obtained by classical strain improvement.

A fumarase gene of E. coli (fumB) was transformed into strain SUC-708 as described below. SEQ ID NO: 1 describes the fumarase (fumB) protein sequence from Escherichia coli (E.C. 4.2.1.2, UniProt accession number P14407). The gene sequence was codon pair optimized for expression in S. cerevisiae as disclosed in patent application WO2008/000632. The stop codon TAA was modified to TAAG. Expression of the FUM_01 gene is controlled by the TDH1 promoter (600 bp directly before the start codon of the TDH1 gene) and the TDH1 terminator (300 bp directly after the stop codon of the TDH1 gene). The TDH1 promoter and TDH1 terminator sequences controlling expression of FUM_01 are native sequences derived from Saccharomyces cerevisiae S288C. The synthetic promoter-gene sequence including appropriate restriction sites was synthesized by GenArt (Regensburg, Germany). This synthetic fragment is part of plasmid pSUC223 (FIG. 1). The complete sequence of pSUC223 is described in SEQ ID NO: 2. Plasmid pSUC223 contains a KanMX marker with allows for selection for growth in the presence of G418. The KanMX marker, flanked by lox66 and lox71 sites (*Albert et al., Plant Journal*, 7(4), 649-659), can be removed by the action of Cre-recombinase, as described by Gueldender et al., (*Nucleic Acids Res.* 1996 Jul. 1; 24(13):2519-24). The TDH1p-fumB-TDH1t and the lox66-KanMX-lox71 sequences were flanked by sequences that allow integration by double cross-over at the YPRCtau3 locus, which is located on chromosome XVI.

Plasmid pSUC223 was restricted using restriction enzymes ApaLI and XhoI. A y5.408 bp fragment containing the 5' YPRCtau3 flank, the synthetic fumB construct, the KanMX selection marker flanked by lox66 and lox71 sites and the 3' YPRCtau3 flank was excised from an agarose gel and purified using the Zymoclean™ Gel DNA Recovery Kit (Zymo Research, Irvine, Calif., USA) according to manufacturer's instructions.

The fragment was transformed to strain SUC-708. Transformants were selected on Yeast Extract BactoPeptone (YEP) 2% galactose plates supplemented with 200 µg G418/milliliter for selection of transformants containing the KanMX marker, yielding multiple transformants. Presence of the introduced fumB gene was confirmed by PCR using primer sequences that can anneal to the coding sequences of the ORF encoded by SEQ ID NO: 2. One of the correct transformants, SUC-708 FUM_01 #3, was named SUC-813.

Fumarate reductase FRD1 of *S. cerevisiae* encoded by YEL047C, E.C. 1.3.1.6, UniProt accession number P32614, was analyzed for the presence of signal sequences using SignalP 3.0 (http://www.cbs.dtu.dk/services/SignalP/) (*Bendtsen et al.*, 2004, Mol. Biol., 340:783-795) and TargetP 1.1 (http://www.cbs.dtu.dk/services/TargetP/) (*Emanuelsson et al.*, 2007, Nature Protocols 2, 953-971). The *S. cerevisiae* Frd1 protein has multiple possible localizations. It contains a predicted 19 amino acid signal peptide. After removal of the putative SP, the predicted tendency for cytosolic localization was drastically increased. The variant omitting the 19 amino acid signal peptide is described in SEQ ID NO: 3, which was subjected to the codon-pair method as disclosed in WO2008/000632 for expression in *S. cerevisiae*. The stop codon TAA was modified to TAAG. Expression of the FRD1 gene is controlled by the TDH3 promoter (600 bp directly before the start codon of the TDH3 gene) and the TDH3 terminator (300 bp directly after the stop codon of the TDH3 gene). The TDH3 promoter and TDH3 terminator sequences controlling expression of FRD1 are native sequences derived from *Saccharomyces cerevisiae* S288C. The synthetic promoter-gene sequence including appropriate restriction sites was synthesized by DNA2.0 (Menlo Park, Calif., USA) and is described in SEQ ID NO: 4.

Figure 2:
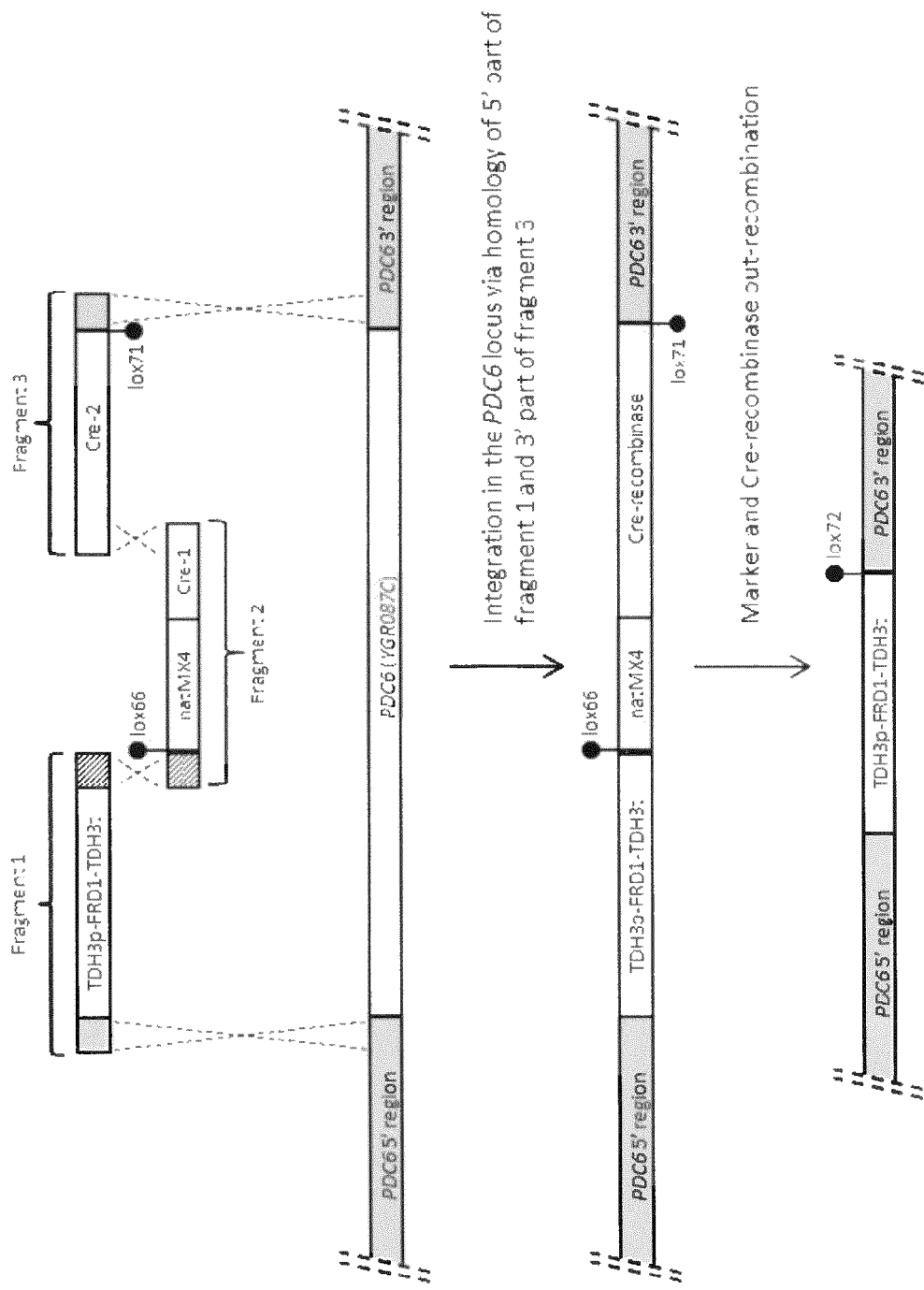
FIG. 2 sets out a schematic depiction of the principle of PDC6 replacement by a FRD1 expression cassette.
Figure 3:
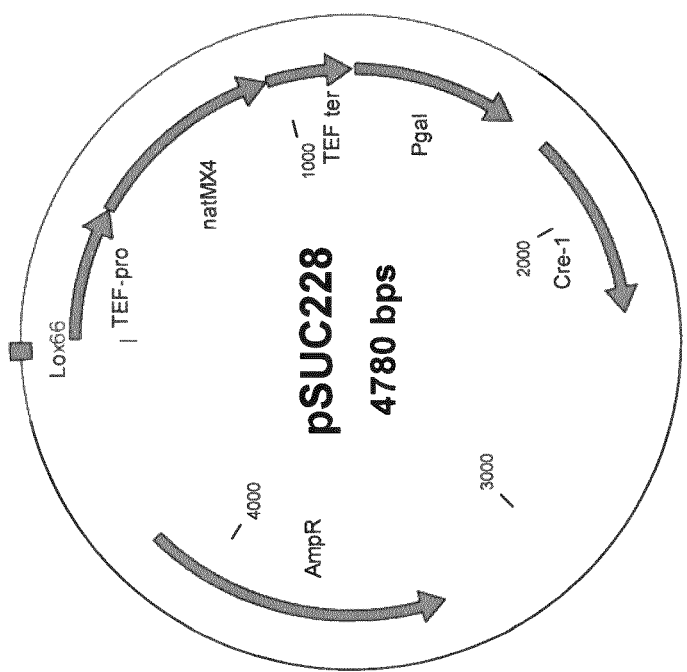
FIG. 3 sets out the plasmid map of pSUC 228.

The modified FRD1 gene was transformed into strain SUC-813 as depicted in FIG. 2. The modified FRD1 gene replaced the PDC6 gene in strain SUC-813 using the "split Cre recombinase integration" or "direct Cre recombinase integration" (DCI) approach as described in PCT/EP2013/055047. PCR fragments were generated using Phusion DNA polymerase (New England Biolabs, USA) according to manufacturer's instructions. PCR fragment 1 was generated by using the primer sequences described in SEQ ID NO: 5 and SEQ ID NO: 6, using a cloning plasmid of DNA 2.0 containing SEQ ID NO: 4 as template. SEQ ID NO: 5 contains a 66 bp overlap with the 5' region of the PDC6 gene, directly located before the start codon of the PDC6 gene. PCR fragment 2 was generated by using the primer sequences described in SEQ ID NO: 7 and SEQ ID NO: 8 using plasmid pSUC228 (FIG. 3, SEQ ID NO: 9) as template. Plasmid pSUC228 is a modified version of pSUC227, which is described in PCT/EP2013/055047. Plasmid pSUC227 contains a KanMX marker, which is replaced by a nourseothricin (natMX4) marker (Goldstein and McCusker, Yeast. 1999 October; 15(14):1541-53) resulting in pSUC228. PCR fragment 3 was generated by using the primer sequences described in SEQ ID NO: 10 and SEQ ID NO: 11, using pSUC225 (described in PCT/EP2013/055047) as template. SEQ ID NO: 11 contains a 64 bp overlap with the 3' region of the PDC6 gene, directly located after the stop codon of the PDC6 gene.

The size of the PCR fragments was checked with standard agarose electrophoresis techniques. PCR amplified DNA fragments were purified using the Zymoclean™ Gel DNA Recovery Kit (Zymo Research, Irvine, Calif., USA) according to manufacturer's instructions.

Yeast transformation was done by a method known by persons skilled in the art. *S. cerevisiae* strain SUC-813 was transformed with purified PCR fragments 1, 2 and 3. PCR fragment 1 contained an overlap with PCR fragment 2 at its 3' end. PCR fragment 3 contained an overlap with PCR fragment 2 at its 5' end. PCR fragment 2 contained an overlap at its 5' end with PCR fragment 1 and at its 3' end with PCR fragment 3, such that this allowed homologous recombination of all three PCR fragments (FIG. 2). The 5' end of PCR fragment 1 and the 3' end of PCR fragment 3 were homologous to the PDC6 locus and enabled integration of all three PCR fragments in the PDC6 locus. This resulted in one linear fragment consisting of PCR fragments 1 to 3 integrated in the PDC6 locus (FIG. 2). This method of integration is described in patent application WO2013/076280.

Transformation mixtures were plated on YPD-agar (per liter: 10 grams of yeast extract, 20 grams per liter peptone, 20 grams per liter dextrose, 20 grams of agar) containing 100 µg nourseothricin (Jena Bioscience, Germany) per ml. After three to five days of growth at 30° C., individual transformants were re-streaked on fresh YPD-agar plates containing 100 µg nourseothricin per ml.

Subsequently, the marker cassette and Cre-recombinase and are effectively removed via recombination by the method described in PCT/EP2013/055047, resulting in replacement of the PDC6 gene by SEQ ID NO: 4 and leaving a lox72 site as a result of recombination between the lox66 and lox71 sites. Due to the activity of Cre-recombinase, the KanMX marker flanked by lox66 and lox71 sites, which was introduced into genomic DNA to create strain SUC-813 was also efficiently removed. The resulting markerfree strain was named SUC-947. Strain SUC-947 was able to grow on YPD-agar plates, but unable to grow on YPD-agar plates supplemented with either 200 µg G418/ml or 100 µg/ml nourseothricin or both, confirming removal of both the KanMX and the natMX4 marker.

Example 2

Construction of Yeast Strain SUP-003 and Production of Succinic Acid by SUP-003

Generation of PCR Fragments

Figure 5:
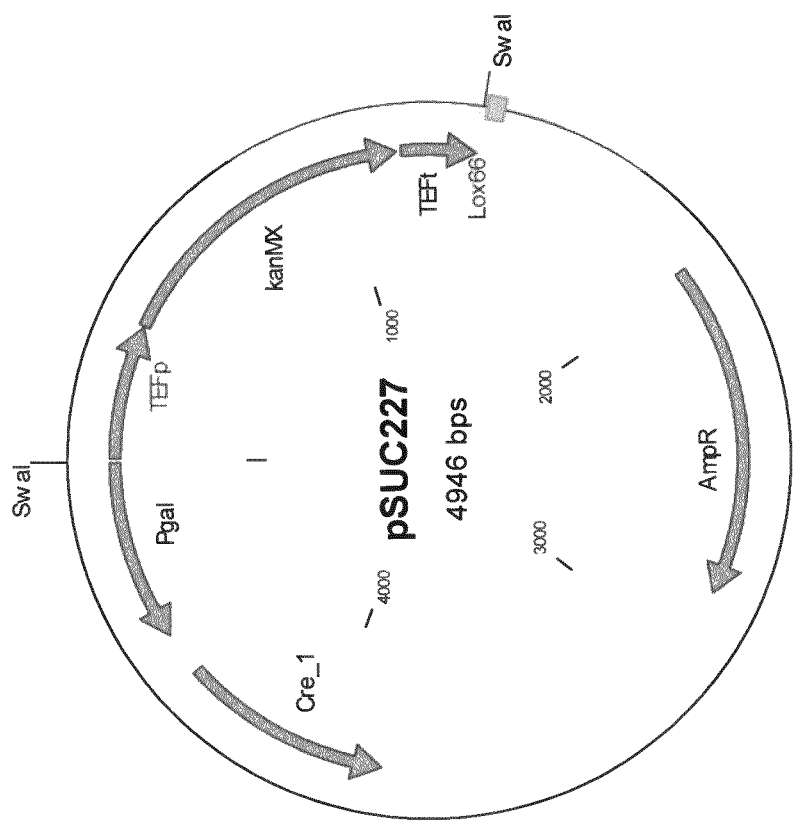
FIG. 5 sets out the plasmid map of pSUC 227.
Figure 6:
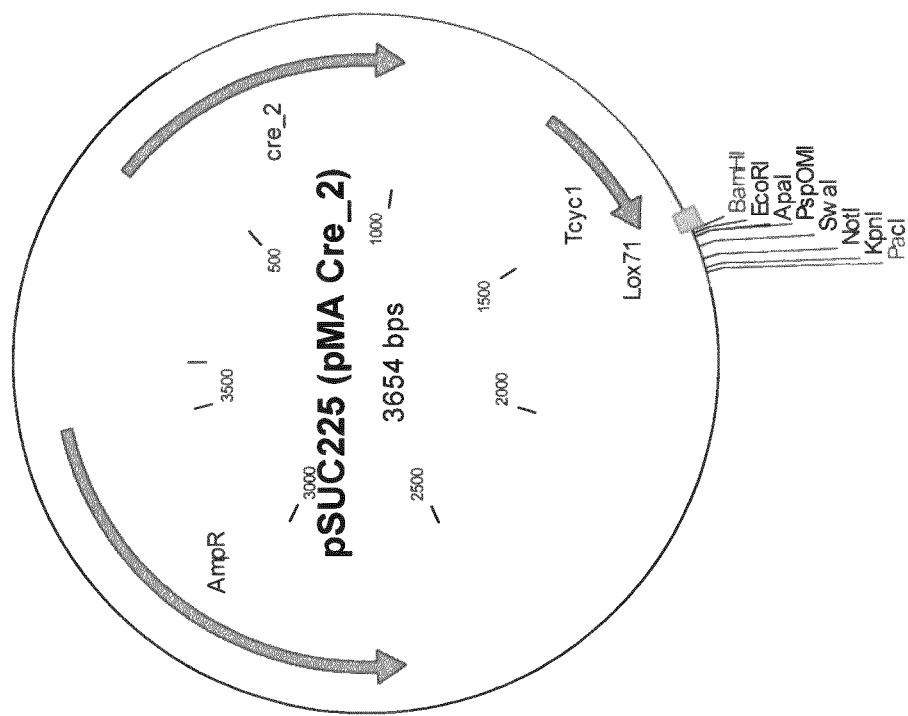
FIG. 6 sets out the plasmid map of pSUC 225.

PCR fragments were generated using Phusion DNA polymerase (New England Biolabs, USA) according to manufacturer's instructions. PCR fragment 4 was generated by using the primer sequences described in SEQ ID NO: 20 and SEQ ID NO: 21, using genomic DNA as template. SEQ ID NO: 21 contains a 27 bp overlap with the 5' region of the GUT2 gene, directly located before the start codon of the GUT2 gene. PCR fragment 5 was generated by using the primer sequences described SEQ ID NO: 22 and SEQ ID NO: 24, using plasmid pSUC227 (FIG. 5, SEQ ID NO: 43)

as template. PCR fragment 6 was generated by using the primer sequences described in SEQ ID NO: 23 and SEQ ID NO: 25, using plasmid pSUC225 (FIG. 6, SEQ ID NO: 44) as template. PCR fragment 7 was generated by using the primer sequences described in SEQ ID NO: 26 and SEQ ID NO: 27, using genomic DNA as template. SEQ ID NO: 26 contains a 29 bp overlap with the 3' region of the GUT2 gene, directly located after the stop codon of the GUT2 gene.

The size of the PCR fragments was checked with standard agarose electrophoresis techniques. PCR amplified DNA fragments were purified using the Zymoclean™ Gel DNA Recovery Kit (Zymo Research, Irvine, Calif., USA) according to manufacturer's instructions.

Transformation to Strain SUC-947 in Order to Construct Strain SUP-003

The Saccharomyces cerevisiae strain SUC-947 was constructed as described in Example 1. Strain SUC-947 was used as a starting point to construct strain SUP-003.

Figure 4:
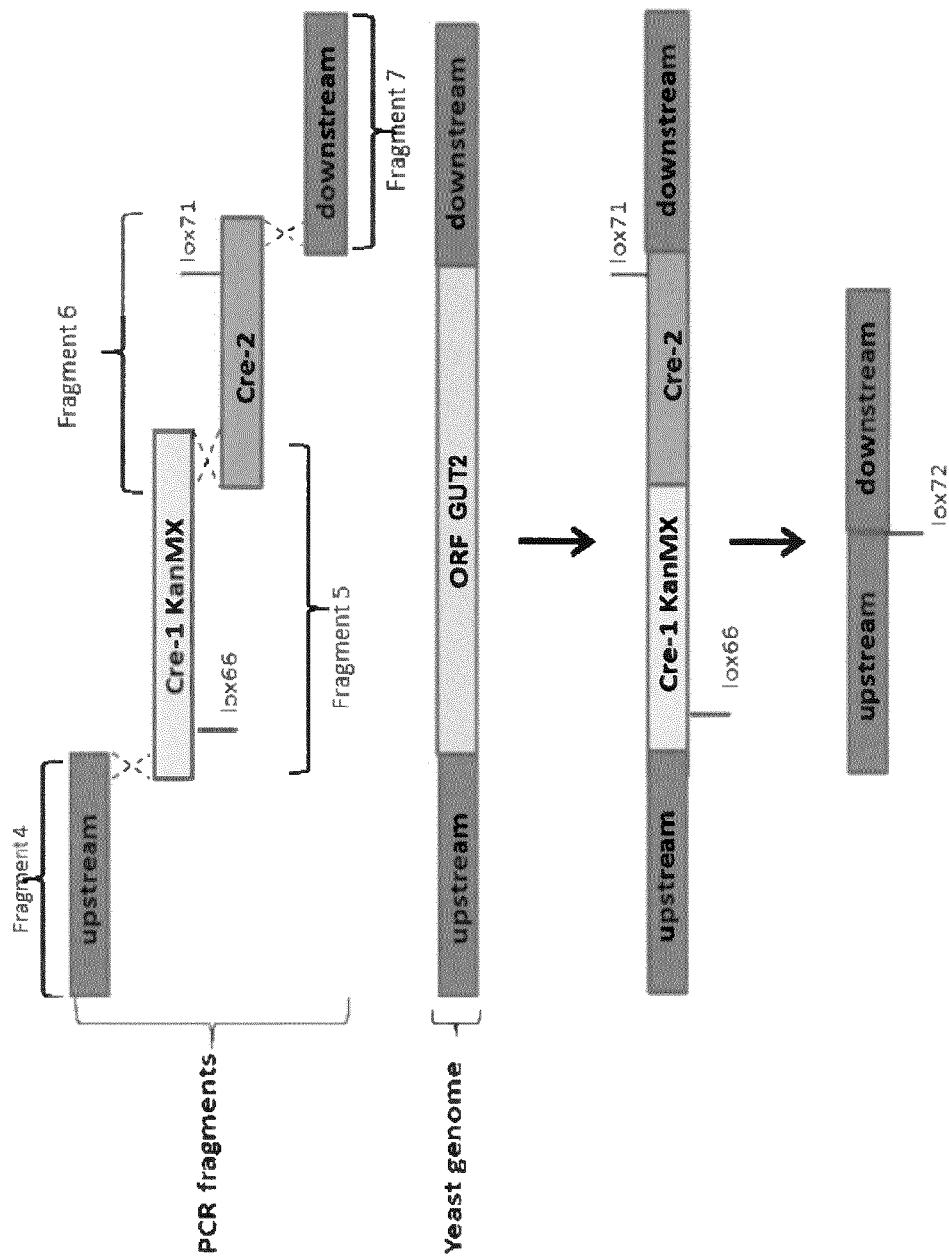
FIG. 4 sets out a schematic depiction of the principle of GUT2 deletion.

Yeast transformation was performed by a method known by persons skilled in the art. S. cerevisiae strain SUC-947 was transformed with purified PCR fragments 4, 5, 6, and 7. PCR fragment 4 contained an overlap with PCR fragment 5 at its 3' end. PCR fragment 7 contained an overlap with PCR fragment 6 at its 5' end. PCR fragment 5 contained an overlap at its 5' end with PCR fragment 4 and at its 3' end with PCR fragment 6, and PCR fragment 6 contained an overlap at its 5' end with PCR fragment 5 and at its 3' end with PCR fragment 7, such that this allowed homologous recombination of all four PCR fragments (FIG. 4). The 5' end of PCR fragment 4 and the 3' end of PCR fragment 7 were homologous to the GUT2 locus and enabled integration of all four PCR fragments in the GUT2 locus. This resulted in one linear fragment consisting of PCR fragments 4 to 7 integrated in the GUT2 locus (FIG. 4). This method of integration is described in Example 1.

Transformation mixtures were plated on YPD-agar (per liter: 10 grams of yeast extract, 20 grams per liter peptone, 20 grams per liter dextrose, 20 grams of agar) containing 200 μg G418 per ml. After three to five days of growth at 30° C., individual transformants were re-streaked on fresh YPD-agar plates containing 200 μg G418 per ml.

Subsequently, the marker cassette and Cre-recombinase are effectively removed via recombination by the method described in PCT/EP2013/055047, resulting in deletion of the GUT2 gene and leaving a lox72 site as a result of recombination between the lox66 and lox71 sites. The resulting markerfree strain was named SUP-003. Strain SUP-003 was able to grow on YPD-agar plates, but unable to grow on YPD-agar plates supplemented with 200 μg G418/ml, confirming the removal of the KanMX marker.

Production of Succinic Acid by SUP-003

A succinic acid production experiment was performed and succinic acid titers were measured as described in General materials and methods. In the supernatant of SUP-003, 2.5% more succinic acid was detected compared to supernatant of SUC-947, as determined in microtiter plate fermentations.

Example 3

Construction of Yeast Strain SUP-001 and Production of Succinic Acid by SUP-001

Generation of PCR Fragments

PCR fragments were generated using Phusion DNA polymerase (New England Biolabs, USA) according to manufacturer's instructions. PCR fragment 8 was generated by using the primer sequences described in SEQ ID NO: 34 and SEQ ID NO: 35, using genomic DNA as template. SEQ ID NO: 35 contains a 27 bp overlap with the 5' region of the NDE1 gene, directly located before the start codon of the NDE1 gene. PCR fragment 9 was generated by using the primer sequences described in SEQ ID NO: 22 and SEQ ID NO: 38, using plasmid pSUC227 (FIG. 5, SEQ ID NO: 43) as template. PCR fragment 10 was generated by using the primer sequences described in SEQ ID NO: 23 and SEQ ID NO: 39, using plasmid pSUC225 (FIG. 6, SEQ ID NO: 44) as template. PCR fragment 11 was generated by using the primer sequences described in SEQ ID NO: 36 and SEQ ID NO: 37, using genomic DNA as template. SEQ ID NO: 36 contains a 18 bp overlap with the 3' region of the NDE1 gene, directly located after the stop codon of the NDE1 gene.

The size of the PCR fragments was checked with standard agarose electrophoresis techniques. PCR amplified DNA fragments were purified using the Zymoclean™ Gel DNA Recovery Kit (Zymo Research, Irvine, Calif., USA) according to manufacturer's instructions.

Transformation to Strain SUC-947 in Order to Construct Strain SUP-001

The Saccharomyces cerevisiae strain SUC-947 was constructed as described in Example 1. Strain SUC-947 was used as a starting point to construct strain SUP-001.

Figure 7:
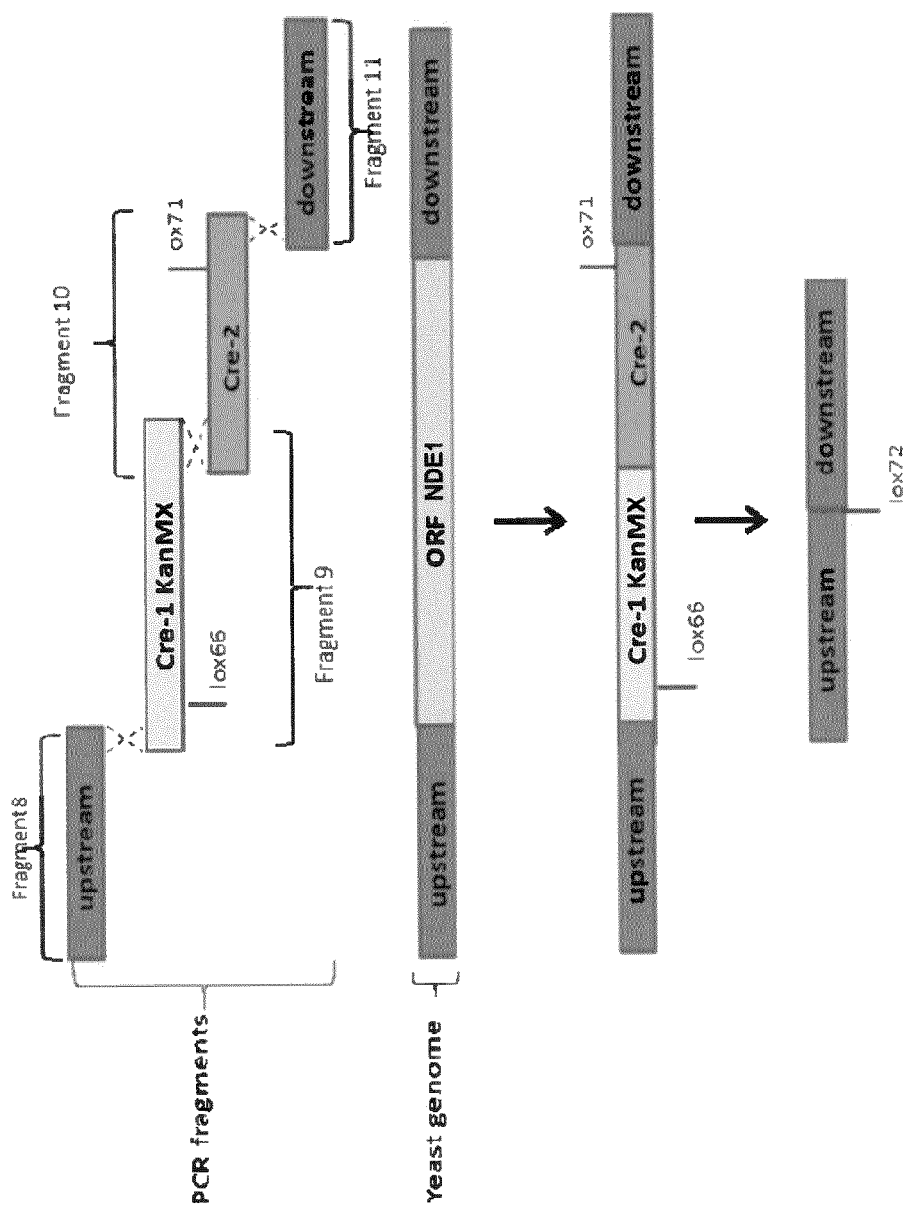
FIG. 7 sets out a schematic depiction of the principle of NDE1 deletion.

Yeast transformation was done by a method known by persons skilled in the art. S. cerevisiae strain SUC-947 was transformed with purified PCR fragments 8, 9, 10, and 11. PCR fragment 8 contained an overlap with PCR fragment 9 at its 3' end. PCR fragment 11 contained an overlap with PCR fragment 10 at its 5' end. PCR fragment 9 contained an overlap at its 5' end with PCR fragment 8 and at its 3' end with PCR fragment 10, and PCR fragment 10 contained an overlap at its 5' end with PCR fragment 9 and at its 3' end with PCR fragment 11, such that this allowed homologous recombination of all four PCR fragments (FIG. 7). The 5' end of PCR fragment 8 and the 3' end of PCR fragment 11 were homologous to the NDE1 locus and enabled integration of all four PCR fragments in the NDE1 locus. This resulted in one linear fragment consisting of PCR fragments 8 to 11 integrated in the NDE1 locus (FIG. 7). This method of integration is described in Example 1.

Transformation mixtures were plated on YPD-agar (per liter: 10 grams of yeast extract, 20 grams per liter peptone, 20 grams per liter dextrose, 20 grams of agar) containing 200 μg G418 per ml. After three to five days of growth at 30° C., individual transformants were re-streaked on fresh YPD-agar plates containing 200 μg G418 per ml.

Subsequently, the marker cassette and Cre-recombinase are effectively removed via recombination by the method described in PCT/EP2013/055047, resulting in deletion of the NDE1 gene and leaving a lox72 site as a result of recombination between the lox66 and lox71 sites. The resulting markerfree strain was named SUP-001. Strain SUP-001 was able to grow on YPD-agar plates, but unable to grow on YPD-agar plates supplemented with 200 μg G418/ml, confirming the removal of the KanMX marker.

Production of Succinic acid by SUP-001

A succinic acid production experiment was performed and succinic acid titers were measured as described in General materials and methods. In the supernatant of SUP-001, 5% more succinic acid was detected compared to supernatant of SUC-947, as determined in microtiter plate fermentations.

Example 4

Construction of Yeast Strain SUP-002 and Production of Succinic Acid by SUP-002

Generation of PCR Fragments

PCR fragments were generated using Phusion DNA polymerase (New England Biolabs, USA) according to manufacturer's instructions. PCR fragment 12 was generated by using the primer sequences described in SEQ ID NO: 28 and SEQ ID NO: 29, using genomic DNA as template. SEQ ID NO: 29 contains a 27 bp overlap with the 5' region of the NDE2 gene, directly located before the start codon of the NDE2 gene. PCR fragment 13 was generated by using the primer sequences described in SEQ ID NO: 22 and SEQ ID NO: 32, using plasmid pSUC227 (FIG. 5, SEQ ID NO: 43) as template. PCR fragment 14 was generated by using the primer sequences described in SEQ ID NO: 23 and SEQ ID NO: 33, using plasmid pSUC225 (FIG. 6, SEQ ID NO: 44) as template. PCR fragment 15 was generated by using the primer sequences described in SEQ ID NO: 30 and SEQ ID NO: 31, using genomic DNA as template. SEQ ID NO: 30 contains a 26 bp overlap with the 3' region of the NDE2 gene, directly located after the stop codon of the NDE2 gene.

The size of the PCR fragments was checked with standard agarose electrophoresis techniques. PCR amplified DNA fragments were purified using the Zymoclean™ Gel DNA Recovery Kit (Zymo Research, Irvine, Calif., USA) according to manufacturer's instructions.

Transformation to Strain SUC-947 in Order to Construct Strain SUP-002

The *Saccharomyces cerevisiae* strain SUC-947 was constructed as described in Example 1. Strain SUC-947 was used as a starting point to construct strain SUP-002.

Figure 8:
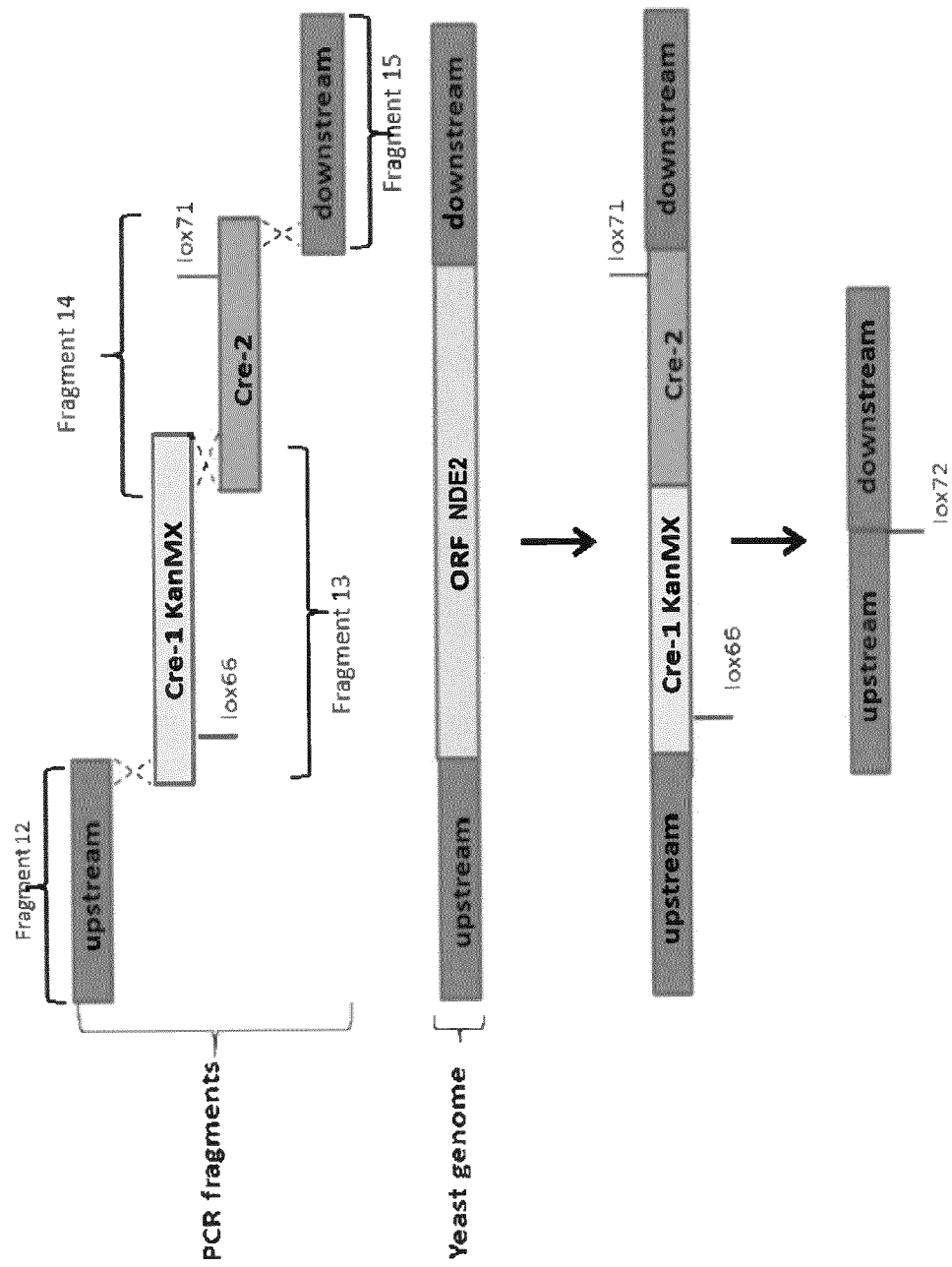
FIG. 8 sets out a schematic depiction of the principle of NDE2 deletion.

Yeast transformation was done by a method known by persons skilled in the art. *S. cerevisiae* strain SUC-947 was transformed with purified PCR fragments 12, 13, 14, and 15. PCR fragment 12 contained an overlap with PCR fragment 13 at its 3' end. PCR fragment 15 contained an overlap with PCR fragment 14 at its 5' end. PCR fragment 13 contained an overlap at its 5' end with PCR fragment 12 and at its 3' end with PCR fragment 14, and PCR fragment 14 contained an overlap at its 5' end with PCR fragment 13 and at its 3' end with PCR fragment 15, such that this allowed homologous recombination of all four PCR fragments (FIG. 8). The 5' end of PCR fragment 12 and the 3' end of PCR fragment 15 were homologous to the NDE2 locus and enabled integration of all four PCR fragments in the NDE2 locus. This resulted in one linear fragment consisting of PCR fragments 12 to 15 integrated in the NDE2 locus (FIG. 8). This method of integration is described in Example 1.

Transformation mixtures were plated on YPD-agar (per liter: 10 grams of yeast extract, 20 grams per liter peptone, 20 grams per liter dextrose, 20 grams of agar) containing 200 µg G418 per ml. After three to five days of growth at 30° C., individual transformants were re-streaked on fresh YPD-agar plates containing 200 µg G418 per ml.

Subsequently, the marker cassette and Cre-recombinase are effectively removed via recombination by the method described in PCT/EP2013/055047, resulting in deletion of the NDE2 gene and leaving a lox72 site as a result of recombination between the lox66 and lox71 sites. The resulting marker free strain was named SUP-002. Strain SUP-002 was able to grow on YPD-agar plates, but unable to grow on YPD-agar plates supplemented with 200 µg G418/ml, confirming the removal of the KanMX marker.

Production of Succinic Acid by SUP-002

A succinic acid production experiment was performed and succinic acid titers were measured as described in General materials and methods. In the supernatant of SUP-002, 2.3% more succinic acid was detected compared to supernatant of SUC-947, as determined in microtiter plate fermentations.

Example 5

Construction of Yeast Strain SUP-004

Transformation of strain SUP-001 in order to construct strain SUP-004 The *Saccharomyces cerevisiae* strain SUP-001 was constructed as described in Example 3. Strain SUP-001 was used as a starting point to construct strain SUP-004. SUP-001 contains a deletion of NDE1. In order to generate an NDE1, NDE2 double deletion, NDE2 was deleted in SUP-001 according to the method described in Example 4.

Example 6

Construction of Yeast Strain SUP-005

Transformation of Strain SUP-004 in Order to Construct Strain SUP-005

The *Saccharomyces cerevisiae* strain SUP-004 was constructed as described in Example 5. Strain SUP-004 was used as a starting point to construct strain SUP-005. SUP-004 contains a double deletion of NDE1 and NDE2. In order to generate an NDE1, NDE2, GUT2 triple deletion, GUT2 was deleted in SUP-004 according to the method as described in Example 2, thereby generating SUP-005.

Example 7

Construction of yeast strain SUP-006

Generation of PCR Fragments

PCR fragments are generated using Phusion DNA polymerase (New England Biolabs, USA) according to manufacturer's instructions. PCR fragment 16 is generated by using the primer sequences described in SEQ ID NO: 45 and SEQ ID NO: 46, using genomic DNA as template. SEQ ID NO: 46 contains a 27 bp overlap with the 5' region of the GPD1 gene, directly located before the start codon of the GPD1 gene. PCR fragment 17 is generated by using the primer sequences described in SEQ ID NO: 47 and SEQ ID NO: 22, using plasmid pSUC227 (FIG. 5, SEQ ID NO: 43) as template. PCR fragment 18 is generated by using the primer sequences described in SEQ ID NO: 23 and SEQ ID NO: 48, using plasmid pSUC225 (FIG. 6, SEQ ID NO: 44) as template. PCR fragment 19 is generated by using the primer sequences described in SEQ ID NO: 49 and SEQ ID NO: 50, using genomic DNA as template. SEQ ID NO: 49 contains a 26 bp overlap with the 3' region of the GPD1 gene, directly located after the stop codon of the GPD1 gene.

The size of the PCR fragments is checked with standard agarose electrophoresis techniques. PCR amplified DNA fragments are purified using the Zymoclean™ Gel DNA Recovery Kit (Zymo Research, Irvine, Calif., USA) according to manufacturer's instructions.

Transformation of Strain SUP-005 in Order to Construct Strain SUP-006

The *Saccharomyces cerevisiae* strain SUP-005 is constructed as described in Example 6. Strain SUP-005 is used as a starting point to construct strain SUP-006.

Figure 9:
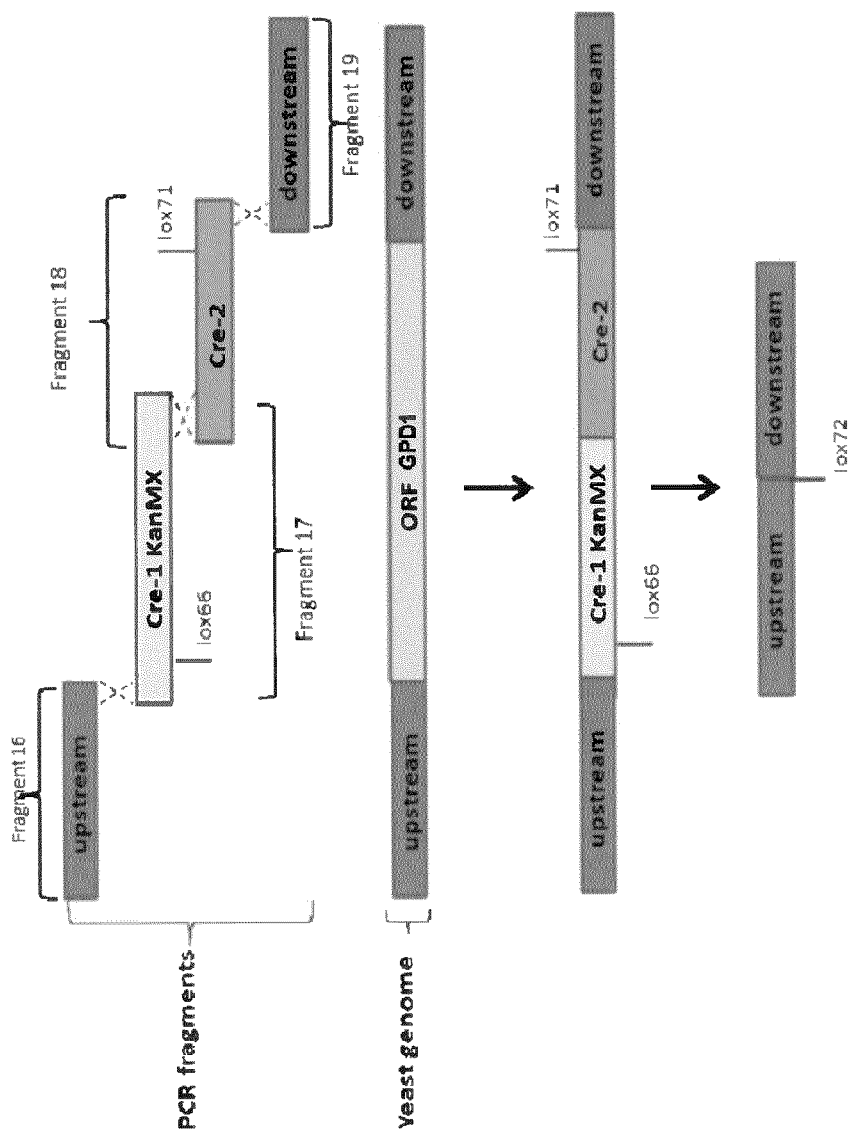
FIG. 9 sets out a schematic depiction of the principle of GPD1 deletion.

Yeast transformation is performed by a method known by persons skilled in the art. *S. cerevisiae* strain SUP-005 is transformed with purified PCR fragments 16, 17, 18, and 19. PCR fragment 16 contains an overlap with PCR fragment 17 at its 3' end. PCR fragment 19 contains an overlap with PCR fragment 18 at its 5' end. PCR fragment 17 contains an overlap at its 5' end with PCR fragment 16 and at its 3' end with PCR fragment 18, and PCR fragment 18 contains an overlap at its 5' end with PCR fragment 17 and at its 3' end with PCR fragment 19, such that this allows homologous recombination of all four PCR fragments (FIG. 9). The 5' end of PCR fragment 16 and the 3' end of PCR fragment 19 are homologous to the GPD1 locus and enables integration of all four PCR fragments in the GPD1 locus. This results in one linear fragment consisting of PCR fragments 16 to 19 integrated in the GPD1 locus (FIG. 9). This method of integration is described in Example 1.

Transformation mixtures are plated on YPD-agar (per liter: 10 grams of yeast extract, 20 grams per liter peptone, 20 grams per liter dextrose, 20 grams of agar) containing 200 μg G418 per ml. After three to five days of growth at 30° C., individual transformants are re-streaked on fresh YPD-agar plates containing 200 μg G418/ml per ml.

Subsequently, the marker cassette and Cre-recombinase are effectively removed via recombination by the method described in PCT/EP2013/055047, resulting in deletion of the GPD1 gene and leaving a lox72 site as a result of recombination between the lox66 and lox71 sites. The resulting marker-free strain is named SUP-006. Strain SUP-006 is able to grow on YPD-agar plates, but unable to grow on YPD-agar plates supplemented with 200 μg G418/ml, confirming the removal of the KanMX marker.

Example 8

Construction of Yeast Strain SUP-007

Generation of PCR Fragments

PCR fragments are generated using Phusion DNA polymerase (New England Biolabs, USA) according to manufacturer's instructions. PCR fragment 20 is generated by using the primer sequences described in SEQ ID NO: 51 and SEQ ID NO: 52, using genomic DNA as template. SEQ ID NO: 52 contains a 27 bp overlap with the 5' region of the GPD2 gene, directly located before the start codon of the GPD2 gene. PCR fragment 21 is generated by using the primer sequences described in SEQ ID NO: 53 and SEQ ID NO: 22, using plasmid pSUC227 (FIG. 5, SEQ ID NO: 43) as template. PCR fragment 22 is generated by using the primer sequences described in SEQ ID NO: 23 and SEQ ID NO: 54, using plasmid pSUC225 (FIG. 6, SEQ ID NO: 44) as template. PCR fragment 23 is generated by using the primer sequences described in SEQ ID NO: 55 and SEQ ID NO: 56, using genomic DNA as template. SEQ ID NO: 55 contains a 26 bp overlap with the 3' region of the GPD2 gene, directly located after the stop codon of the GPD2 gene.

The size of the PCR fragments is checked with standard agarose electrophoresis techniques. PCR amplified DNA fragments are purified using the Zymoclean™ Gel DNA Recovery Kit (Zymo Research, Irvine, Calif., USA) according to manufacturer's instructions.

Transformation of Strain SUP-006 in Order to Construct Strain SUP-007

The Saccharomyces cerevisiae strain SUP-006 is constructed as described in Example 7. Strain SUP-006 is used as a starting point to construct strain SUP-007.

Figure 10:
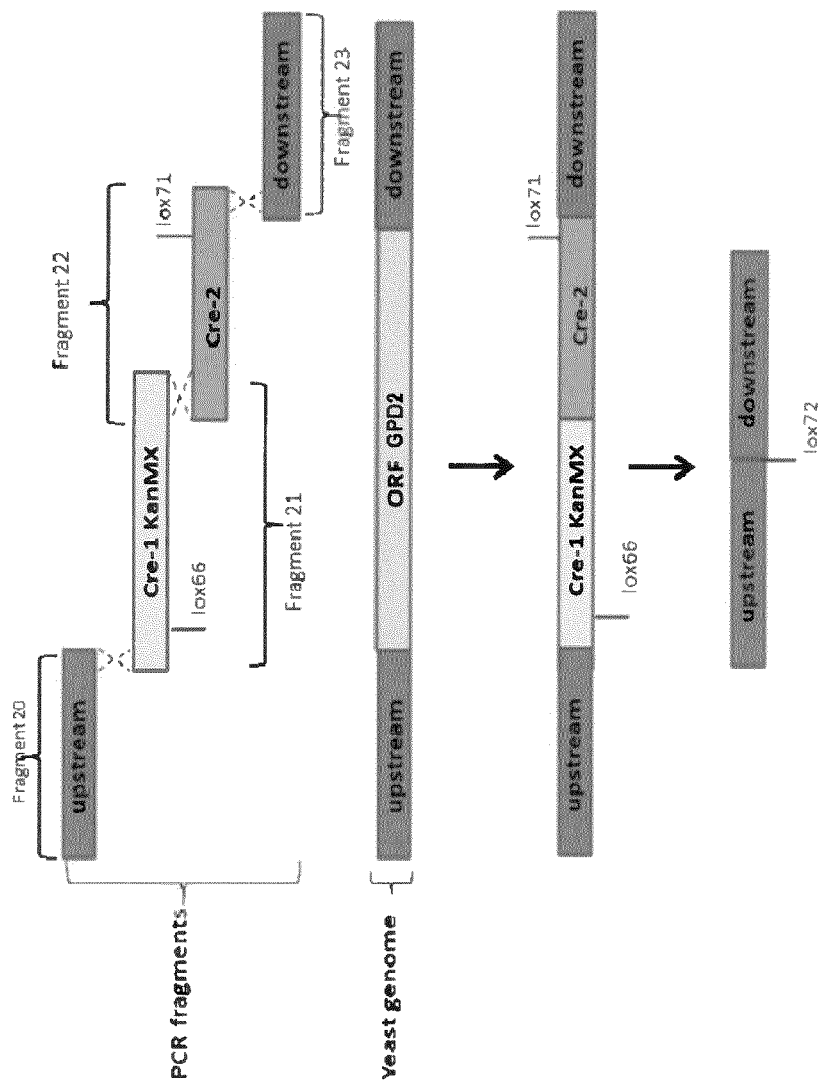
FIG. 10 sets out a schematic depiction of the principle of GPD2 deletion.

Yeast transformation is performed by a method known by persons skilled in the art. S. cerevisiae strain SUP-006 is transformed with purified PCR fragments 20, 21, 22, and 23. PCR fragment 20 contains an overlap with PCR fragment 21 at its 3' end. PCR fragment 23 contains an overlap with PCR fragment 22 at its 5' end. PCR fragment 21 contains an overlap at its 5' end with PCR fragment 20 and at its 3' end with PCR fragment 22, and PCR fragment 22 contains an overlap at its 5' end with PCR fragment 21 and at its 3' end with PCR fragment 23, such that this allows homologous recombination of all four PCR fragments (FIG. 10). The 5' end of PCR fragment 20 and the 3' end of PCR fragment 23 are homologous to the GPD2 locus and enables integration of all four PCR fragments in the GPD2 locus. This results in one linear fragment consisting of PCR fragments 20 to 23 integrated in the GPD2 locus (FIG. 9). This method of integration is described in Example 1.

Transformation mixtures are plated on YPD-agar (per liter: 10 grams of yeast extract, 20 grams per liter peptone, 20 grams per liter dextrose, 20 grams of agar) containing 200 μg G418 per ml. After three to five days of growth at 30° C., individual transformants are re-streaked on fresh YPD-agar plates containing 200 μg G418 per ml.

Subsequently, the marker cassette and Cre-recombinase are effectively removed via recombination by the method described in PCT/EP2013/055047, resulting in deletion of the GPD2 gene and leaving a lox72 site as a result of recombination between the lox66 and lox71 sites. The resulting marker free strain is named SUP-007. Strain SUP-007 is able to grow on YPD-agar plates, but unable to grow on YPD-agar plates supplemented with 200 μg G418/ml, confirming the removal of the KanMX marker.

Example 9

Production of Succinic Acid in SUP-005 and SUP-007

The yeast strains SUC-947, SUP-005 and SUP-007 are cultivated in shake-flask (50 ml) for 3 days at 30° C. and 280 rpm. The medium is based on Verduyn et al. (Verduyn C, Postma E, Scheffers W A, Van Dijken J P. Yeast, 1992 July; 8(7):501-517), with modifications in the carbon and nitrogen sources, as described herein below.

TABLE 2

| Pre-culture medium composition | | |
|---|---|---|
| Raw material | | Concentration (g/kg) |
| Galactose | $C_6H_{12}O_6 \cdot H_2O$ | 20.00 |
| Urea | $(NH_2)_2CO$ | 2.30 |
| Potassium dihydrogen phosphate | $KH_2PO_4$ | 3.00 |
| Magnesium sulphate | $MgSO_4 \cdot 7H_2O$ | 0.50 |
| Trace element solution[a] | | 1.00 |
| Vitamin solution[b] | | 1.00 |
| Chalk | $CaCO_3$ | 1.00 |
| Component | Formula | Concentration (g/kg) |
| [a]Trace elements solution | | |
| EDTA | $C_{10}H_{14}N_2Na_2O_8 \cdot 2H_2O$ | 15.00 |
| Zincsulphate·7H$_2$O | $ZnSO_4 \cdot 7H_2O$ | 4.50 |
| Manganesechloride·2H$_2$O | $MnCl_2 \cdot 2H_2O$ | 0.84 |
| Cobalt (II) chloride·6H$_2$O | $CoCl_2 \cdot 6H_2O$ | 0.30 |
| Copper (II) sulphate·5H$_2$O | $CuSO_4 \cdot 5H_2O$ | 0.30 |
| Sodium molybdenum·2H$_2$O | $Na_2MoO_4 \cdot 2H_2O$ | 0.40 |
| Calciumchloride·2H$_2$O | $CaCl_2 \cdot 2H_2O$ | 4.50 |
| Ironsulphate·7H$_2$O | $FeSO_4 \cdot 7H_2O$ | 3.00 |
| Boric acid | $H_3BO_3$ | 1.00 |
| Potassium iodide | KI | 0.10 |
| [b]Vitamin solution | | |
| Biotin (D−) | $C_{10}H_{16}N_2O_3S$ | 0.05 |
| Ca D(+) panthothenate | $C_{18}H_{32}CaN_2O_{10}$ | 1.00 |
| Nicotinic acid | $C_6H_5NO_2$ | 1.00 |
| Myo-inositol | $C_6H_{12}O_6$ | 25.00 |
| Thiamine chloride hydrochloride | $C_{12}H_{18}Cl_2N_4OS \cdot xH_2O$ | 1.00 |
| Pyridoxol hydrochloride | $C_8H_{12}ClNO_3$ | 1.00 |
| p-aminobenzoic acid | $C_7H_7NO_2$ | 0.20 |

Subsequently, ~3 ml of the content of the shake-flask is transferred into a seed fermenter (starting volume 0.3 kg, 1% inoculation strength), which contains the medium set out in Table 3.

TABLE 3

Medium composition of the seed fermenter

| Raw material | | Concentration (g/kg) |
|---|---|---|
| Ammonium sulphate | $(NH_4)_2SO_4$ | 1.00 |
| Potassium dihydrogen phosphate | $KH_2PO_4$ | 10.00 |
| Magnesium sulphate | $MgSO_4 \cdot 7H_2O$ | 5.00 |
| Trace element solution | | 8.00 |
| Vitamin solution | | 8.00 |

The pH is controlled at 5.0 by addition of ammonia (10 wt %). Temperature is controlled at 30° C. $pO_2$ is controlled at 25% (relative to air saturation) by adjusting the stirrer speed. Total airflow applied is 18 NL/h. Glucose concentration is kept limited by controlled feed to the fermenter (exponent of 0.15 was applied).

After 68 hours of fermentation, 80 g of culture broth of the seed fermenter is transferred to a production fermenter (starting volume 0.4 kg), with the medium set out in Table 4.

TABLE 4

Medium composition of the production fermenter

| Raw material | | Concentration (g/kg) |
|---|---|---|
| Urea | $(NH_2)_2CO$ | 1.00 |
| Potassium dihydrogen phosphate | $KH_2PO_4$ | 1.50 |
| Magnesium sulphate | $MgSO_4 \cdot 7H_2O$ | 0.50 |
| Iron sulphate·$7H_2O$ | $FeSO_4 \cdot 7H_2O$ | 0.006 |
| Chalk | $CaCO_3$ | 12.50 |
| Biotin | $C_{10}H_{16}N_2O_3S$ | 0.001 |

No pH control is applied, as the added $CaCO_3$ initially buffered the medium at the pH of 5-5.5. As result of natural acidification the pH drops towards 3 at the end of fermentation. Temperature is controlled at 30° C. Total gas flow applied is 12 NL/h, 50% air and 50% $CO_2$. Glucose concentration is kept limited by controlled feed (glucose concentration in feed was 423 g/kg) to the fermenter (0-9 h: 5.6 ml/h g/L/h; >9 h: feed in ml/h=$(0.0003*(t)^2-0.1028*(t)+7.8991)*4/5$). When necessary, these rates are adjusted accordingly.

Glucose and succinic acid are analyzed with NMR after 48 hours of fermentation time. Supernatants of fermentation samples are diluted twice (1:1) in MilliQ water.

Approximately 500 mg sample is weighed accurately into a suitable vial, and approximately 500 mg internal standard solution (containing 10 g/L maleic acid in $D_2O$) is weighed into this vial. Subsequently the vial is placed in a pre-heated water bath (100 degrees) and the samples are boiled for 10 minutes. The material is lyophilized and dissolved in 1 mL $D_2O$ containing trace amounts of DSS (4,4-dimethyl-4-silapentane-1-sulfonic acid).

1D 1H NMR spectra are recorded on a BEST Bruker Avance III spectrometer, operating at a proton frequency of 500 MHz, equipped with a He-cooled cryo probe, using a pulse program without water suppression (ZG) at a temperature of 300 K, with a 90 degree excitation pulse, acquisition time of 2.0 seconds and a relaxation delay of 40 seconds. The number of scans was set at 8, dummy scans are not used.

The malic acid concentration [in g/l] is calculated based on the following signals (δ relative to 4,4-dimethyl-4-silapentane-1-sulfonic acid):
Malic acid: first dd of malic acid signals at 2.92 ppm n=1H (malic acid α-CH2 signal is a ddd, 2.89 ppm, 2H J=4 Hz, J=17 Hz, J=44 Hz)
The succinic acid concentration [in g/L] is calculated based on the following signals (δ relative to 4,4-dimethyl-4-silapentane-1-sulfonic acid):
Succinic acid: succinic acid signal at 2.67 ppm (s, 4H)
The signal used for the standard: maleic acid peak around 6.3 ppm (S, 2H).
Quantification by NMR is described by *Bharti et al., 2012, TrAC Trends in Analytical Chemistry* 35:5-26.

The fermentation yield (g succinic acid/g glucose) is calculated by dividing the amount of produced succinic acid by the total amount of consumed sugars, including during the biomass propagation phase.

Strain SUP-005 containing the nde1, nde2, gut2 triple deletion shows a 2% increase in the fermentation yield of succinic acid as compared to SUC-947, as determined in controlled fed-batch fermentations. A combination of deletions in genes encoding a mitochondrial external NADH dehydrogenase (e.g. nde1 and/or nde2) and a mitochondrial glycerol-3-phosphate dehydrogenase (e.g. gut2) is shown to have a beneficial effect on the fermentation yield of succinic acid in a host cell.

Strain SUP-007 containing the nde1, nde2, gut2, gpd1 and gpd2 quintuple deletion shows a further increase in the fermentation yield of succinic acid; that is a 6% increase as compared to SUC-947, as determined in controlled fed-batch fermentations. The succinic acid titer showed a 6% increase as compared to SUC-947, as determined in controlled fed-batch fermentations. A deletion in a gene encoding a cytosolic glycerol-3-phosphate dehydrogenase enzyme (e.g. gpd1 and/or gpd2 deletion) is shown to have a further beneficial effect on the titer and fermentation yield of succinic acid in a host cell.

---

The invention claimed is:

1. A yeast host cell which is capable of producing a dicarboxylic acid and which comprises a genetic modification in its genome resulting in the deficiency of
mitochondrial external NADH dehydrogenase;
mitochondrial glycerol-3-phosphate dehydrogenase; and
cytosolic glycerol-3-phosphate dehydrogenase,
wherein the genetic modification results in reduced oxidation of a reduced form of NADH, NADPH or FADH$_2$ as compared to the oxidation of NADH, NADPH or FADH$_2$ in a parent host cell that has not been modified in its genome in the same way,
and wherein the host cell overexpresses a fumarase in E.C. 4.2.1.2 or a fumarate reductase in E.C. 1.3.1.6.

2. The host cell according to claim 1, wherein the host cell further comprises at least one genetic modification in its genome resulting in the deficiency of at least one:
alcohol dehydrogenase or aldehyde dehydrogenase.

3. The yeast host cell according to claim 1, wherein the—at least one-mitochondrial external NADH dehydrogenase has an amino acid sequence comprising a sequence as set out in SEQ ID NO: 40 or comprising a sequence having at least 80% identity with SEQ ID NO: 40; or wherein the—at least one mitochondrial external NADH dehydrogenase has an amino acid sequence comprising a sequence as set out in SEQ ID NO: 41 or comprising a sequence having at least 80% identity with SEQ ID NO: 41; or wherein the—at least one mitochondrial glycerol-3-phosphate dehydrogenase has an amino acid sequence comprising a sequence as set out in SEQ ID NO: 42 or comprising a sequence having at least 80% identity with SEQ ID NO: 42; wherein the—at least one cytosolic glycerol-3-phosphate dehydrogenase has an amino acid sequence comprising a sequence as set out in SEQ ID NO: 57 or comprising a sequence having at least 80% identity with SEQ ID NO: 57; or wherein the—at least one cytosolic glycerol-3-phosphate dehydrogenase has an amino acid sequence comprising a sequence as set out in SEQ ID NO: 58 or comprising a sequence having at least 80% identity with SEQ ID NO: 58.

4. The yeast host cell according to claim 3, wherein the host cell comprises at least one genetic modification in its genome resulting in the deficiency of: —at least one mitochondrial external NADH dehydrogenase having an amino acid sequence comprising a sequence as set out in SEQ ID NO: 40 or comprising a sequence having at least 80% identity with SEQ ID NO: 40; and —at least one mitochondrial external NADH dehydrogenase having an amino acid sequence comprising a sequence as set out in SEQ ID NO: 41 or comprising a sequence having at least 80% identity with SEQ ID NO: 41.

5. The yeast host cell according to claim 3, wherein the host cell comprises at least one genetic modification in its genome resulting in the deficiency of: —at least one cytosolic glycerol-3-phosphate dehydrogenase having an amino acid sequence comprising a sequence as set out in SEQ ID NO: 57 or comprising a sequence having at least 80% identity with SEQ ID NO: 57; and —at least one cytosolic glycerol-3-phosphate dehydrogenase having an amino acid sequence comprising a sequence as set out in SEQ ID NO: 58 or comprising a sequence having at least 80% identity with SEQ ID NO: 58.

6. The yeast host cell according to claim 5, wherein the host cell further comprises at least one genetic modification in its genome resulting in the deficiency of:
at least one alcohol dehydrogenase; or
at least one aldehyde dehydrogenase; or
a combination thereof.

7. The yeast host cell according to claim 1, which comprises a reductive TCA pathway.

8. The yeast host cell according to claim 1, which comprises enzymes selected from the group of enzymes catalyzing the reactions of:
pyruvate to oxaloacetate and/or phosphoenolpyruvate to oxaloacetate;
oxaloacetate to malate;
malate to fumarate; and
fumarate to succinate.

9. The yeast host cell according to claim 1, which comprises a dicarboxylic acid transporter which exports the dicarboxylic acid from inside the cell to the extracellular environment.

10. The yeast host cell according to claim 1, wherein the host cell comprises one or more copies of a nucleic acid encoding one or more of a phosphoenolpyruvate carboxykinase, a phosphoenolpyruvate carboxylase, a pyruvate carboxylase, a malate dehydrogenase, and/or a dicarboxylic acid transporter.

11. The yeast host cell according to claim 1, which is a selected from the group consisting of *Candida, Hansenula, Issatchenkia, Kluyveromyces, Pichia, Saccharomyces, Schizosaccharomyces,* or *Yarrowia* strains, or a filamentous fungal cell selected from the group consisting *Acremonium, Aspergillus, Chrysosporium, Myceliophthora, Penicillium, Talaromyces, Rasamsonia, Thielavia, Fusarium* or *Trichoderma*.

12. A process for producing a dicarboxylic acid, which method comprises fermenting the yeast host cell according to claim 1, in a suitable fermentation medium and producing the dicarboxylic acid.

13. The process according to claim 12, further comprising recovering the dicarboxylic acid from the fermentation medium.

14. The process according to claim 13, further comprising converting the recovered dicarboxylic acid into a product, wherein said product is a deicing agent, a food additive, a cosmetic additive, a surfactant or a polymer.

15. The process according to claim 12, wherein the dicarboxylic acid is succinic acid, fumaric acid and/or malic acid.

* * * * *